United States Patent
Pavlovskaia et al.

(10) Patent No.: US 8,311,306 B2
(45) Date of Patent: Nov. 13, 2012

(54) SYSTEM AND METHOD FOR IMAGE SEGMENTATION IN GENERATING COMPUTER MODELS OF A JOINT TO UNDERGO ARTHROPLASTY

(75) Inventors: Elena Pavlovskaia, San Francisco, CA (US); Venkata S. Sarva, Fremont, CA (US)

(73) Assignee: OtisMed Corporation, Alameda, CA (US)

( * ) Notice: Subject to any disclaimer, the term of this patent is extended or adjusted under 35 U.S.C. 154(b) by 610 days.

(21) Appl. No.: 12/386,105

(22) Filed: Apr. 14, 2009

(65) Prior Publication Data
US 2009/0274350 A1    Nov. 5, 2009

Related U.S. Application Data

(60) Provisional application No. 61/126,102, filed on Apr. 30, 2008.

(51) Int. Cl.
*G06K 9/00* (2006.01)
(52) U.S. Cl. ........................................ 382/131
(58) Field of Classification Search ............ 382/131
See application file for complete search history.

(56) References Cited

U.S. PATENT DOCUMENTS

| | | |
|---|---|---|
| 3,195,411 A | 7/1965 | MacDonald et al. |
| 3,825,151 A | 7/1974 | Arnaud |
| D245,920 S | 9/1977 | Shen |
| 4,298,992 A | 11/1981 | Burstein |
| 4,436,684 A | 3/1984 | White |
| D274,093 S | 5/1984 | Kenna |
| D274,161 S | 6/1984 | Kenna |
| 4,575,330 A | 3/1986 | Hull |
| 4,821,213 A | 4/1989 | Cline et al. |
| 4,822,365 A | 4/1989 | Walker et al. |
| 4,931,056 A | 6/1990 | Ghajar et al. |
| 4,936,862 A | 6/1990 | Walker et al. |
| 5,027,281 A | 6/1991 | Rekow et al. |
| 5,075,866 A | 12/1991 | Goto et al. |
| 5,078,719 A | 1/1992 | Schreiber |
| 5,098,383 A | 3/1992 | Hemmy et al. |
| 5,122,144 A | 6/1992 | Bert et al. |
| 5,123,927 A | 6/1992 | Duncan et al. |
| 5,140,646 A | 8/1992 | Ueda |
| 5,156,777 A | 10/1992 | Kaye |
| 5,171,276 A | 12/1992 | Caspari et al. |

(Continued)

FOREIGN PATENT DOCUMENTS

DE    3305237 A1    8/1983
(Continued)

OTHER PUBLICATIONS

U.S. Appl. No. 10/146,862, filed May 15, 2002, Park et al.

(Continued)

*Primary Examiner* — Rodney Fuller
(74) *Attorney, Agent, or Firm* — Polsinelli Shughart PC

(57) ABSTRACT

Systems and methods for image segmentation in generating computer models of a joint to undergo arthroplasty are disclosed. Some embodiments may include a method of partitioning an image of a bone into a plurality of regions, where the method may include obtaining a plurality of volumetric image slices of the bone, generating a plurality of spline curves associated with the bone, verifying that at least one of the plurality of spline curves follow a surface of the bone, and creating a 3D mesh representation based upon the at least one of the plurality of spline curve.

34 Claims, 52 Drawing Sheets

U.S. PATENT DOCUMENTS

| | | | |
|---|---|---|---|
| D336,518 S | 6/1993 | Taylor |
| 5,218,427 A | 6/1993 | Koch |
| 5,234,433 A | 8/1993 | Bert et al. |
| 5,274,565 A | 12/1993 | Reuben |
| 5,298,115 A | 3/1994 | Leonard |
| D346,979 S | 5/1994 | Stalcup et al. |
| 5,320,529 A | 6/1994 | Pompa |
| 5,360,446 A | 11/1994 | Kennedy |
| 5,364,402 A | 11/1994 | Mumme et al. |
| 5,365,996 A | 11/1994 | Crook |
| D355,254 S | 2/1995 | Krafft et al. |
| 5,408,409 A | 4/1995 | Glassman et al. |
| 5,448,489 A | 9/1995 | Reuben |
| 5,452,407 A | 9/1995 | Crook |
| 5,462,550 A | 10/1995 | Dietz et al. |
| 5,484,446 A | 1/1996 | Burke et al. |
| D372,309 S | 7/1996 | Heldreth |
| D374,078 S | 9/1996 | Johnson et al. |
| 5,556,278 A | 9/1996 | Meitner |
| 5,569,261 A | 10/1996 | Marik et al. |
| 5,601,563 A | 2/1997 | Burke et al. |
| 5,662,656 A | 9/1997 | White |
| 5,682,886 A | 11/1997 | Delp et al. |
| 5,683,398 A | 11/1997 | Carls et al. |
| 5,716,361 A | 2/1998 | Masini |
| 5,725,376 A | 3/1998 | Poirier |
| 5,749,876 A | 5/1998 | Duvillier et al. |
| 5,768,134 A | 6/1998 | Swaelens et al. |
| 5,769,859 A | 6/1998 | Dorsey |
| D398,058 S | 9/1998 | Collier |
| 5,810,830 A | 9/1998 | Noble et al. |
| 5,824,100 A | 10/1998 | Kester et al. |
| 5,824,111 A | 10/1998 | Schall et al. |
| 5,860,980 A | 1/1999 | Axelson, Jr. et al. |
| 5,860,981 A | 1/1999 | Bertin et al. |
| 5,871,018 A | 2/1999 | Delp et al. |
| 5,880,976 A | 3/1999 | DiGioia III et al. |
| 5,908,424 A | 6/1999 | Bertin et al. |
| 5,964,808 A | 10/1999 | Blaha et al. |
| 5,967,777 A | 10/1999 | Klein et al. |
| 5,993,448 A | 11/1999 | Remmler |
| 6,002,859 A | 12/1999 | DiGioia, III et al. |
| 6,068,658 A | 5/2000 | Insall et al. |
| 6,090,114 A | 7/2000 | Matsuno et al. |
| 6,096,043 A | 8/2000 | Techiera et al. |
| 6,106,529 A | 8/2000 | Techiera |
| 6,112,109 A | 8/2000 | D'Urso |
| 6,132,447 A | 10/2000 | Dorsey |
| 6,171,340 B1 | 1/2001 | McDowell |
| 6,205,411 B1 | 3/2001 | DiGioia, III et al. |
| 6,228,121 B1 | 5/2001 | Khalili |
| 6,254,639 B1 | 7/2001 | Peckitt |
| 6,343,987 B2 | 2/2002 | Hayama et al. |
| 6,382,975 B1 | 5/2002 | Poirier |
| 6,383,228 B1 | 5/2002 | Schmotzer |
| 6,415,171 B1 | 7/2002 | Gueziec et al. |
| 6,458,135 B1 | 10/2002 | Harwin et al. |
| 6,463,351 B1 | 10/2002 | Clynch |
| 6,503,254 B2 | 1/2003 | Masini |
| 6,510,334 B1 | 1/2003 | Schuster et al. |
| 6,520,964 B2 | 2/2003 | Tallarida et al. |
| 6,575,980 B1 | 6/2003 | Robie et al. |
| 6,602,259 B1 | 8/2003 | Masini |
| 6,672,870 B2 | 1/2004 | Knapp |
| 6,692,448 B2 | 2/2004 | Tanaka et al. |
| 6,701,174 B1 | 3/2004 | Krause et al. |
| 6,711,432 B1 | 3/2004 | Krause et al. |
| 6,712,856 B1 | 3/2004 | Carignan et al. |
| 6,716,249 B2 | 4/2004 | Hyde |
| 6,738,657 B1 | 5/2004 | Franklin et al. |
| 6,747,646 B2 | 6/2004 | Gueziec et al. |
| 6,770,099 B2 | 8/2004 | Andriacchi et al. |
| 6,772,026 B2 | 8/2004 | Bradbury et al. |
| 6,814,575 B2 | 11/2004 | Poirier |
| 6,905,510 B2 | 6/2005 | Saab |
| 6,905,514 B2 | 6/2005 | Carignan et al. |
| 6,923,817 B2 | 8/2005 | Carson et al. |
| 6,932,842 B1 | 8/2005 | Litschko et al. |
| 6,944,518 B2 | 9/2005 | Roose |
| 6,955,345 B2 | 10/2005 | Kato |
| 6,969,393 B2 | 11/2005 | Pinczewski et al. |
| 6,975,894 B2 | 12/2005 | Wehrli et al. |
| 6,978,188 B1 | 12/2005 | Christensen |
| 7,029,479 B2 | 4/2006 | Tallarida et al. |
| 7,039,225 B2 | 5/2006 | Tanaka et al. |
| 7,060,074 B2 | 6/2006 | Rosa et al. |
| 7,074,241 B2 | 7/2006 | McKinnon |
| 7,090,677 B2 | 8/2006 | Fallin et al. |
| RE39,301 E | 9/2006 | Bertin |
| 7,104,997 B2 | 9/2006 | Lionberger et al. |
| 7,128,745 B2 | 10/2006 | Masini |
| D532,515 S | 11/2006 | Buttler et al. |
| 7,141,053 B2 | 11/2006 | Rose et al. |
| 7,153,309 B2 | 12/2006 | Huebner et al. |
| 7,184,814 B2 | 2/2007 | Lang et al. |
| 7,235,080 B2 | 6/2007 | Hodorek |
| 7,238,190 B2 | 7/2007 | Schon et al. |
| 7,239,908 B1 | 7/2007 | Alexander et al. |
| 7,309,339 B2 | 12/2007 | Cusick et al. |
| 7,340,316 B2 | 3/2008 | Spaeth et al. |
| 7,359,746 B2 | 4/2008 | Arata |
| 7,392,076 B2 | 6/2008 | de La Barrera |
| 7,393,012 B2 | 7/2008 | Funakura et al. |
| 7,394,946 B2 | 7/2008 | Dewaele |
| 7,468,075 B2 | 12/2008 | Lang et al. |
| 7,517,365 B2 | 4/2009 | Carignan et al. |
| 7,534,263 B2 | 5/2009 | Burdulis, Jr. et al. |
| 7,542,791 B2 | 6/2009 | Mire et al. |
| 7,547,307 B2 | 6/2009 | Carson et al. |
| 7,611,519 B2 | 11/2009 | Lefevre et al. |
| 7,616,800 B2 * | 11/2009 | Paik et al. ............... 382/131 |
| 7,618,421 B2 | 11/2009 | Axelson, Jr. et al. |
| 7,618,451 B2 | 11/2009 | Berez et al. |
| 7,634,119 B2 | 12/2009 | Tsougarakis et al. |
| 7,634,306 B2 | 12/2009 | Sarin et al. |
| 7,641,660 B2 | 1/2010 | Lakin et al. |
| 7,643,862 B2 | 1/2010 | Schoenefeld |
| 7,693,321 B2 | 4/2010 | Lehtonen-Krause |
| D618,796 S | 6/2010 | Cantu et al. |
| D619,718 S | 7/2010 | Gannoe et al. |
| D622,854 S | 8/2010 | Otto et al. |
| D626,234 S | 10/2010 | Otto et al. |
| 7,881,768 B2 | 2/2011 | Lang et al. |
| D642,263 S | 7/2011 | Park |
| 8,036,729 B2 | 10/2011 | Lang et al. |
| 8,160,345 B2 | 4/2012 | Pavlovskaia et al. |
| 8,221,430 B2 | 7/2012 | Park et al. |
| 2002/0087274 A1 | 7/2002 | Alexander et al. |
| 2002/0160337 A1 | 10/2002 | Klein et al. |
| 2003/0009167 A1 | 1/2003 | Wozencroft |
| 2003/0055502 A1 | 3/2003 | Lang et al. |
| 2003/0176783 A1 | 9/2003 | Hu |
| 2004/0097952 A1 | 5/2004 | Sarin et al. |
| 2004/0102792 A1 | 5/2004 | Sarin et al. |
| 2004/0102866 A1 | 5/2004 | Harris et al. |
| 2004/0133276 A1 | 7/2004 | Lang et al. |
| 2004/0138754 A1 | 7/2004 | Lang et al. |
| 2004/0147927 A1 | 7/2004 | Tsougarakis et al. |
| 2004/0152970 A1 | 8/2004 | Hunter et al. |
| 2004/0153066 A1 | 8/2004 | Coon et al. |
| 2004/0153079 A1 | 8/2004 | Tsougarakis et al. |
| 2004/0204760 A1 | 10/2004 | Fitz et al. |
| 2004/0220583 A1 | 11/2004 | Pieczynski, II et al. |
| 2004/0236424 A1 | 11/2004 | Berez et al. |
| 2004/0243148 A1 | 12/2004 | Wasielewski |
| 2004/0243481 A1 | 12/2004 | Bradbury et al. |
| 2004/0254584 A1 | 12/2004 | Sarin et al. |
| 2005/0059978 A1 | 3/2005 | Sherry et al. |
| 2005/0065617 A1 | 3/2005 | de la Barrera et al. |
| 2005/0113841 A1 | 5/2005 | Sheldon et al. |
| 2005/0148843 A1 | 7/2005 | Roose |
| 2005/0148860 A1 | 7/2005 | Liew et al. |
| 2005/0192588 A1 | 9/2005 | Garcia |
| 2005/0201509 A1 | 9/2005 | Mostafavi et al. |
| 2005/0216024 A1 | 9/2005 | Massoud |
| 2005/0245934 A1 | 11/2005 | Tuke et al. |
| 2005/0245936 A1 | 11/2005 | Tuke et al. |

| | | |
|---|---|---|
| 2005/0256389 A1 | 11/2005 | Koga et al. |
| 2005/0267584 A1 | 12/2005 | Burdulis, Jr. et al. |
| 2006/0015018 A1 | 1/2006 | Jutras et al. |
| 2006/0015109 A1 | 1/2006 | Haines |
| 2006/0015188 A1 | 1/2006 | Grimes |
| 2006/0030853 A1 | 2/2006 | Haines |
| 2006/0036257 A1 | 2/2006 | Steffensmeier |
| 2006/0110017 A1 | 5/2006 | Tsai et al. |
| 2006/0111628 A1 | 5/2006 | Tsai et al. |
| 2006/0122491 A1 | 6/2006 | Murray et al. |
| 2006/0155293 A1 | 7/2006 | McGinley et al. |
| 2006/0155294 A1 | 7/2006 | Steffensmeier et al. |
| 2006/0195113 A1 | 8/2006 | Masini |
| 2006/0271058 A1 | 11/2006 | Ashton et al. |
| 2006/0293681 A1 | 12/2006 | Claypool et al. |
| 2007/0005073 A1 | 1/2007 | Claypool et al. |
| 2007/0021838 A1 | 1/2007 | Dugas et al. |
| 2007/0038059 A1 | 2/2007 | Sheffer et al. |
| 2007/0055268 A1 | 3/2007 | Utz et al. |
| 2007/0073305 A1 | 3/2007 | Lionberger et al. |
| 2007/0100462 A1 | 5/2007 | Lang et al. |
| 2007/0106389 A1 | 5/2007 | Croxton et al. |
| 2007/0118055 A1 | 5/2007 | McCombs |
| 2007/0118243 A1 | 5/2007 | Schroeder et al. |
| 2007/0123912 A1 | 5/2007 | Carson |
| 2007/0162039 A1 | 7/2007 | Wozencroft |
| 2007/0167833 A1 | 7/2007 | Redel et al. |
| 2007/0173858 A1 | 7/2007 | Engh et al. |
| 2007/0191741 A1 | 8/2007 | Tsai et al. |
| 2007/0198022 A1 | 8/2007 | Lang et al. |
| 2007/0211928 A1* | 9/2007 | Weng et al. ............ 382/128 |
| 2007/0213738 A1 | 9/2007 | Martin et al. |
| 2007/0219560 A1 | 9/2007 | Hodorek |
| 2007/0226986 A1 | 10/2007 | Chi et al. |
| 2007/0232959 A1 | 10/2007 | Couture et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0239167 A1 | 10/2007 | Pinczewski et al. |
| 2007/0249967 A1 | 10/2007 | Buly et al. |
| 2007/0276224 A1 | 11/2007 | Lang et al. |
| 2007/0276400 A1 | 11/2007 | Moore et al. |
| 2007/0282451 A1 | 12/2007 | Metzger et al. |
| 2007/0288030 A1 | 12/2007 | Metzger et al. |
| 2008/0004701 A1 | 1/2008 | Axelson et al. |
| 2008/0015433 A1 | 1/2008 | Alexander et al. |
| 2008/0015599 A1 | 1/2008 | D'Alessio et al. |
| 2008/0015600 A1 | 1/2008 | D'Alessio et al. |
| 2008/0015602 A1 | 1/2008 | Axelson et al. |
| 2008/0015606 A1 | 1/2008 | D'Alessio et al. |
| 2008/0015607 A1 | 1/2008 | D'Alessio et al. |
| 2008/0031412 A1 | 2/2008 | Lang et al. |
| 2008/0033442 A1 | 2/2008 | Amiot et al. |
| 2008/0088761 A1 | 4/2008 | Lin et al. |
| 2008/0114370 A1 | 5/2008 | Schoenefeld |
| 2008/0137926 A1* | 6/2008 | Skinner et al. ............ 382/131 |
| 2008/0147072 A1 | 6/2008 | Park et al. |
| 2008/0153067 A1 | 6/2008 | Berckmans et al. |
| 2008/0161815 A1 | 7/2008 | Schoenefeld et al. |
| 2008/0195108 A1 | 8/2008 | Bhatnagar et al. |
| 2008/0215059 A1 | 9/2008 | Carignan et al. |
| 2008/0234685 A1 | 9/2008 | Gjerde |
| 2008/0243127 A1 | 10/2008 | Lang et al. |
| 2008/0257363 A1 | 10/2008 | Schoenefeld et al. |
| 2008/0262624 A1 | 10/2008 | White et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0286722 A1 | 11/2008 | Berckmans, III et al. |
| 2008/0287953 A1 | 11/2008 | Sers |
| 2008/0287954 A1 | 11/2008 | Kunz et al. |
| 2008/0312659 A1 | 12/2008 | Metzger et al. |
| 2008/0319491 A1 | 12/2008 | Schoenefeld |
| 2009/0024131 A1 | 1/2009 | Metzger et al. |
| 2009/0088763 A1 | 4/2009 | Aram et al. |
| 2009/0093816 A1 | 4/2009 | Roose et al. |
| 2009/0110498 A1 | 4/2009 | Park |
| 2009/0112213 A1 | 4/2009 | Heavener et al. |
| 2009/0131941 A1 | 5/2009 | Park et al. |
| 2009/0138020 A1 | 5/2009 | Park et al. |
| 2009/0151736 A1 | 6/2009 | Belcher et al. |
| 2009/0157083 A1 | 6/2009 | Park et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0234217 A1 | 9/2009 | Mire et al. |
| 2009/0248044 A1 | 10/2009 | Amiot et al. |
| 2009/0254093 A1 | 10/2009 | White et al. |
| 2009/0254367 A1 | 10/2009 | Belcher et al. |
| 2009/0270868 A1 | 10/2009 | Park et al. |
| 2009/0306676 A1 | 12/2009 | Lang et al. |
| 2009/0307893 A1 | 12/2009 | Burdulis, Jr. et al. |
| 2009/0312805 A1 | 12/2009 | Lang et al. |
| 2010/0023015 A1 | 1/2010 | Park |
| 2010/0042105 A1 | 2/2010 | Park et al. |
| 2010/0049195 A1 | 2/2010 | Park et al. |
| 2010/0152741 A1 | 6/2010 | Park et al. |
| 2010/0256479 A1 | 10/2010 | Park et al. |
| 2010/0298894 A1 | 11/2010 | Bojarski et al. |
| 2011/0282473 A1 | 11/2011 | Pavlovskaia et al. |
| 2012/0192401 A1 | 8/2012 | Pavlovskaia et al. |

FOREIGN PATENT DOCUMENTS

| | | |
|---|---|---|
| DE | 4341367 C1 | 6/1995 |
| DE | 102005023028 A1 | 11/2006 |
| EP | 0097001 A | 12/1983 |
| EP | 0574098 A | 12/1993 |
| EP | 0622052 A | 11/1994 |
| EP | 0908836 A2 | 4/1999 |
| EP | 0908836 A3 | 12/1999 |
| EP | 1486900 A1 | 12/2004 |
| EP | 1532939 A1 | 5/2005 |
| GB | 2215610 A1 | 9/1989 |
| GB | 2420717 A | 6/2006 |
| WO | WO 93/25157 A1 | 12/1993 |
| WO | WO 95/07509 A1 | 3/1995 |
| WO | WO 97/23172 A2 | 7/1997 |
| WO | WO 98/12995 A2 | 4/1998 |
| WO | WO 01/00096 A1 | 1/2001 |
| WO | WO 01/70142 A1 | 9/2001 |
| WO | WO 02/096268 A2 | 12/2002 |
| WO | WO 2004/032806 A1 | 4/2004 |
| WO | WO 2004/049981 A2 | 6/2004 |
| WO | WO 2005/051240 A1 | 6/2005 |
| WO | WO 2005/087125 A2 | 9/2005 |
| WO | WO 2006/058057 A2 | 6/2006 |
| WO | WO 2006/060795 A1 | 6/2006 |
| WO | WO 2006/092600 A1 | 9/2006 |
| WO | WO 2006/134345 A1 | 12/2006 |
| WO | WO 2007/014164 A2 | 2/2007 |
| WO | WO 2007/058632 A1 | 5/2007 |
| WO | WO 2007/092841 A2 | 8/2007 |

OTHER PUBLICATIONS

U.S. Appl. No. 29/296,687, filed Oct. 25, 2007, Park.
U.S. Appl. No. 12/111,924, filed Apr. 29, 2008, Park et al.
U.S. Appl. No. 12/390,667, filed Feb. 23, 2009, Park et al.
U.S. Appl. No. 12/391,008, filed Feb. 23, 2009, Park et al.
U.S. Appl. No. 12/505,056, filed Jul. 17, 2009, Park.
Advisory Action, U.S. Appl. No. 11/642,385, dated Oct. 29, 2010, 3 pages.
Amendment and Response to Ex Parts Quayle Action, U.S. Appl. No. 29/296,687 dated Mar. 24, 2011, 17 pages.
Amendment and Response to Final Office Action, U.S. Appl. No. 11/642,385, filed Oct. 4, 2010, 16 pages.
Amendment and Response to Non-Final Office Action, U.S. Appl. No. 11/641,382, dated Apr. 20, 2010, 23 pages.
Amendment and Response to Non-Final Office Action, U.S. Appl. No. 11/959,344, dated Jul. 15, 2011, 13 pages.
Amendment and Response to Office Action, U.S. Appl. No. 11/656,323, filed Jun. 25, 2010, 7 pages.
Amendment and Response to Office Action, U.S. Appl. No. 11/641,569, dated Feb. 5, 2010, 20 pages.

Amendment and Response to Restriction Requirement, U.S. Appl. No. 11/641,569, dated May 27, 2009, 12 pages.
Amendment and Response to Restriction Requirement, U.S. Appl. No. 11/641,382, dated Oct. 5, 2009, 10 pages.
Amendment and Response to Restriction Requirement, U.S. Appl. No. 11/642,385, filed Nov. 24, 2009, 10 pages.
Amendment and Response to Restriction/Election Requirement, U.S. Appl. No. 11/656,323, filed Dec. 8, 2009, 6 pages.
Amendment and Response, U.S. Appl. No. 11/642,385, filed May 28, 2010, 11 pages.
European Search Report, 10192631.9-2310, dated Mar. 17, 2011, 5 pages.
Ex Parte Quayle Action, U.S. Appl. No. 29/296,687, mailed Jan. 24, 2011, 11 pages.
Final Office Action, and PTO-892, U.S. Appl. No. 11/641,382, mailed Aug. 5, 2010, 13 pages.
Final Office Action, and PTO-892, U.S. Appl. No. 11/656,323, mailed Sep. 3, 2010, 11 pages.
Final Office Action, U.S. Appl. No. 11/641,669, mailed May 10, 2010, 9 pages.
International Search Report and Written Opinion, International Application No. PCT/US2009/058946, mailed Jan. 28, 2010, 14 pages.
International Search Report and Written Opinion, International Application No. PCT/US2009/068055, mailed Mar. 11, 2010, 10 pages.
International Search Report and Written Opinion, PCT/US2011/032342, dated Jul. 1, 2011, 8 pages.
Non-Final Office Action, and PTO-892, U.S. Appl. No. 11/641,382, mailed Jan. 20, 2010, 12 pages.
NonFinal Office Action, and PTO-892, U.S. Appl. No. 11/642,385, mailed Mar. 2, 2010, 11 pages.
Non-Final Office Action, and PTO-892, U.S. Appl. No. 11/656,323, mailed Mar. 30, 2010, 10 pages.
Nonfinal Office Action, U.S. Appl. No. 11/959,344, dated Feb. 15, 2011, 29 pages.
Notice of Allowance, U.S. Appl. No. 29/296,687, mailed Mar. 31, 2011, 18 pages.
Notice of Non-Compliant Amendment, U.S. Appl. No. 11/641,569, mailed Aug. 7, 2009, 3 pages.
Preliminary Amendment, U.S. Appl. No. 11/641,569, dated Aug. 14, 2008, 13 pages.
Preliminary Amendment, U.S. Appl. No. 11/642,385, filed Aug. 22, 2008, 42 pages.
RCE/Amendment, U.S. Appl. No. 11/641,569, filed Aug. 9, 2010, 18 pages.
RCE/Amendment, U.S. Appl. No. 11/642,382, filed Oct. 26, 2010, 14 pages.
RCE/Amendment, U.S. Appl. No. 11/642,385, filed Dec. 6, 2010, 13 pages.
RCE/Amendment, U.S. Appl. No. 11/656,323, filed Nov. 19, 2010, 12 pages.
Response to Notice of Non-Complaint Amendment, U.S. Appl. No. 11/641,569, dated Aug. 19, 2009, 11 pages.
Response to Restriction Requirement U.S. Appl. No. 29/296,687, filed Oct. 7, 2010, 3 pages.
Response to Restriction Requirement, U.S. Appl. No. 11/956,344, filed Nov. 24, 2010, 13 pages.
Response to Restriction Requirement, U.S. Appl. No. 12/390,667, dated Jul. 27, 2011, 8 pages.
Restriction Requirement, U.S. Appl. No. 11/959,344, dated Oct. 29, 2010, 6 pages.
Restriction Requirement, U.S. Appl. No. 29/296,687, mailed Sep. 21, 2010, 7 pages.
Restriction Requirement, U.S. Appl. No. 12/390,667, dated Jul. 14, 2011, 9 pages.
Akca, "Matching of 3D Surfaces and Their Intensities," ISPRS Journal of Photogrammetry & Remote Sensing, 62(2007), 112-121.
Arima et al., "Femoral Rotational Alignment, Based on the Anteroposterior Axis, in Total Knee Arthroplasty in a Valgus Knee. A Technical Note," Journal Bone Joint Surg Am. 1995:77(9):1331-4.
Bargar et al., "Robotic Systems in Surgery," Orthopedic and Spine Surgery, Surgical Technology International II, 1993, 419-423.

Besl et al., "A Method for Registration of 3-D Shapes," IEEE Transactions on Pattern Analysis and Machine Intelligence (PAMI), 14(2):239-256, Feb. 1992.
Blaha et al., "Using the Transepicondylar Axis to Define the Sagittal Morphology of the Distal Part of the Femur," J Bone Joint Surg Am. 2002;84-A Suppl 2:48-55.
Bullough et al., "The Geometry of Diarthrodial Joints, Its Physiologic Maintenance and the Possible significance of Age-Related Changes in Geometry-to-Load distribution and the Development of Osteoarthritis," Clin Orthop Rel Res 1981, 156:61-6.
Burgkart et al., "Magnetic Resonance Imaging-Based Assessment of Cartilage Loss in Severe Osteoarthritis: Accuracy, Precision, and Diagnostic Value," Arthritis Rheum 2001, 44:2072-7.
Canny, "A computational Approach to Edge Detection," IEEE Transactions on Pattern Analysis and Machine Intelligence, PAMI 8(6), pp. 679-698 (1986).
Churchill et al., "The Transepicondylar Axis Approximates the Optimal Flexion Axis of the Knee," Clin Orthop Relat Res, 1998(356):111-8.
Cicuttini et al., "Gender Differences in Knee Cartilage Volume as Measured by Magnetic Resonance Imaging," Osteoarthritis Cartilage 1999, 7:265-71.
Cicuttini et al., "Longitudinal Study of the Relationship Between Knee angle and Tibiofemoral cartilage Volume in Subjects with Knee Osteoarthritis," Rheumatology (Oxford) 2004, 43:321-4.
Eckhoff et al., "Difference Between the Epicondylar and Cylindrical Axis of the Knee," Clin Orthop Relat Res. 2007;461:238-44.
Eisenhart-Rothe et al., "Femorotibial and Patellar Cartilage Loss in Patients Prior to Total Knee arthroplasty, Heterogeneity, and Correlation with alignment of the Knee," Ann Rheum Dis., Jun. 2005 (BMJ Publishing Group Ltd & European League Against Rheumatism).
Eisenhart-Rothe et al, "The Role of Knee alignment in Disease Progression and Functional Decline in Knee Osteoarthritis," JAMA 2001, 286:188-95.
Elias et al., "A Correlative Study of the Geometry and anatomy of the Distal Femur," Clin orthop Relat Res, 1990(260):98-103.
Favorito et al., "total Knee Arthroplasty in the Valgus Knee," Journal Am Aced Orthop surg. 2002;10(1):16-24.
Freeman et al., "The Movement of the Knee Studied by Magnetic Resonance Imaging," Clinical orthop Relat Res. 2003(410):35-43.
Freeman et al., "The movement of the Normal Tibio-Femoral Joint," Journal Biomech. 2005;38(2):197-208.
Graichen et al., "quantitative Assessment of Cartilage Status in Osteoarthritis by Quantitative Magnetic Resonance Imaging: Technical Validation for Use in analysis of Cartilage Volume and Further Morphologic Parameters," Arthritis Rheum 2004, 50:811-16.
Gruen et al., "least Squares 3D Surface and Curve Matching," ISPRS Journal of Photogrammetry & Remote Sensing, 59(2005), 151-174.
Hollister et al., "The Axes of Rotation of the Knee," Clin Orthop Relat Res. 1993(290):259-68.
Howell et al., "Longitudinal Shapes of the Tibia and Femur are Unrelated and Variable," Clinical Orthopaedics and Related Research (2010) 468: 1142-1148.
Howell et al., "Results of an Initial Experience with Custom-Fit Positioning Total Knee Arthroplasty in a Series of 48 Patients," Orthopedics, 2008;31(9):857-63.
Howell et al., "In Vivo Adduction and Reverse Axial Rotation (External) of the Tibial Component can be Minimized During Standing and Kneeling," Orthopedics, In Press.
Iwaki et al., "Tibiofemoral Movement 1: The Shapes and Relative Movements of the Femur and Tibia in the Unloaded Cadaver Knee," Journal Bone Joint Surg Br. 2000;82(8):1189-95.
Jacobs et al., "Hip Resurfacing Through an Anterolateral Approach," J. Bone Joint Surg Am. 2008:90 Suppl 3:38-44.
Johnson, "Joint Remodeling as the Basis for Osteoarthritis," Journal Am Vet Med Assoc. 1962, 141:1233-41.
Kass et al., "Active Contour Models," International Journal of Computer Vision, pp. 321-331 (1988).
Kellgren et al., "Radiological Assessment of Osteoarthrosis," Ann Rheum Dis 1957, 10:494-501.
Kessler et al, "Sagittal Curvature of Total Knee Replacements Predicts in vivo Kinematics," Clin Biomech (Bristol, Avon) 2007; 22(1):52-8.

Kienzel III et al., "Total Knee Replacement," IEEE May/Jun. 1995.
Kienzel III et al., "An Integrated CAD-Robotics System for Total Knee Replacement Surgery", IEEE International Conference, pp. 889-894, vol. 1, May 1993.
Krackow et al., "Flexion-Extension Joint Gap Changes After Lateral Structure Release for Valgus Deformity Correction in Total Knee Arthroplasty: A Cadaveric Study," Journal Arthroplasty, 1999;14(8):994-1004.
Krackow et al., "Primary Total Knee Arthroplasty in Patients with Fixed Valgus Deformity," Clin Orthop Relat Res. 1991(273):9-18.
Krackow, "Approaches to Planning lower Extremity alignment for Total Knee arthroplasty and Osteotomy About the Knee," adv Orthop surg 7:69, 1983.
Lea et al., "Registration and immobilization in robot-assisted surgery", Journal of Image Guided Surgery, pp. 1-10, 1995.
Manner et al., "Knee Deformity in Congenital Longitudinal Deficiencies of the Lower Extremity," Clin Orthop Relat Res. 2006;448:185-92.
Matsuda et al., "Anatomical Analysis of the Femoral Condyle in Normal and Osteoarthritic Knees," Journal Orthopaedic Res. 2004;22(1)104-9.
Matsuda et al., "Femoral Condyle Geometry in the Normal and Varus Knee," Clinical Orthop Relat Res. 1998(349):183-8.
Messmer et al., "Volumetric Determination of the Tibia Based on 2d Radiographs Using a 2d/3d Database", Dept. of Surgery, Trauma Unit, University Hospital, Bassel, Switzerland, *Computer Aided Surgery* 6:183-194 (2001).
Mihalko et al., The Variability of Intramedullary Alignment of the Femoral Component During Total Knee Arthroplasty, Journal Arthroplasty. 2005;20(1):25-8.
Morvan et al., IVECS, Interactively Correcting .STL Files in a Virtual Environment, Clemson University, Clemson, SC, Proc. Conf. Virtual Design, Aug. 1996.
Naoki Kusumoto, Taiji et al., "Application of Virtual Reality Force Feedback Haptic Device for Oral Implant Surgery", Graduate School of Dentistry Course for Integrated Oral Science and Stomatology, Jun. 16, 2005.
Panjabi et al., "Errors in Kinematic Parameters of a Planar Joint: Guidelines for Optimal Experimental Design," Journal Biomech. 1982;15(7):537-44.
Perillo-Marcone et al., "Effect of Varus/Valgus Malalignment on Bone Strains in the Proximal Tibia After TKR: An Explicit Finite element Study," Journal Biomechanical Engineering 2007, vol. 129, 1:1-11.
Peterfy et al., "Quantification of articular Cartilage in the Knee with Pulsed Saturation Transfer Subtraction and Fact-Suppressed MR Imaging: Optimization and Validation," Radiology 1994, 192:485-91.
Pinskerova et al., "The Shapes and Relative Movements of the Femur and Tibia at the Knee," Orthopaedics 2000;29 Suppl 1:S3-5.
Rosset et al., "General Consumer Communication Tools for Improved Image Management and Communication in Medicine," Journal Digital Imaging, 2005;18(4):270-9.
Shakespeare D., "Conventional Instruments in Total Knee Replacement: What Should We Do With Them?" Knee. 2006;13(1):1-6.
Shepstone et al., "The shape of the Distal Femur: A Palaeopathological Comparison of Eburnated and Non-Eburnated Femora," Ann. Rheum Dis. 1999, 58:72-8.
Siston et al., "The Variability of Femoral Rotational Alignment in Total Knee Arthroplasty," Journal Bone Joint Surg Am. 2005;87(10):2276-80.
Siston et al., "Averaging Different Alignment Axes Improves Femoral Rotational Alignment in Computer-Navigated Total Knee Arthroplasty," Journal Bone Joint Surg Am. 2008;90(10):2098-104.
Soudan et al., "'Methods, Difficulties and Inaccuracies in the Study of Human Joint Kinematics and Pathokinematics by the Instant axis Concept. Example: The Knee Joint," Journal Biomech. 1979;12(1):27-33.
Spencer et al., "Initial Experience with Custom-Fit Total Knee Replacement: Intra-operative Events and Long-Leg Coronal alignment," International Orthopaedics (SICOT), 2009:In Press.
Stulberg et al., "Computer- and Robot-Assisted Orthopaedic Surgery", Computer-Integrated Surgery Technology and Clinical Applications, edited by Taylor et al., Massachusetts Institute of Technology, Chapter 27, pp. 373-378, 1996.
Teeny et al., "Primary Total Knee Arthroplasty in Patients with Severe Varus Deformity. A Comparative Study," Clin Orthop Relat Res. 1991(273):19-31.
Wright Medical Technology, Inc., "Prophecy Pre-Operative Naviation Guides Surgical Technique," 2009.
U.S. Appl. No. 13/086,275, filed Apr. 13, 2011, Park et al.
U.S. Appl. No. 13/066,568, filed Apr. 18, 2011, Pavlovskaia et al.
U.S. Appl. No. 29/394,882, filed Jun. 22, 2011, Ilwhan Park.
U.S. Appl. No. 12/546,545, filed Aug. 24, 2009, Park et al.
U.S. Appl. No. 12/563,809, filed Sep. 21, 2009, Park et al.
Final Office Action, U.S. Appl. No. 11/959,344, mailed Oct. 27, 2011, 12 pages.
Non-Final Office Action, U.S. Appl. No. 11/641,569, dated Aug. 3, 2011, 14 pages.
Non-Final Office Action, U.S. Appl. No. 12/390,667, dated Aug. 24, 2011, 49 pages.
Non-Final Office Action, U.S. Appl. No. 11/946,002, dated Nov. 25, 2011, 44 pages.
Non-Final Office Action, U.S. Appl. No. 12/391,008, mailed Oct. 31, 2011, 44 pages.
Notice of Allowance, U.S. Appl. No. 13/066,568, mailed Oct. 26, 2011, 28 pages.
Response to Non-Final Office Action, U.S. Appl. No. 12/390,667, filed Nov. 18, 2011, 16 pages.
Response to Non-Final Office Action, U.S. Appl. No. 11/641,569, filed Dec. 2, 2011, 7 pages.
Response to Restriction Requirement, U.S. Appl. No. 12/391,008, filed Aug. 29, 2011, 9 pages.
Response to Restriction, U.S. Appl. No. 11/924,425, filed Nov. 8, 2011, 5 pages.
Response to Restriction, U.S. Appl. No. 11/946,002, filed Sep. 23, 2011, 7 pages.
Restriction Requirement, U.S. Appl. No. 11/924,425, dated Oct. 13, 2011, 6 pages.
Restriction Requirement, U.S. Appl. No. 11/946,002, dated Sep. 1, 2011, 8 pages.
Restriction Requirement, U.S. Appl. No. 12/391,008, dated Aug. 18, 2011, 6 pages.
International Search Report and Written Opinion, PCT/US2007/001624, dated Dec. 12, 2007, 14 pages.
Invitation to Pay Additional Fees mailed on Jul. 31, 2007, for PCT Application No. PCT/US2007/001624 filed on Jan. 19, 2007, 5 pages.
International Search Report and Written Opinion, PCT/US2007/001622, dated Jun. 11, 2007, 14 pages.
Office Action, U.S. Appl. No. 10/146,862, mailed Jan. 13, 2005, 10 pages.
Amendment and Response to Office Action and Petition to Revive, U.S. Appl. No. 10/146,862, filed Jan. 18, 2006, 29 pages.
Restriction Requirement, U.S. Appl. No. 11/641,569, mailed Apr. 27, 2009, 7 pages.
International Search Report and Written Opinion, PCT/US2008/083125, dated Mar. 9, 2009, 13 pages.
International Search Report and Written Opinion, International Application No. PCT/US2009/34983, mailed May 22, 2009, 15 pages.
International Search Report and Written Opinion, International Application No. PCT/US2009/034967, mailed Jun. 16, 2009, 15 pages.
International Search Report and Written Opinion, International Application No. PCT/US2009/041519, mailed Jun. 17, 2009, 10 pages.
Akenine-Möller et al., Real-Time Rendering, Second Edition, AK Peters, Natick, MA, 6 pages (Table of Contents), 2002.
Author Unknown, "MRI Protocol Reference," ConforMIS, Inc., copyright 2007, http://www.conformis.com/Imaging-Professionals/MRI-Protocol-Guides, last visited on Mar. 28, 2008, 18 pages.
Author Unknown, "MRI Protocol Reference Guide for GE Systems," ConforMIS, Inc., copyright 2007, http://www.conformis.com/Imaging-Professionals/MRI-Protocol-Guides, last visited on Mar. 28, 2008, 18 pages.

Author Unknown, "MRI Protocol Reference Guide for Phillips Systems," ConforMIS, Inc., copyright 2007, http://www.conformis.com/Imaging-Professionals/MRI-Protocol-Guides, last visited on Mar. 28, 2008, 19 pages.

Author Unknown, "MRI Protocol Reference Guide for Siemens Systems," ConforMIS, Inc., copyright 2007, http://www.conformis.com/Imaging-Professionals/MRI-Protocol-Guides, last visited on Mar. 28, 2008, 18 pages.

Barequet et al., "Filling Gaps in the Boundary of a Polyhedron," Computer Aided Geometric Design, vol. 12, pp. 207-229, 1995.

Barequet et al., "Repairing CAD Models," Proceedings of the 8th IEEE Visualization '97 Conference, pp. 363-370, Oct. 1997.

Berry et al., "Personalised image-based templates for intra-operative guidance," Proc. Inst. Mech. Eng. Part H: J. Engineering in Medicine, vol. 219, pp. 111-118, Oct. 7, 2004.

Biščević et al., "Variations of Femoral Condyle Shape," Coll. Antropol., vol. 29 No. 2, pp. 409-414, 2005.

Blinn, Jim Blinn's Corner—A Trip Down the Graphics Pipeline, Morgan Kaufmann Publishers, Inc., San Francisco, CA, 5 pages (Table of Contents), 1996.

Bøhn et al., "A Topology-Based Approach for Shell-Closure," Geometric Modeling for Product Realization (P.R. Wilson et al. editors), pp. 297-319, Elsevier Science Publishers B.V., North-Holland, 1993.

Chauhan et al., "Computer-assisted knee arthroplasty versus a conventional jig-based technique—a randomised, prospective trial," The Journal of Bone and Joint Surgery, vol. 86-B, No. 3, pp. 372-377, Apr. 2004.

Cohen et al., Radiosity and Realistic Image Synthesis, Academic Press Professional, Cambridge, MA, 8 pages (Table of Contents), 1993.

Couglin et al., "Tibial Axis and Patellar Position Relative to the Femoral Epicondylar Axis During Squatting," The Journal of Arthroplasty, vol. 18, No. 8, Elsevier, 2003.

Delp et al., "Computer Assisted Knee Replacement," Clinical Orthopaedics and Related Research, No. 354, pp. 49-56, Sep. 1998.

Dutré et al., Advanced Global Illumination, AK Peters, Natick, MA, 5 pages (Table of Contents), 2003.

Eckhoff et al., "Three-Dimensional Mechanics, Kinematics, and Morphology of the Knee Viewed in Virtual Realty," The Journal of Bone and Joint Surgery, vol. 87-A, Supplement 2, pp. 71-80, 2005.

Erikson, "Error Correction of a Large Architectural Model: The Henderson County Courthouse," Technical Report TR95-013, Dept. of Computer Science, University of North Carolina at Chapel Hill, pp. 1-11, 1995.

Ervin et al., Landscape Modeling, McGraw-Hill, New York, NY, 8 pages (Table of Contents), 2001.

Farin, Nurb Curves and Surfaces: From Projective Geometry to Practical Use, AK Peters, Wellesley, MA, 7 pages (Table of Contents), 1995.

Fleischer et al., "Accurate Polygon Scan Conversion Using Half-Open Intervals," Graphics Gems III, pp. 362-365, code: pp. 599-605, 1992.

Foley et al., Computer Graphics: Principles and Practice, Addison-Wesley Publishing Company, Reading, MA, 9 pages (Table of Contents), 1990.

Glassner (editor), An Introduction to Ray Tracing, Academic Press Limited, San Diego, CA, 4 pages (Table of Contents), 1989.

Glassner, Principles of Digital Image Synthesis, Volumes One and Two, Morgan Kaufmann Publishers, Inc., San Francisco, CA, 32 pages (Table of Contents), 1995.

Gooch et al., Non-Photorealistic Rendering, AK Peters, Natick, MA, 4 pages (Table of Contents), 2001.

Grüne et al., "On numerical algorithm and interactive visualization for optimal control problems," Journal of Computation and Visualization in Science, vol. 1, No. 4, pp. 221-229, Jul. 1999.

Guéziec et al., "Converting Sets of Polygons to Manifold Surfaces by Cutting and Stitching," Proc. IEEE Visualization 1998, pp. 383-390, Oct. 1998.

Hafez et al., "Patient Specific Instrumentation for TKA: Testing the Reliability Using a Navigational System," MIS Meets CAOS Symposium & Instructional Academy, Less and Minimally Invasive Surgery for Joint Arthroplasty: FACT and FICTION Syllabus, San Diego, CA, 8 pages, Oct. 20-22, 2005 (best available copy).

Hafez et al., "Computer Assisted Total Knee Replacement: Could a Two-Piece Custom Template Replace the Complex Conventional Instrumentations?", Computer Aided Surgery, vol. 9, No. 3, pp. 93-94, 2004.

Hafez et al., "Computer-Assisted Total Knee Arthroplasty Using Patient-Specific Templating," Clinical Orthopaedics and Related Research, No. 0, pp. 1-9, 2006.

Jensen, Realistic Image Synthesis Using Photon Mapping, AK Peters, Natick, MA, 7 pages (Table of Contents), 2001.

Jones et al., "A new approach to the construction of surfaces from contour data," Computer Graphics Forum, vol. 13, No. 3, pp. 75-84, 1994 [ISSN 0167-7055].

Khorramabadi, "A Walk Through the Planned CS Building," Technical Report UCB/CSD 91/652, Computer Science Department, University of California at Berkeley, 74 pages, 1991.

Kidder et al., "3-D Model Acquisition, Design, Planning and Manufacturing of Orthopaedic Devices: A Framework," Advanced Sensor and Control-System Interface (B.O. Nnaji editor), Proceedings SPIE—The International Society for Optical Engineering, Bellingham, WA, vol. 2911, pp. 9-22, Nov. 21-22, 1996.

Kumar, Robust Incremental Polygon Triangulation for Surface Rendering, Center for Geometric Computing, Department of Computer Science, Johns Hopkins University, Baltimore, MD, WSCG, The International Conference in Central Europe on Computer Graphics, Visualization and Computer Vision, pp. 381-388, 2000.

Kunz et al., "Computer Assisted Hip Resurfacing Using Individualized Drill Templates," The Journal of Arthroplasty, vol. 00, No. 0, pp. 1-7, 2009.

Lorensen et al., "Marching Cubes: A High Resolution 3d Surface Construction Algorithm," Computer Graphics, vol. 21, No. 4, pp. 163-169, 1987.

Nooruddin et al., Simplification and Repair of Polygonal Models Using Volumetric Techniques, IEEE Transactions on Visualization and Computer Graphics, vol. 9, No. 2, pp. 191-205, Apr.-Jun. 2003.

Pharr et al., Physically Based Rendering, from Theory to Implementation, Morgan Kaufmann Publishers, San Francisco, CA, 13 pages (Table of Contents), 2004.

Platt et al., "Mould Arthroplasty of the Knee, A Ten-Year Follow-up Study," The Journal of Bone and Joint Surgery (British Volume), vol. 51-B, No. 1, pp. 76-87, Feb. 1969.

Potter, "Arthroplasty of the Knee with Tibial Metallic Implants of the McKeever and MacIntosh Design," The Surgical Clinics of North America, vol. 49, No. 4, pp. 903-915, Aug. 1969.

Radermacher et al., "Computer Assisted Orthopaedic Surgery with Image Based Individual Templates," Clinical Orthopaedics and Related Research, vol. 354, pp. 28-38, Sep. 1998.

Rohlfing et al., "Quo Vadis, Atlas-Based Segmentation?", The Handbook of Medical Image Analysis: Segmentation and Registration Models (Kluwer), pp. 1-55, (http://www.stanford.edu/~rohlfing/publications/2005-rohlfing-chapter-quo_vadis_atlas_based_segmentation.pdf).

Shirley et al., Realistic Ray Tracing, Second Edition, AK Peters, Natick, MA, 7 pages (Table of Contents), 2003.

Strothotte et al., Non-Photorealistic Computer Graphics—Modeling, Rendering, and Animation, Morgan Kaufmann Publishers, San Francisco, CA, 9 pages (Table of Contents), 2002.

Vande Berg et al., "Assessment of Knee Cartilage in Cadavers with Dual-Detector Spiral CT Arthrography and MR Imaging," Radiology, vol. 222, No. 2, pp. 430-436, Feb. 2002.

Wikipedia, the Free Encyclopedia, "CNC," (date unknown) located at http://en.wikipedia.org/wiki/CNC>, 6 pages, last visited on Apr. 12, 2007.

International Search Report and Written Opinion, International Application No. PCT/US2009/040629, mailed Aug. 6, 2009, 9 pages.

Restriction Requirement, U.S. Appl. No. 11/641,382, mailed Sep. 3, 2009, 6 pages.

Restriction Requirement, U.S. Appl. No. 11/642,385, mailed Oct. 27, 2009, 7 pages.

International Search Report and Written Opinion, International Application No. PCT/US2009/051109, mailed Nov. 6, 2009, 13 pages.

NonFinal Office Action, U.S. Appl. No. 11/641,569, mailed Nov. 12, 2009, 9 pages.

Restriction Requirement, U.S. Appl. No. 11/656,323, mailed Nov. 13, 2009, 10 pages.
Advisory Action and Interview Summary, U.S. Appl. No. 12/390,667, mailed Apr. 24, 2012, 23 pages.
Final Office Action, U.S. Appl. No. 12/390,667, mailed Jan. 13, 2012, 27 pages.
Final Office Action, U.S. Appl. No. 11/641,569, mailed Mar. 1, 2012, 12 pages.
Final Office Action, U.S. Appl. No. 11/946,002, mailed May 9, 2012, 24 pages.
Final Office Action, U.S. Appl. No. 12/391,008, mailed May 17, 2012, 28 pages.
Non-Final Office Action, U.S. Appl. No. 11/924,425, mailed Jan. 25, 2012, 35 pages.
Non-Final Office Action, U.S. Appl. No. 11/641,382, mailed Mar. 29, 2012, 24 pages.
Notice of Allowance, U.S. Appl. No. 11/959,344, mailed Mar. 5, 2012, 13 pages.
Office Action (Restriction Requirement), U.S. Appl. No. 12/563,809, dated Feb. 2, 2012, 7 pages.
Response to Final Office Action, U.S. Appl. No. 11/959,344, filed Dec. 27, 2011, 16 pages.
Response to Final Office Action, U.S. Appl. No. 12/390,667, filed Mar. 12, 2012, 19 pages.
Response to Non-Final Office Action, U.S. Appl. No. 12/391,008, filed Feb. 24, 2012, 18 pages.
Response to Non-Final Office Action, U.S. Appl. No. 11/946,002, filed Mar. 8, 2012, 16 pages.
Response to Non-Final Office Action, U.S. Appl. No. 11/924,425, filed Apr. 25, 2012, 8 pages.
Response to Restriction Requirement, U.S. Appl. No. 12/563,809, filed Feb. 24, 2012, 10 pages.
Response to Restriction Requirement, U.S. Appl. No. 12/111,924, filed Apr. 16, 2012, 8 pages.
Response to Restriction Requirement, U.S. Appl. No. 12/636,939, filed Apr. 19, 2012, 6 pages.
Response to Restriction, U.S. Appl. No. 12/505,056, filed Apr. 11, 2012, 9 pages.
Response to Restriction, U.S. Appl. No. 12/546,545, filed Jun. 4, 2012, 7 pages.
Restriction Requirement, U.S. Appl. No. 12/111,924, mailed Mar. 19, 2012, 8 pages.
Restriction Requirement, U.S. Appl. No. 12/505,056, mailed Mar. 14, 2012, 8 pages.
Restriction Requirement, U.S. Appl. No. 12/546,545, mailed May 3, 2012, 8 pages.
Restriction Requirement, U.S. Appl. No. 12/636,939, mailed Apr. 13, 2012, 6 pages.
U.S. Appl. No. 13/374,960, filed Jan. 25, 2012, Pavlovskaia et al.
Appeal Brief, U.S. Appl. No. 12/390,667, filed Jul. 12, 2012, 32 pages.
Final Office Action, U.S. Appl. No. 11/641,382, mailed Jul. 25, 2012, 12 pages.
Final Office Action, U.S. Appl. No. 11/924,425, mailed Jul. 6, 2012, 14 pages.
Non-Final Office Action, U.S. Appl. No. 12/111,924, mailed Jun. 29, 2012, 35 pages.
Non-Final Office Action, U.S. Appl. No. 12/546,545, mailed Jul. 19, 2012, 28 pages.
Non-Final Office Action, U.S. Appl. No. 12/636,939, mailed Jul. 20, 2012, 25 pages.
Non-Final Office Action, U.S. Appl. No. 13/374,960, mailed Aug. 1, 2012, 6 pages.
Response to Final Office Action, U.S. Appl. No. 11/641,569, filed Jun. 28, 2012, 10 pages.
Response to Non-Final Office Action, U.S. Appl. No. 11/641,382, filed Jun. 27, 2012, 12 pages.
Response to Restriction, U.S. Appl. No. 12/563,809, filed Aug. 6, 2012, 10 pages.
Restriction Requirement, U.S. Appl. No. 12/563,809, mailed Jul. 6, 2012, 6 pages.
U.S. Appl. No. 13/488,505, filed Jun. 5, 2012, Ilwhan Park et al.

* cited by examiner

SYSTEM AND METHOD FOR IMAGE SEGMENTATION IN GENERATING COMPUTER MODELS OF A JOINT TO UNDERGO ARTHROPLASTY

CROSS REFERENCE TO RELATED APPLICATION

This application claims the benefit under 35 U.S.C. §119(e) of U.S. Provisional Patent Application No. 61/126,102, entitled "System and Method For Image Segmentation in Generating Computer Models of a Joint to Undergo Arthroplasty" filed on Apr. 30, 2008, which is hereby incorporated by reference herein in its entirety.

FIELD OF THE INVENTION

The present invention relates to image segmentation. More specifically, the present invention relates to image segmentation in generating computer models of a joint to undergo arthroplasty, wherein the computer models may be used in the design and manufacture of arthroplasty jigs.

BACKGROUND OF THE INVENTION

Over time and through repeated use, bones and joints can become damaged or worn. For example, repetitive strain on bones and joints (e.g., through athletic activity), traumatic events, and certain diseases (e.g., arthritis) can cause cartilage in joint areas, which normally provides a cushioning effect, to wear down. Cartilage wearing down can result in fluid accumulating in the joint areas, pain, stiffness, and decreased mobility.

Arthroplasty procedures can be used to repair damaged joints. During a typical arthroplasty procedure, an arthritic or otherwise dysfunctional joint can be remodeled or realigned, or an implant can be implanted into the damaged region. Arthroplasty procedures may take place in any of a number of different regions of the body, such as a knee, a hip, a shoulder, or an elbow.

One type of arthroplasty procedure is a total knee arthroplasty ("TKA"), in which a damaged knee joint is replaced with prosthetic implants. The knee joint may have been damaged by, for example, arthritis (e.g., severe osteoarthritis or degenerative arthritis), trauma, or a rare destructive joint disease. During a TKA procedure, a damaged portion in the distal region of the femur may be removed and replaced with a metal shell, and a damaged portion in the proximal region of the tibia may be removed and replaced with a channeled piece of plastic having a metal stem. In some TKA procedures, a plastic button may also be added under the surface of the patella, depending on the condition of the patella.

Implants that are implanted into a damaged region may provide support and structure to the damaged region, and may help to restore the damaged region, thereby enhancing its functionality. Prior to implantation of an implant in a damaged region, the damaged region may be prepared to receive the implant. For example, in a knee arthroplasty procedure, one or more of the bones in the knee area, such as the femur and/or the tibia, may be treated (e.g., cut, drilled, reamed, and/or resurfaced) to provide one or more surfaces that can align with the implant and thereby accommodate the implant.

Accuracy in implant alignment is an important factor to the success of a TKA procedure. A one- to two-millimeter translational misalignment, or a one- to two-degree rotational misalignment, may result in imbalanced ligaments, and may thereby significantly affect the outcome of the TKA procedure. For example, implant misalignment may result in intolerable post-surgery pain, and also may prevent the patient from having full leg extension and stable leg flexion.

To achieve accurate implant alignment, prior to treating (e.g., cutting, drilling, reaming, and/or resurfacing) any regions of a bone, it is important to correctly determine the location at which the treatment will take place and how the treatment will be oriented. In some methods, an arthroplasty jig may be used to accurately position and orient a finishing instrument, such as a cutting, drilling, reaming, or resurfacing instrument on the regions of the bone. The arthroplasty jig may, for example, include one or more apertures and/or slots that are configured to accept such an instrument.

A system and method has been developed for producing customized arthroplasty jigs configured to allow a surgeon to accurately and quickly perform an arthroplasty procedure that restores the pre-deterioration alignment of the joint, thereby improving the success rate of such procedures. Specifically, the customized arthroplasty jigs are indexed such that they matingly receive the regions of the bone to be subjected to a treatment (e.g., cutting, drilling, reaming, and/or resurfacing). The customized arthroplasty jigs are also indexed to provide the proper location and orientation of the treatment relative to the regions of the bone. The indexing aspect of the customized arthroplasty jigs allows the treatment of the bone regions to be done quickly and with a high degree of accuracy that will allow the implants to restore the patient's joint to a generally pre-deteriorated state. However, the system and method for generating the customized jigs often relies on a human to "eyeball" bone models on a computer screen to determine configurations needed for the generation of the customized jigs. This "eyeballing" or manual manipulation of the bone modes on the computer screen is inefficient and unnecessarily raises the time, manpower and costs associated with producing the customized arthroplasty jigs. Furthermore, a less manual approach may improve the accuracy of the resulting jigs.

There is a need in the art for a system and method for reducing the labor associated with generating customized arthroplasty jigs. There is also a need in the art for a system and method for increasing the accuracy of customized arthroplasty jigs.

SUMMARY

Systems and methods for image segmentation in generating computer models of a joint to undergo arthroplasty are disclosed. Some embodiments may include a method of partitioning an image of a bone into a plurality of regions, where the method of partitioning may include obtaining a plurality of volumetric image slices of the bone, generating a plurality of spline curves associated with the bone, verifying that at least one of the plurality of spline curves follow a surface of the bone, and creating a three dimensional (3D) mesh representation based upon the at least one of the plurality of spline curves.

Other embodiments may include a method of generating a representation of a model bone, where the method of generating the representation may include obtaining an image scan of the representation as a plurality of slices, segmenting each slice in the plurality into one or more segmentation curves, generating a mesh of the representation, adjusting each slice in the plurality to include areas where the contact area of the bone is stable between successive image scans, and generating anchor segmentation such that the anchor segmentation follows a boundary of the representation of the model bone.

Other embodiments may include a method of segmenting a target bone using a representation of a model bone, where the method of segmenting the target bone may include registering a segmented form of the representation to an image scan of the target bone, refining the registration of the segmented form of the representation near a boundary of the target bone, generating a mesh from the segmented form of the representation, and generating a plurality of spline curves that approximate the intersection of the mesh and one or more slices from the image scan of the target bone.

Other embodiments may include a method of mapping a representation of a model bone into an image scan of a target bone, where the method of mapping may include registering a generated portion of the representation into the image scan of the target bone using a translational transformation, registering the generated portion of the representation into the image scan of the target bone using a similarity transformation, registering a boundary portion of the representation into the image scan of the target bone using an affine transformation, and registering the boundary portion of the representation into the image scan of the target bone using a spline transformation.

Other embodiments may include a method for determining a degree of correspondence between an image of a target bone and a representation of a model bone, where the method of determining correspondence may include selecting a plurality of sample points in the representation of the model bone to be registered, partitioning the plurality of sample points into a plurality of groups, sampling the image of the target bone, determining a correlation of voxel intensities between the image of the target bone and the representation of the model bone for each group in the plurality, and averaging the correlation determined for each group in the plurality.

Other embodiments may include a method for refining registration of a representation of a model bone to a target bone, where the method of refining may include transforming an anchor segmentation mesh, generating a plurality of random points around the transformed anchor segmentation mesh, determining if each point in the plurality lies inside one or more of the following meshes: InDark-OutLight, InLight-OutDark, or Dark-In-Light, determining whether one or more of the plurality of points lie within a threshold distance of the surface of the transformed anchor segmentation mesh, and adding each point in the plurality as a dark point or light point depending upon whether the point lies within the InDark-OutLight, InLight-OutDark, or Dark-In-Light meshes.

Still other embodiments may include a method for generating spline curves outlining the surface of a feature of interest of a target bone, where the method of generating spline curves may include intersecting a 3D mesh model of the feature surface with one or more slices of target data (the intersection defining a polyline curve), paramaterizing the polyline curve as a function of length and tangent variation, calculating a weighted sum of the length and tangent paramaterizations, and sampling the polyline using the results of the act of calculating.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

The patent or application file contains at least one drawing executed in color. Copies of this patent or patent application publication with color drawing(s) will be provided by the Office upon request and payment of necessary fee.

DETAILED DESCRIPTION

Figure 1A:
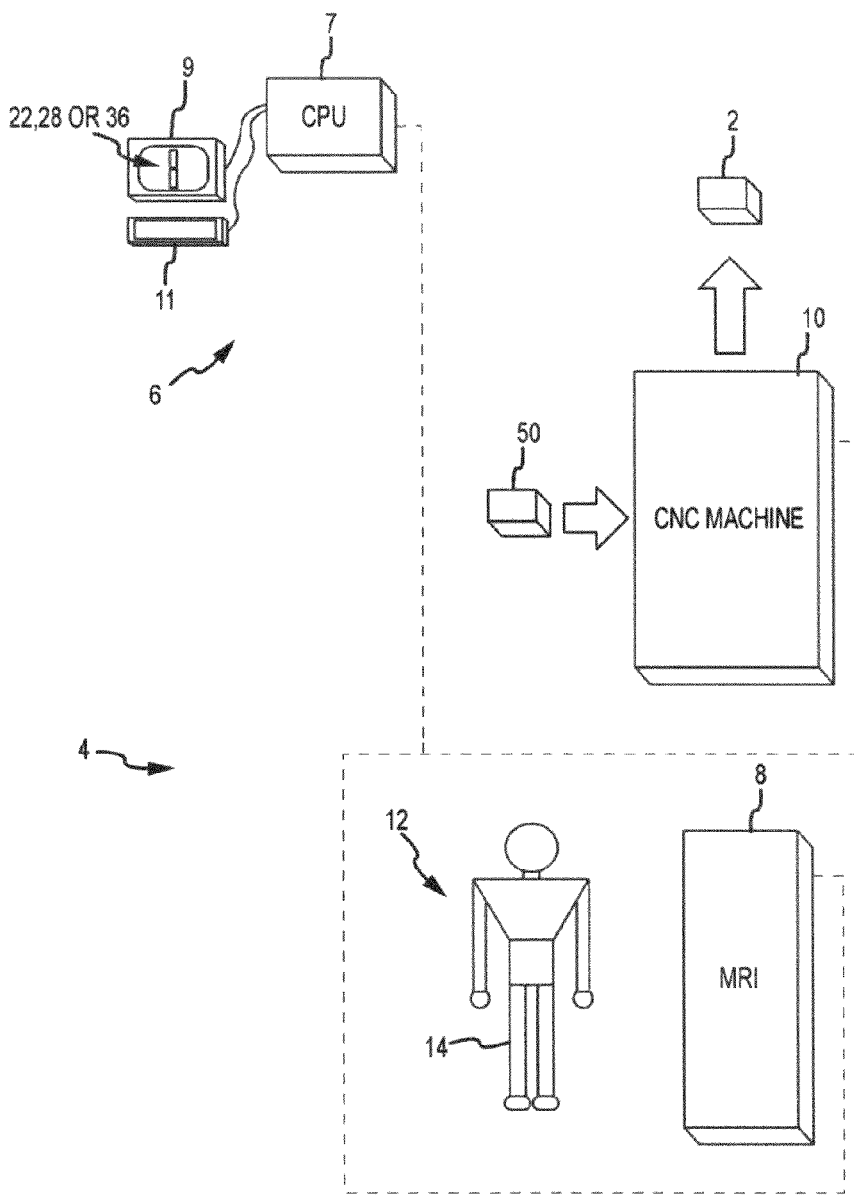
FIG. 1A is a schematic diagram of a system for employing the automated jig production method disclosed herein.

Disclosed herein are customized arthroplasty jigs 2 and systems 4 for, and methods of, producing such jigs 2. The jigs 2 are customized to fit specific bone surfaces of specific patients. Depending on the embodiment and to a greater or lesser extent, the jigs 2 are automatically planned and generated and may be similar to those disclosed in these three U.S. patent applications: U.S. patent application Ser. No. 11/656,323 to Park et al., titled "Arthroplasty Devices and Related Methods" and filed Jan. 19, 2007; U.S. patent application Ser. No. 10/146,862 to Park et al., titled "Improved Total Joint Arthroplasty System" and filed May 15, 2002; and U.S. patent Ser. No. 11/642,385 to Park et al., titled "Arthroplasty Devices and Related Methods" and filed Dec. 19, 2006. The disclosures of these three U.S. Patent Applications are incorporated by reference in their entireties into this Detailed Description.

a. Overview of System and Method for Manufacturing Customized Arthroplasty Cutting Jigs For an overview discussion of the systems 4 for, and methods of, producing the customized arthroplasty jigs 2, reference is made to FIGS. 1A-1E. FIG. 1A is a schematic diagram of a system 4 for employing the automated jig production method disclosed herein. FIGS. 1B-1E are flow chart diagrams outlining the jig production method disclosed herein. The following overview discussion can be broken down into three sections.

The first section, which is discussed with respect to FIG. 1A and [blocks 100-125] of FIGS. 1B-1E, pertains to an example method of determining, in a three-dimensional ("3D") computer model environment, saw cut and drill hole locations 30, 32 relative to 3D computer models that are termed restored bone models 28. In some embodiments, the resulting "saw cut and drill hole data" 44 is referenced to the restored bone models 28 to provide saw cuts and drill holes that will allow arthroplasty implants to restore the patient's joint to its pre-degenerated state. In other words, in some embodiments, the patient's joint may be restored to its natural alignment, whether valgus, varus or neutral.

While many of the embodiments disclosed herein are discussed with respect to allowing the arthroplasty implants to restore the patient's joint to its pre-degenerated or natural alignment state, many of the concepts disclosed herein may be applied to embodiments wherein the arthroplasty implants restore the patient's joint to a zero mechanical axis alignment such that the patient's knee joint ends up being neutral, regardless of whether the patient's predegenerated condition was varus, valgus or neutral. Accordingly, this disclosure should not be limited to methods resulting in natural alignment only, but should, where appropriate, be considered as applicable to methods resulting in zero mechanical axis.

The second section, which is discussed with respect to FIG. 1A and [blocks 100-105 and 130-145] of FIGS. 1B-1E, pertains to an example method of importing into 3D computer generated jig models 38 3D computer generated surface models 40 of arthroplasty target areas 42 of 3D computer generated arthritic models 36 of the patient's joint bones. The resulting "jig data" 46 is used to produce a jig customized to matingly receive the arthroplasty target areas of the respective bones of the patient's joint.

Figure 1B:
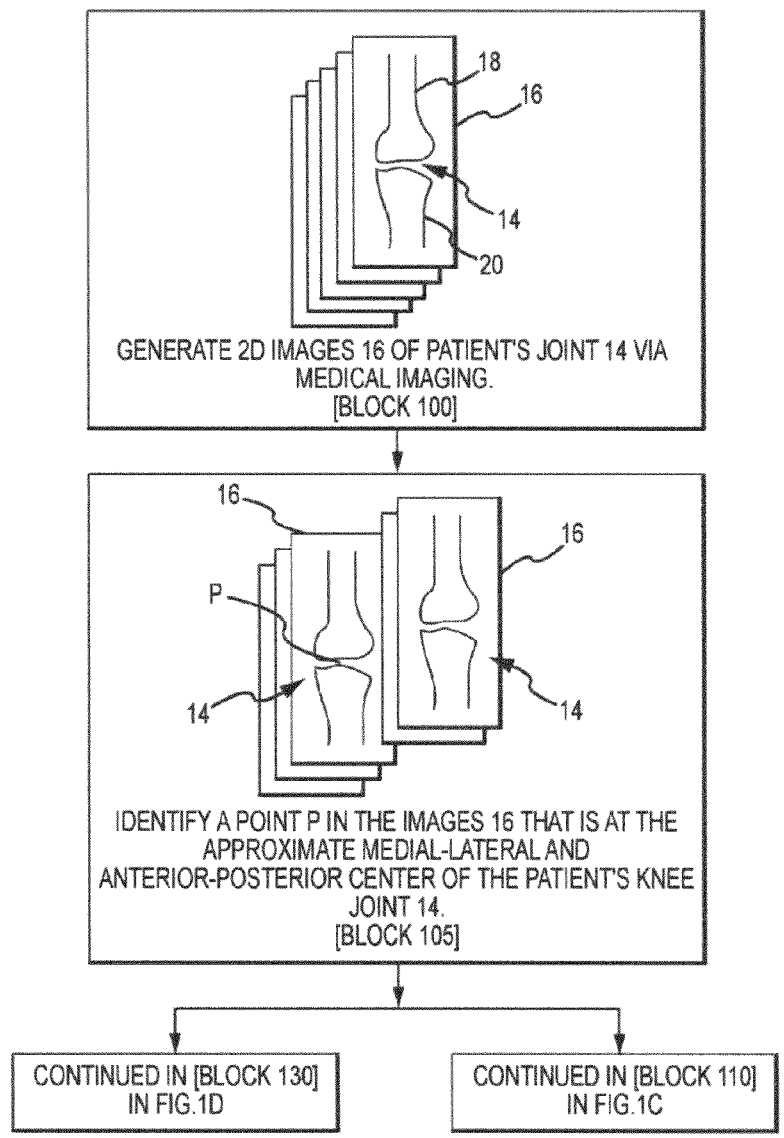
FIGS. 1B-1E are flow chart diagrams outlining the jig production method disclosed herein.
Figure 1C:
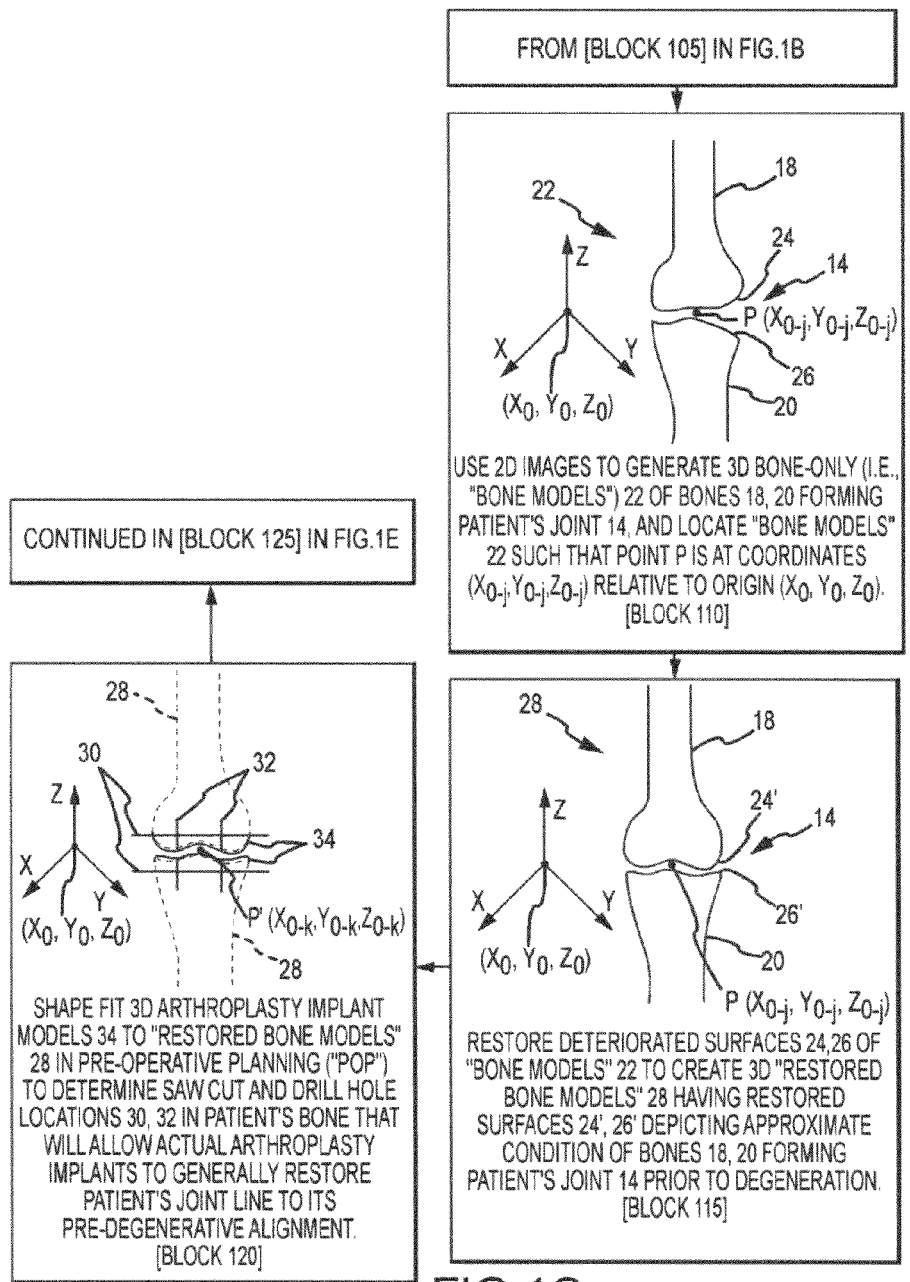
Figure 1D:
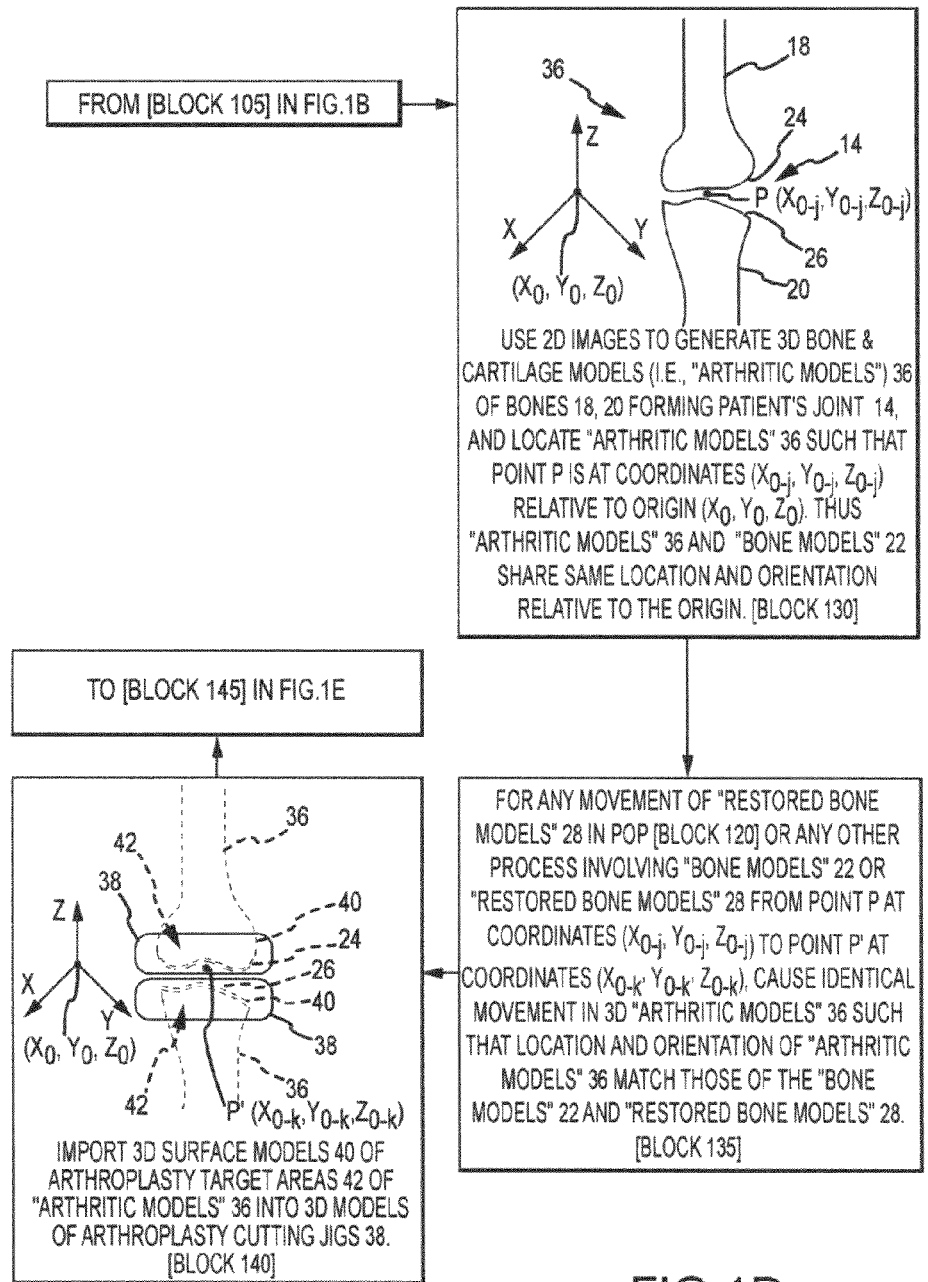
Figure 1E:
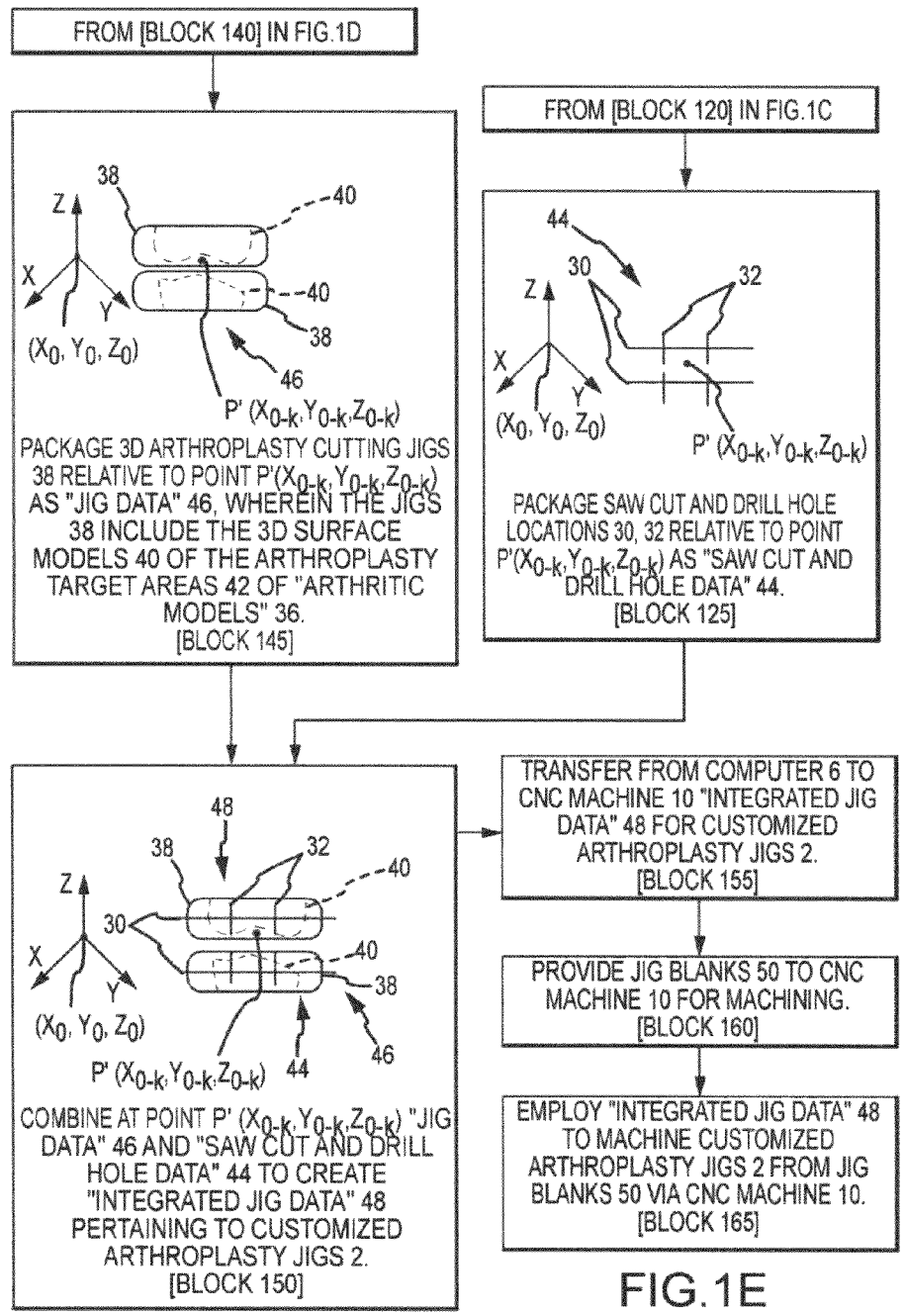

The third section, which is discussed with respect to FIG. 1A and [blocks 150-165] of FIG. 1E, pertains to a method of combining or integrating the "saw cut and drill hole data" 44 with the "jig data" 46 to result in "integrated jig data" 48. The "integrated jig data" 48 is provided to the CNC machine 10 for the production of customized arthroplasty jigs 2 from jig blanks 50 provided to the CNC machine 10. The resulting customized arthroplasty jigs 2 include saw cut slots and drill holes positioned in the jigs 2 such that when the jigs 2 matingly receive the arthroplasty target areas of the patient's bones, the cut slots and drill holes facilitate preparing the arthroplasty target areas in a manner that allows the arthroplasty joint implants to generally restore the patient's joint line to its pre-degenerated state.

As shown in FIG. 1A, the system 4 includes one or more computers 6 having a CPU 7, a monitor or screen 9 and an operator interface controls 11. The computer 6 is linked to a medical imaging system 8, such as a CT or MRI machine 8, and a computer controlled machining system 10, such as a CNC milling machine 10.

As indicated in FIG. 1A, a patient 12 has a joint 14 (e.g., a knee, elbow, ankle, wrist, hip, shoulder, skull/vertebrae or vertebrae/vertebrae interface, etc.) to be replaced. The patient 12 has the joint 14 scanned in the imaging machine 8. The imaging machine 8 makes a plurality of scans of the joint 14, wherein each scan pertains to a thin slice of the joint 14.

As can be understood from FIG. 1B, the plurality of scans is used to generate a plurality of two-dimensional ("2D")

images 16 of the joint 14 [block 100]. Where, for example, the joint 14 is a knee 14, the 2D images will be of the femur 18 and tibia 20. The imaging may be performed via CT or MRI. In one embodiment employing MRI, the imaging process may be as disclosed in U.S. patent application Ser. No. 11/946,002 to Park, which is entitled "Generating MRI Images Usable For The Creation Of 3D Bone Models Employed To Make Customized Arthroplasty Jigs," was filed Nov. 27, 2007 and is incorporated by reference in its entirety into this Detailed Description.

As can be understood from FIG. 1A, the 2D images are sent to the computer 6 for creating computer generated 3D models. As indicated in FIG. 1B, in one embodiment, point P is identified in the 2D images 16 [block 105]. In one embodiment, as indicated in [block 105] of FIG. 1A, point P may be at the approximate medial-lateral and anterior-posterior center of the patient's joint 14. In other embodiments, point P may be at any other location in the 2D images 16, including anywhere on, near or away from the bones 18, 20 or the joint 14 formed by the bones 18, 20.

As described later in this overview, point P may be used to locate the computer generated 3D models 22, 28, 36 created from the 2D images 16 and to integrate information generated via the 3D models. Depending on the embodiment, point P, which serves as a position and/or orientation reference, may be a single point, two points, three points, a point plus a plane, a vector, etc., so long as the reference P can be used to position and/or orient the 3D models 22, 28, 36 generated via the 2D images 16.

As shown in FIG. 1C, the 2D images 16 are employed to create computer generated 3D bone-only (i.e., "bone models") 22 of the bones 18, 20 forming the patient's joint 14 [block 110]. The bone models 22 are located such that point P is at coordinates ($X_{0-j}$, $Y_{0-j}$, $Z_{0-j}$) relative to an origin ($X_0$, $Y_0$, $Z_0$) of an X-Y-Z axis [block 110]. The bone models 22 depict the bones 18, 20 in the present deteriorated condition with their respective degenerated joint surfaces 24, 26, which may be a result of osteoarthritis, injury, a combination thereof, etc.

Computer programs for creating the 3D computer generated bone models 22 from the 2D images 16 include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org. Further, some embodiments may use customized software such as OMSegmentation, developed by OtisMed, Inc. The OMSegmentation software may extensively uses "ITK" and/or "VTK". Some embodiments may include using a prototype of OMSegmentation, and as such may utilize InsightSNAP software.

As indicated in FIG. 1C, the 3D computer generated bone models 22 are utilized to create 3D computer generated "restored bone models" or "planning bone models" 28 wherein the degenerated surfaces 24, 26 are modified or restored to approximately their respective conditions prior to degeneration [block 115]. Thus, the bones 18, 20 of the restored bone models 28 are reflected in approximately their condition prior to degeneration. The restored bone models 28 are located such that point P is at coordinates ($X_{0-j}$, $Y_{0-j}$, $Z_{0-j}$) relative to the origin ($X_0$, $Y_0$, $Z_0$). Thus, the restored bone models 28 share the same orientation and positioning relative to the origin ($X_0$, $Y_0$, $Z_0$) as the bone models 22.

In one embodiment, the restored bone models 28 are manually created from the bone models 22 by a person sitting in front of a computer 6 and visually observing the bone models 22 and their degenerated surfaces 24, 26 as 3D computer models on a computer screen 9. The person visually observes the degenerated surfaces 24, 26 to determine how and to what extent the degenerated surfaces 24, 26 surfaces on the 3D computer bone models 22 need to be modified to restore them to their pre-degenerated condition. By interacting with the computer controls 11, the person then manually manipulates the 3D degenerated surfaces 24, 26 via the 3D modeling computer program to restore the surfaces 24, 26 to a state the person believes to represent the pre-degenerated condition. The result of this manual restoration process is the computer generated 3D restored bone models 28, wherein the surfaces 24', 26' are indicated in a non-degenerated state.

In one embodiment, the bone restoration process is generally or completely automated. In other words, a computer program may analyze the bone models 22 and their degenerated surfaces 24, 26 to determine how and to what extent the degenerated surfaces 24, 26 surfaces on the 3D computer bone models 22 need to be modified to restore them to their pre-degenerated condition. The computer program then manipulates the 3D degenerated surfaces 24, 26 to restore the surfaces 24, 26 to a state intended to represent the pre-degenerated condition. The result of this automated restoration process is the computer generated 3D restored bone models 28, wherein the surfaces 24', 26' are indicated in a non-degenerated state.

As depicted in FIG. 1C, the restored bone models 28 are employed in a pre-operative planning ("POP") procedure to determine saw cut locations 30 and drill hole locations 32 in the patient's bones that will allow the arthroplasty joint implants to generally restore the patient's joint line to it pre-degenerative alignment [block 120].

In one embodiment, the POP procedure is a manual process, wherein computer generated 3D implant models 34 (e.g., femur and tibia implants in the context of the joint being a knee) and restored bone models 28 are manually manipulated relative to each other by a person sitting in front of a computer 6 and visually observing the implant models 34 and restored bone models 28 on the computer screen 9 and manipulating the models 28, 34 via the computer controls 11. By superimposing the implant models 34 over the restored bone models 28, or vice versa, the joint surfaces of the implant models 34 can be aligned or caused to correspond with the joint surfaces of the restored bone models 28. By causing the joint surfaces of the models 28, 34 to so align, the implant models 34 are positioned relative to the restored bone models 28 such that the saw cut locations 30 and drill hole locations 32 can be determined relative to the restored bone models 28.

In one embodiment, the POP process is generally or completely automated. For example, a computer program may manipulate computer generated 3D implant models 34 (e.g., femur and tibia implants in the context of the joint being a knee) and restored bone models or planning bone models 28 relative to each other to determine the saw cut and drill hole locations 30, 32 relative to the restored bone models 28. The implant models 34 may be superimposed over the restored bone models 28, or vice versa. In one embodiment, the implant models 34 are located at point P' ($X_{0-k}$, $Y_{0-k}$, $Z_{0-k}$) relative to the origin ($X_0$, $Y_0$, $Z_0$), and the restored bone models 28 are located at point P ($X_{0-j}$, $Y_{0-j}$, $Z_{0-j}$). To cause the joint surfaces of the models 28, 34 to correspond, the computer program may move the restored bone models 28 from point P ($X_{0-j}$, $Y_{0-j}$, $Z_{0-j}$) to point P' ($X_{0-k}$, $Y_{0-k}$, $Z_{0-k}$), or vice versa. Once the joint surfaces of the models 28, 34 are in close proximity, the joint surfaces of the implant models 34 may be shape-matched to align or correspond with the joint surfaces of the restored bone models 28. By causing the joint surfaces of the models 28, 34 to so align, the implant models 34 are positioned relative to the restored bone models 28 such that the saw cut locations 30 and drill hole locations 32 can be determined relative to the restored bone models 28.

As indicated in FIG. 1E, in one embodiment, the data 44 regarding the saw cut and drill hole locations 30, 32 relative to point P' ($X_{0-k}$, $Y_{0-k}$, $Z_{0-k}$) is packaged or consolidated as the "saw cut and drill hole data" 44 [block 145]. The "saw cut and drill hole data" 44 is then used as discussed below with respect to [block 150] in FIG. 1E.

As can be understood from FIG. 1D, the 2D images 16 employed to generate the bone models 22 discussed above with respect to [block 110] of FIG. 1C are also used to create computer generated 3D bone and cartilage models (i.e., "arthritic models") 36 of the bones 18, 20 forming the patient's joint 14 [block 130]. Like the above-discussed bone models 22, the arthritic models 36 are located such that point P is at coordinates ($X_{0-j}$, $Y_{0-j}$, $Z_{0-j}$) relative to the origin ($X_0$, $Y_0$, $Z_0$) of the X-Y-Z axis [block 130]. Thus, the bone and arthritic models 22, 36 share the same location and orientation relative to the origin ($X_0$, $Y_0$, $Z_0$). This position/orientation relationship is generally maintained throughout the process discussed with respect to FIGS. 1B-1E. Accordingly, movements relative to the origin ($X_0$, $Y_0$, $Z_0$) of the bone models 22 and the various descendants thereof (i.e., the restored bone models 28, bone cut locations 30 and drill hole locations 32) are also applied to the arthritic models 36 and the various descendants thereof (i.e., the jig models 38). Maintaining the position/orientation relationship between the bone models 22 and arthritic models 36 and their respective descendants allows the "saw cut and drill hole data" 44 to be integrated into the "jig data" 46 to form the "integrated jig data" 48 employed by the CNC machine 10 to manufacture the customized arthroplasty jigs 2.

Computer programs for creating the 3D computer generated arthritic models 36 from the 2D images 16 include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org. Some embodiments may use customized software such as OMSegmentation, developed by OtisMed, Inc. The OMSegmentation software may extensively uses "ITK" and/or "VTK". Also, some embodiments may include using a prototype of OMSegmentation, and as such may utilize InsightSNAP software.

Similar to the bone models 22, the arthritic models 36 depict the bones 18, 20 in the present deteriorated condition with their respective degenerated joint surfaces 24, 26, which may be a result of osteoarthritis, injury, a combination thereof, etc. However, unlike the bone models 22, the arthritic models 36 are not bone-only models, but include cartilage in addition to bone. Accordingly, the arthritic models 36 depict the arthroplasty target areas 42 generally as they will exist when the customized arthroplasty jigs 2 matingly receive the arthroplasty target areas 42 during the arthroplasty surgical procedure.

As indicated in FIG. 1D and already mentioned above, to coordinate the positions/orientations of the bone and arthritic models 36, 36 and their respective descendants, any movement of the restored bone models 28 from point P to point P' is tracked to cause a generally identical displacement for the "arthritic models" 36 [block 135].

As depicted in FIG. 1D, computer generated 3D surface models 40 of the arthroplasty target areas 42 of the arthritic models 36 are imported into computer generated 3D arthroplasty jig models 38 [block 140]. Thus, the jig models 38 are configured or indexed to matingly receive the arthroplasty target areas 42 of the arthritic models 36. Jigs 2 manufactured to match such jig models 38 will then matingly receive the arthroplasty target areas of the actual joint bones during the arthroplasty surgical procedure.

In one embodiment, the procedure for indexing the jig models 38 to the arthroplasty target areas 42 is a manual process. The 3D computer generated models 36, 38 are manually manipulated relative to each other by a person sitting in front of a computer 6 and visually observing the jig models 38 and arthritic models 36 on the computer screen 9 and manipulating the models 36, 38 by interacting with the computer controls 11. In one embodiment, by superimposing the jig models 38 (e.g., femur and tibia arthroplasty jigs in the context of the joint being a knee) over the arthroplasty target areas 42 of the arthritic models 36, or vice versa, the surface models 40 of the arthroplasty target areas 42 can be imported into the jig models 38, resulting in jig models 38 indexed to matingly receive the arthroplasty target areas 42 of the arthritic models 36. Point P' ($X_{0-k}$, $Y_{0-k}$, $Z_{0-k}$) can also be imported into the jig models 38, resulting in jig models 38 positioned and oriented relative to point P' ($X_{0-k}$, $Y_{0-k}$, $Z_{0-k}$) to allow their integration with the bone cut and drill hole data 44 of [block 125].

In one embodiment, the procedure for indexing the jig models 38 to the arthroplasty target areas 42 is generally or completely automated, as disclosed in U.S. patent application Ser. No. 11/959,344 to Park, which is entitled System and Method for Manufacturing Arthroplasty Jigs, was filed Dec. 18, 2007 and is incorporated by reference in its entirety into this Detailed Description. For example, a computer program may create 3D computer generated surface models 40 of the arthroplasty target areas 42 of the arthritic models 36. The computer program may then import the surface models 40 and point P' ($X_{0-k}$, $Y_{0-k}$, $Z_{0-k}$) into the jig models 38, resulting in the jig models 38 being indexed to matingly receive the arthroplasty target areas 42 of the arthritic models 36. The resulting jig models 38 are also positioned and oriented relative to point P' ($X_{0-k}$, $Y_{0-k}$, $Z_{0-k}$) to allow their integration with the bone cut and drill hole data 44 of [block 125].

In one embodiment, the arthritic models 36 may be 3D volumetric models as generated from a closed-loop process. In other embodiments, the arthritic models 36 may be 3D surface models as generated from an open-loop process.

As indicated in FIG. 1E, in one embodiment, the data regarding the jig models 38 and surface models 40 relative to point P' ($X_{0-k}$, $Y_{0-k}$, $Z_{0-k}$) is packaged or consolidated as the "jig data" 46 [block 145]. The "jig data" 46 is then used as discussed below with respect to [block 150] in FIG. 1E.

As can be understood from FIG. 1E, the "saw cut and drill hole data" 44 is integrated with the "jig data" 46 to result in the "integrated jig data" 48 [block 150]. As explained above, since the "saw cut and drill hole data" 44, "jig data" 46 and their various ancestors (e.g., models 22, 28, 36, 38) are matched to each other for position and orientation relative to point P and P', the "saw cut and drill hole data" 44 is properly positioned and oriented relative to the "jig data" 46 for proper integration into the "jig data" 46. The resulting "integrated jig data" 48, when provided to the CNC machine 10, results in jigs 2: (1) configured to matingly receive the arthroplasty target areas of the patient's bones; and (2) having cut slots and drill holes that facilitate preparing the arthroplasty target areas in a manner that allows the arthroplasty joint implants to generally restore the patient's joint line to its pre-degenerated state.

As can be understood from FIGS. 1A and 1E, the "integrated jig data" 44 is transferred from the computer 6 to the CNC machine 10 [block 155]. Jig blanks 50 are provided to the CNC machine 10 [block 160], and the CNC machine 10 employs the "integrated jig data" to machine the arthroplasty jigs 2 from the jig blanks 50.

Figure 1F:
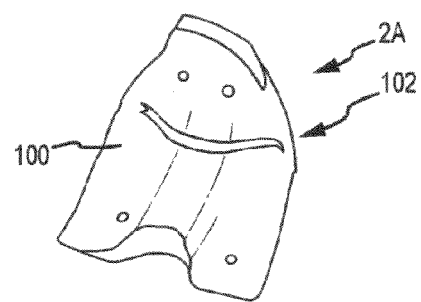
FIGS. 1F and 1G are, respectively, bottom and top perspective views of an example customized arthroplasty femur jig.
Figure 1G:
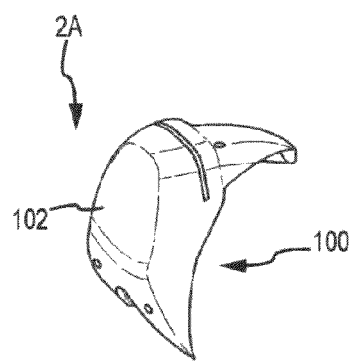
Figure 1H:
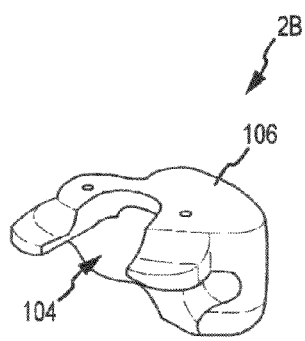
FIGS. 1H and 1I are, respectively, bottom and top perspective views of an example customized arthroplasty tibia jig.
Figure 1I:
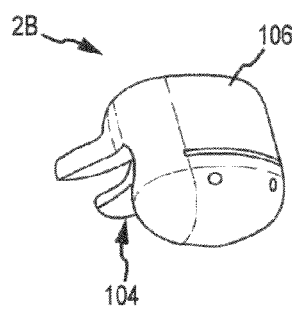

For a discussion of example customized arthroplasty cutting jigs 2 capable of being manufactured via the above-discussed process, reference is made to FIGS. 1F-1I. While, as pointed out above, the above-discussed process may be employed to manufacture jigs 2 configured for arthroplasty procedures involving knees, elbows, ankles, wrists, hips, shoulders, vertebra interfaces, etc., the jig examples depicted in FIGS. 1F-1I are for total knee replacement ("TKR") or partial knee replacement ("PKR") procedures. Thus, FIGS. 1F and 1G are, respectively, bottom and top perspective views of an example customized arthroplasty femur jig 2A, and FIGS. 1H and 1I are, respectively, bottom and top perspective views of an example customized arthroplasty tibia jig 2B.

As indicated in FIGS. 1F and 1G, a femur arthroplasty jig 2A may include an interior side or portion 100 and an exterior side or portion 102. When the femur cutting jig 2A is used in a TKR or PKR procedure, the interior side or portion 100 faces and matingly receives the arthroplasty target area 42 of the femur lower end, and the exterior side or portion 102 is on the opposite side of the femur cutting jig 2A from the interior portion 100.

The interior portion 100 of the femur jig 2A is configured to match the surface features of the damaged lower end (i.e., the arthroplasty target area 42) of the patient's femur 18. Thus, when the target area 42 is received in the interior portion 100 of the femur jig 2A during the TKR or PKR surgery, the surfaces of the target area 42 and the interior portion 100 match.

The surface of the interior portion 100 of the femur cutting jig 2A is machined or otherwise formed into a selected femur jig blank 50A and is based or defined off of a 3D surface model 40 of a target area 42 of the damaged lower end or target area 42 of the patient's femur 18.

As indicated in FIGS. 1H and 1I, a tibia arthroplasty jig 2B may include an interior side or portion 104 and an exterior side or portion 106. When the tibia cutting jig 2B is used in a TKR or PKR procedure, the interior side or portion 104 faces and matingly receives the arthroplasty target area 42 of the tibia upper end, and the exterior side or portion 106 is on the opposite side of the tibia cutting jig 2B from the interior portion 104.

The interior portion 104 of the tibia jig 2B is configured to match the surface features of the damaged upper end (i.e., the arthroplasty target area 42) of the patient's tibia 20. Thus, when the target area 42 is received in the interior portion 104 of the tibia jig 2B during the TKR or PKR surgery, the surfaces of the target area 42 and the interior portion 104 match.

The surface of the interior portion 104 of the tibia cutting jig 2B is machined or otherwise formed into a selected tibia jig blank 50B and is based or defined off of a 3D surface model 40 of a target area 42 of the damaged upper end or target area 42 of the patient's tibia 20.

b. Automatic Segmentation of Scanner Modality Image Data to Generate 3D Surface Model of a Patient's Bone In one embodiment, the 2D images 16 of the patient's joint 14 as generated via the imaging system 8 (see FIG. 1A and [block 100] of FIG. 1B) are analyzed to identify the contour lines of the bones and/or cartilage surfaces that are of significance with respect to generating 3D models 22, 36, as discussed above with respect to [blocks 110 and 130] of FIGS. 1C and 1D. Specifically, a variety of image segmentation processes may occur with respect to the 2D images 16 and the data associated with such 2D images 16 to identify contour lines that are then compiled into 3D bone models, such as bone models 22 and arthritic models 36. A variety of processes and methods for performing image segmentation are disclosed in the remainder of this Detailed Description.

Figure 2A:
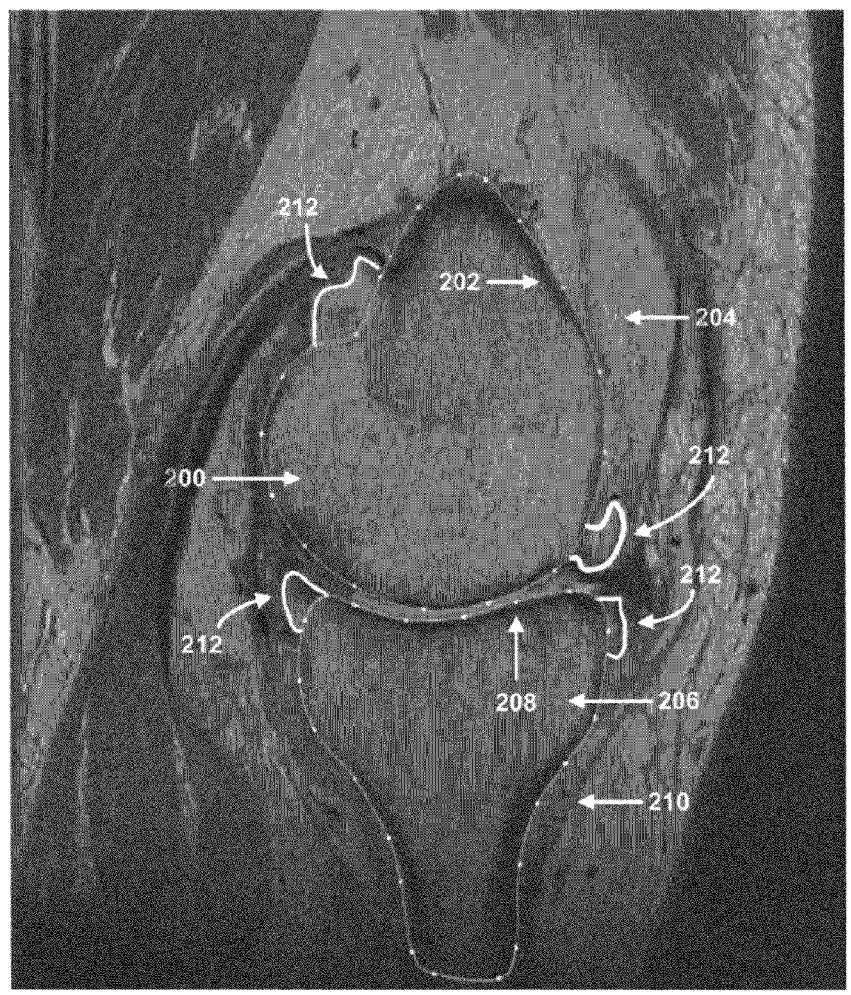
FIG. 2A is a sagittal plane image slice depicting a femur and tibia and neighboring tissue regions with similar image intensity.

The imager 8 typically generates a plurality of image slices 16 via repetitive imaging operations. Depending on whether the imager 8 is a MRI or CT imager, each image slice will be a MRI or CT slice. As shown in FIG. 2A, the image slice may depict the cancellous bone 200, the cortical bone 202 surrounding the cancellous bone, and the articular cartilage lining portions of the cortical bone 202 of an object of interest of a joint, e.g., a femur 204 in a patient's knee joint 14. The image may further depict the cancellous bone 206, the cortical bone 208 of another object of interest in the joint, e.g., a tibia 210 of the knee joint 14. In one embodiment, each image slice 16 may be a two-millimeter 2D image slice.

One embodiment may automatically segment one or more features of interest (e.g., bones) present in MRI or CT scans of a patient joint, e.g., knee, hip, elbow, etc. A typical scan of a knee joint may represent approximately a 100-millimeter by 150-millimeter by 150-millimeter volume of the joint and may include about 40 to 80 slices taken in sagittal planes. A sagittal plane is an imaginary plane that travels from the top to the bottom of the object (e.g., the human body), dividing it into medial and lateral portions. It is to be appreciated that a large inter-slice spacing may result in voxels (volume elements) with aspect ratios of about one to seven between the resolution in the sagittal plane (e.g., the y z plane) and the resolution along the x axis (i.e., each scan slice lies in the yz plane with a fixed value of x). For example, a two-millimeter slice that is 150-millimeters by 150-millimeters may be comprised of voxels that are approximately 0.3-millimeter by 0.3-millimeter by 2-millimeters (for a 512 by 512 image resolution in the sagittal plane).

In one embodiment, each slice may be a gray scale image with a resolution of 512 by 512 voxels where the voxel value represents the brightness (intensity) of the voxel. The intensity may be stored as a 16-bit integer resulting in an intensity range from 0 to 65,535, where 0 may represent black and 65,535 may represent white. The intensity of each voxel typically represents the average intensity of the voxel volume. Other embodiments may employ scans having higher or lower resolutions in the sagittal plane, different inter-slice spacing, or images where the intensity may be represented by a 24 bit vector (e.g., eight bits each for a red component, green component and blue component). Additionally, other embodiments may store intensity values as 32-bit signed integers or floating point values.

Figure 2B:
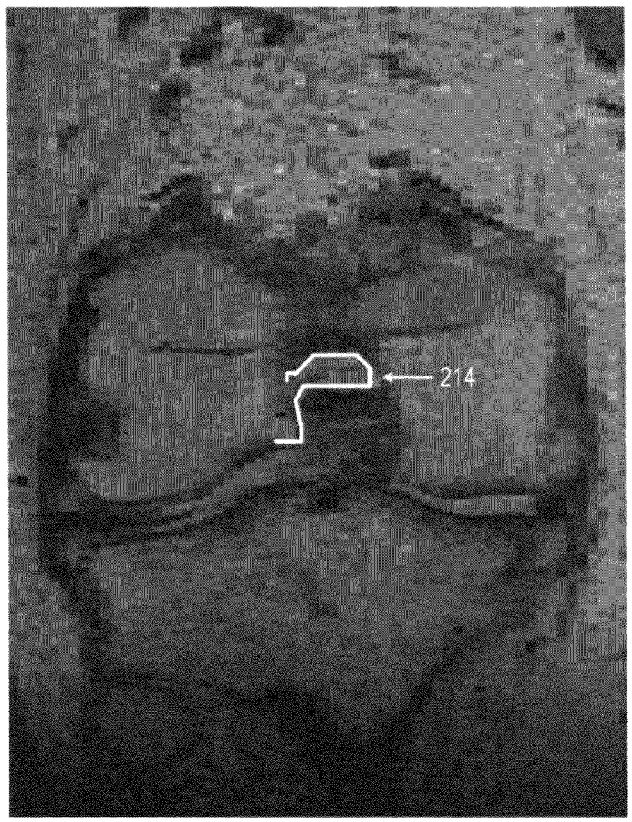
FIG. 2B is a sagittal plane image slice depicting a region extending into the slice from an adjacent image slice.
Figure 2C:
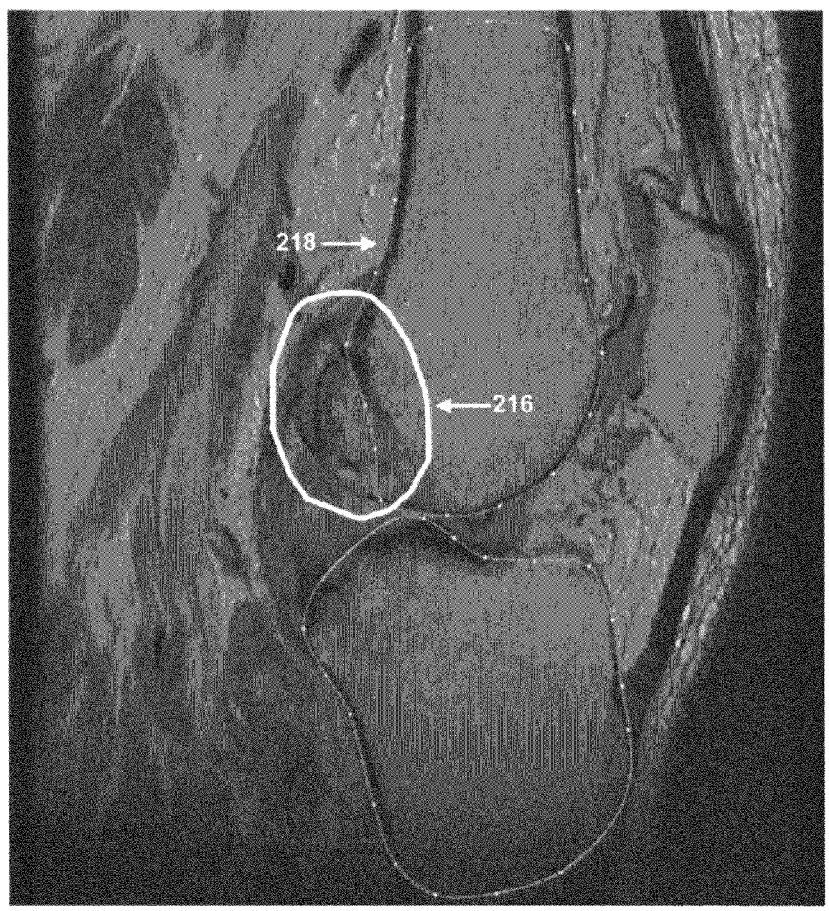
FIG. 2C is a sagittal plane image slice depicting a region of a femur that is approximately tangent to the image slice.

Typical MRI and CT scan data generally provide images where parts of a bone boundary of interest may be well defined while other parts of the bone boundary may be difficult to determine due to voxel volume averaging, the presence of osteophyte growth, the presence of tissue having similar image intensities in neighboring areas to the object to be segmented, amongst other things. Such poor definition of parts of the bone boundary in the images may cause traditional automated segmentation techniques to fail. For example, FIG. 2A depicts regions 212 within a slice where an object boundary may not be visible due to neighboring tissue having about the same intensity as the feature of interest. Depicted in FIG. 2B are regions 214 that may be extended into the slice from adjacent slices due to a high voxel aspect ratio. Depicted in FIG. 2C is a region 216 of the bone boundary 218 that may disappear or lose regularity when the bone boundary 218 is approximately tangent to the slice.

One embodiment may employ image segmentation techniques using a golden template to segment bone boundaries and provide improved segmentation results over traditional automated segmentation techniques. Such techniques may be used to segment an image when similarity between pixels within an object to be identified may not exist. That is, the pixels within a region to be segmented may not be similar with respect to some characteristic or computed property such as a color, intensity or texture that may be employed to associate similar pixels into regions. Instead, a spatial relationship of the object with respect to other objects may be used to identify the object of interest. In one embodiment, a 3D golden template of a feature of interest to be segmented may be used during the segmentation process to locate the target feature in a target scan. For example, when segmenting a scan of a knee joint, a typical 3D image of a known good femur (referred to as a golden femur template) may be used to locate and outline (i.e., segment) a femur in a target scan.

Generally, much of the tissues surrounding the cancellous and cortical matter of the bone to be segmented may vary from one MRI scan to another MRI scan. This may be due to disease and/or patient joint position (e.g., a patient may not be able to straighten the joint of interest because of pain). By using surrounding regions that have a stable connection with the bone (e.g., the grown golden and boundary golden regions of the template as described in more detail below), the registration may be improved. Additionally, use of these regions allow the bone geometry of interest to be captured during the segmentation rather than other features not of interest. Further, the segmentation takes advantage of the higher resolution of features of interest in certain directions of the scan data through the use of a combination of 2D and 3D techniques that selectively increases the precision of the segmentation as described in more detail below with respect to refining the bone registration using an artificially generated image.

Figure 3A:
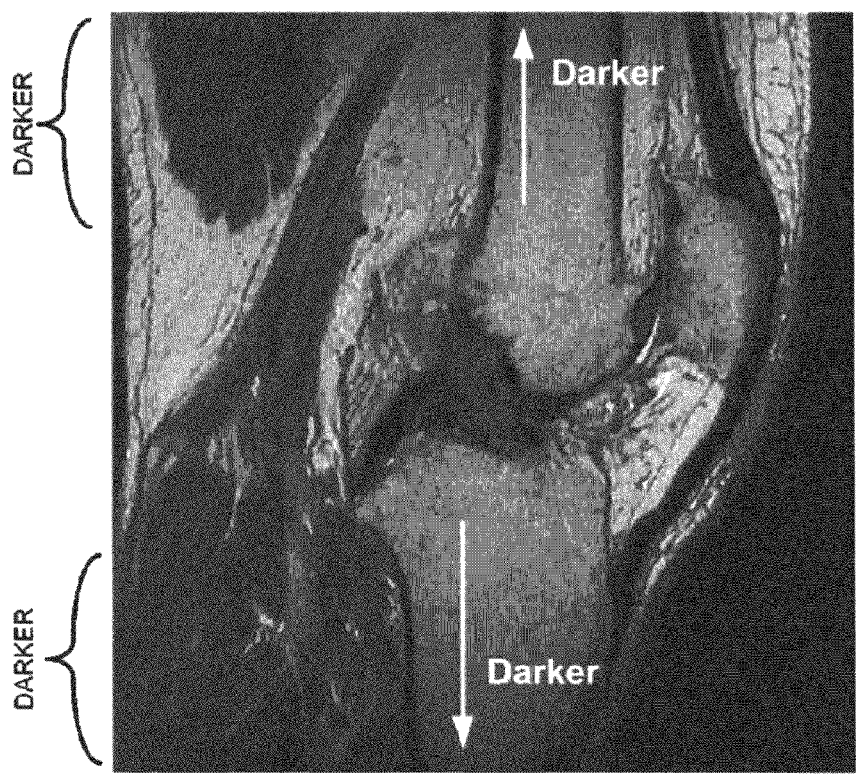
FIG. 3A is a sagittal plane image slice depicting an intensity gradient across the slice.
Figure 3B:
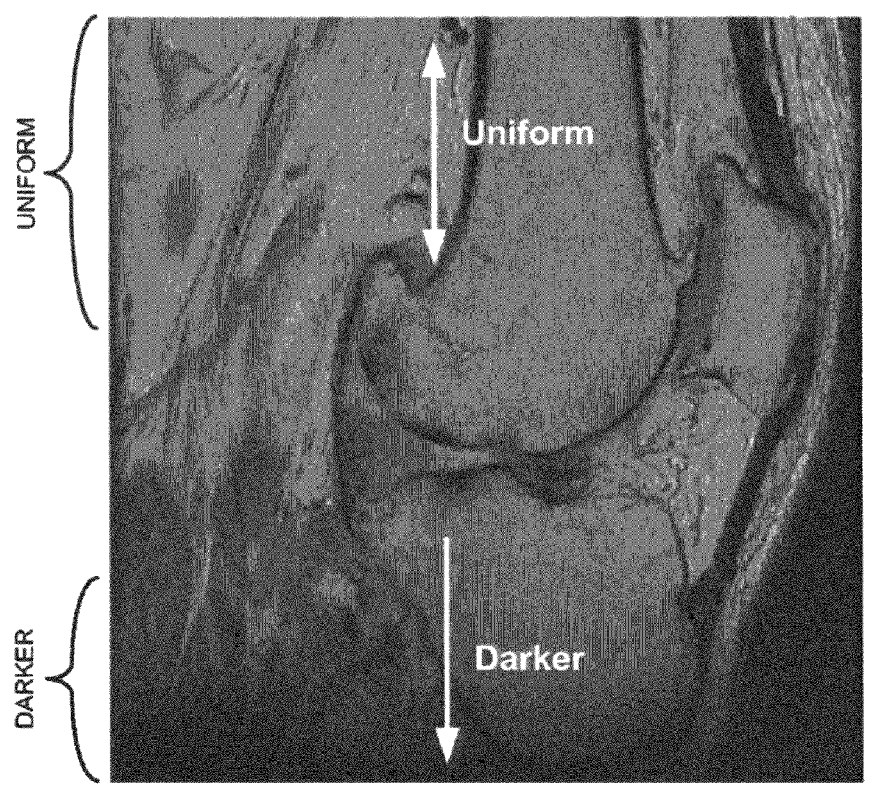
FIG. 3B is a sagittal plane image slice depicting another intensity gradient across the slice.
Figure 3C:
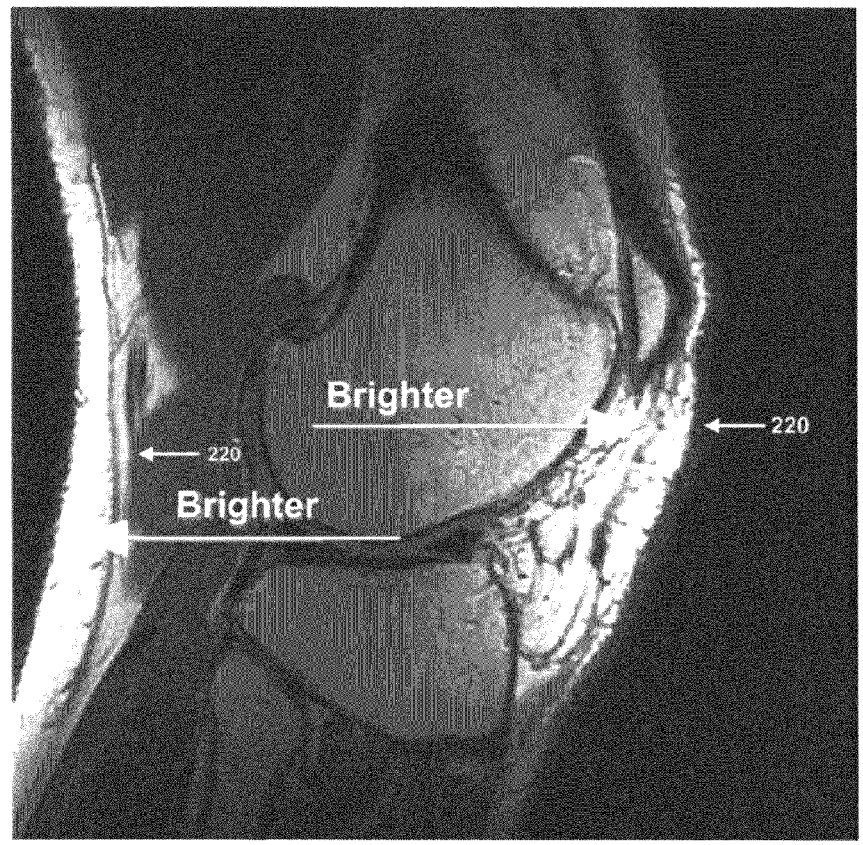
FIG. 3C is a sagittal plane image slice depicting another intensity gradient across the slice.
Figure 4A:
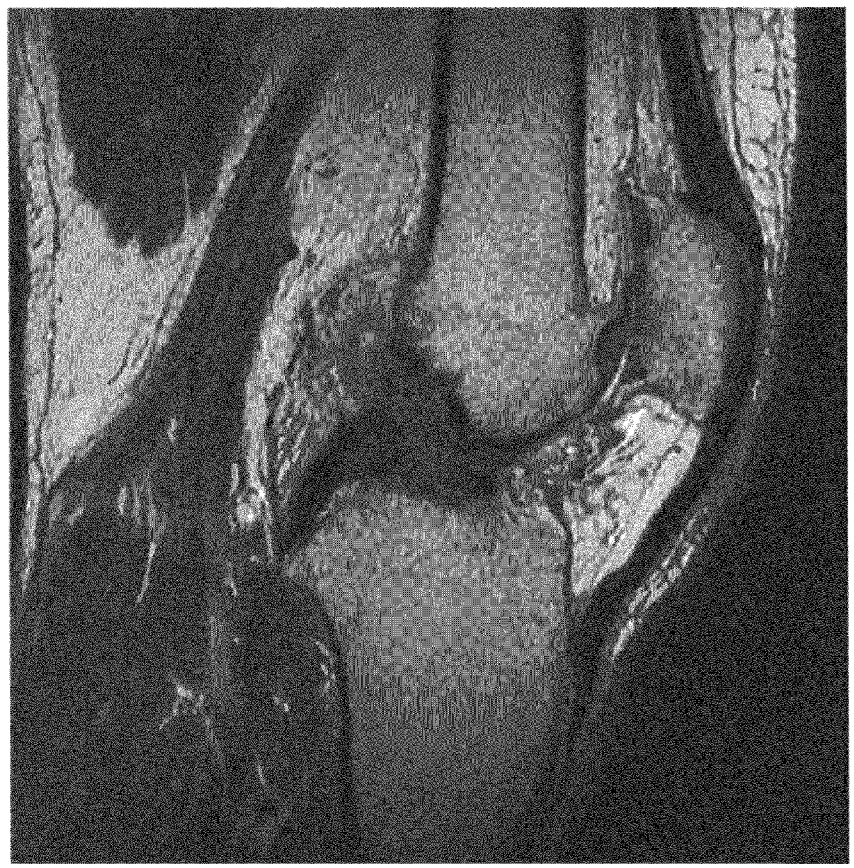
FIG. 4A depicts a sagittal plane image slice with a high noise level.
Figure 4B:
FIG. 4B depicts a sagittal plane image slice with a low noise level.

The segmentation method employed by one embodiment may accommodate a variety of intensity gradients across the scan data. FIGS. 3A-C depict intensity gradients (i.e., the intensity varies non-uniformly across the image) in slices (an intensity gradient that is darker on the top and bottom as depicted in FIG. 3A, an intensity gradient that is darker on the bottom as depicted in FIG. 3B, and an intensity gradient 220 that is brighter on the sides as depicted in FIG. 3C) that may be segmented by one embodiment. Further, the embodiment generally does not require approximately constant noise in the slices to be segmented. The embodiment may accommodate different noise levels, e.g., high noise levels as depicted in FIG. 4A as well as low noise levels as depicted in FIG. 4B. The decreased sensitivity to intensity gradients and noise level typically is due to image registration techniques using a golden template, allowing features of interest to be identified even though the feature may include voxels with differing intensities and noise levels.

Segmentation generally refers to the process of partitioning a digital image into multiple regions (e.g., sets of pixels for a 2D image or sets of voxels in a 3D image). Segmentation may be used to locate features of interest (bones, cartilage, ligaments, etc.) and boundaries (lines, curves, etc. that represent the bone boundary or surface) in an image. In one embodiment, the output of the automatic segmentation of the scan data may be a set of images (scan slices 16) where each image 16 includes a set of extracted closed contours representing bone outlines that identify respective bone location and shape for bones of interest (e.g., the shape and location of the tibia and femur in the scan data of a knee joint). The automatic segmentation of a joint image slices 16 to create 3D models (e.g., bone models 22 and arthritic models 36) of the surface of the bones in the joint may reduce the time required to manufacture customized arthroplasty cutting jigs 2. It is to be appreciated that certain embodiments may generate open contours of the bone shapes of interest to further reduce computation time.

In one embodiment, scan protocols may be chosen to provide good definition in areas where precise geometry reconstruction is required and to provide lower definition in areas that are not as important for geometry reconstruction. The automatic image segmentation of one embodiment employs components whose parameters may be tuned for the characteristics of the image modality used as input to the automatic segmentation and for the features of the anatomical structure to be segmented, as described in more detail below.

In one embodiment, a General Electric 3T MRI scanner may be used to obtain the scan data. The scanner settings may be set as follows: pulse sequence: FRFSE-XL Sagittal PD; 3 Pane Locator—Scout Scan Thickness: 4-millimeters; Imaging Options: TRF, Fast, FR; Gradient Mode: Whole; TE: approximately 31; TR: approximately 2100; Echo Train Length: 8; Bandwidth: 50 Hz; FOV: 16 centimeters, centered at the joint line; Phase FOV: 0.8 or 0.9; Slice Thickness: 2 millimeters; Spacing: Interleave; Matrix: 384×192; NEX: 2; Frequency: SI; and Phase Correct: On. It is to be appreciated that other scanners and settings may be used to generate the scan data.

Typically, the voxel aspect ratio of the scan data is a function of how many scan slices may be obtained while a patient remains immobile. In one embodiment, a two-millimeter inter-slice spacing may be used during a scan of a patient's knee joint. This inter-slice spacing provides sufficient resolution for constructing 3D bone models of the patient's knee joint and may be taken of the joint before the patient moves.

Figure 5:
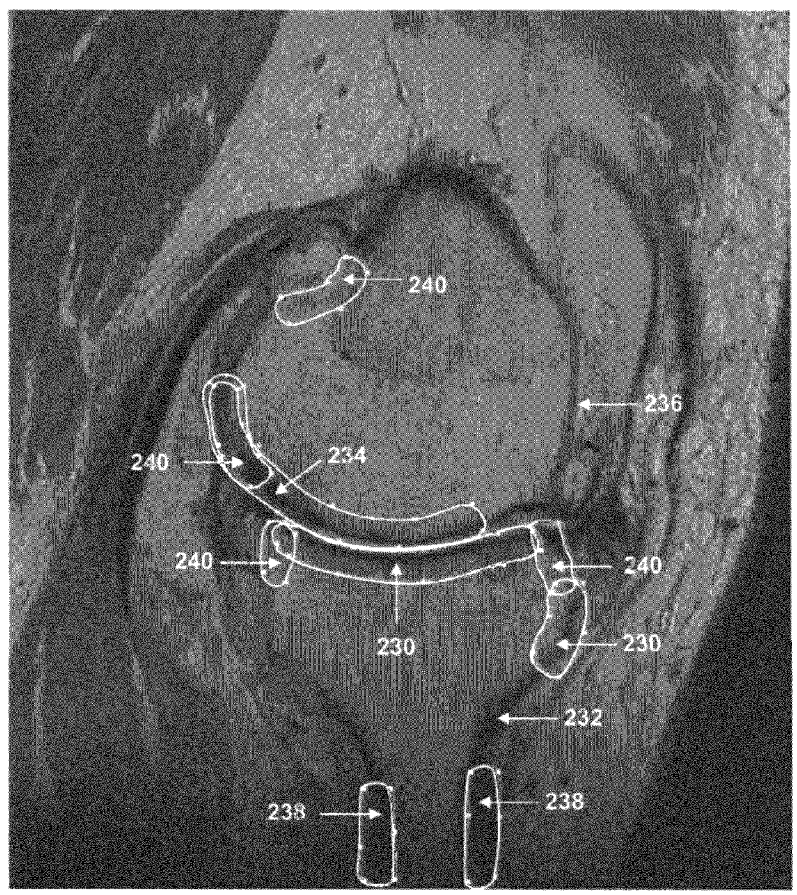
FIG. 5 is a sagittal plane image slice of a femur and tibia depicting regions where good definition may be needed during automatic segmentation of the femur and tibia.

FIG. 5 depicts a MRI scan slice that illustrates image regions where good definition may be needed during automatic segmentation of the image. Typically, this may be areas where the bones come in contact during knee motion, in the anterior shaft area next to the joint and areas located at about a 10- to 30-millimeter distance from the joint. Good definition may be needed in regions 230 of the tibia 232 and regions 234 of the femur 236. Regions 238 depict areas where the tibia is almost tangent to the slice and boundary information may be lost due to voxel volume averaging.

Voxel volume averaging may occur during the data acquisition process when the voxel size is larger than a feature detail to be distinguished. For example, the detail may have a black intensity while the surrounding region may have a white intensity. When the average of the contiguous data enclosed in the voxel is taken, the average voxel intensity value may be gray. Thus, it may not be possible to determine in what part of the voxel the detail belongs.

Regions 240 depict areas where the interface between the cortical bone and cartilage is not clear (because the intensities are similar), or where the bone is damaged and may need to be restored, or regions where the interface between the cancellous bone and surrounding region may be unclear due to the presence of a disease formation (e.g., an osteophyte growth which has an image intensity similar to the adjacent region).

Figure 6:
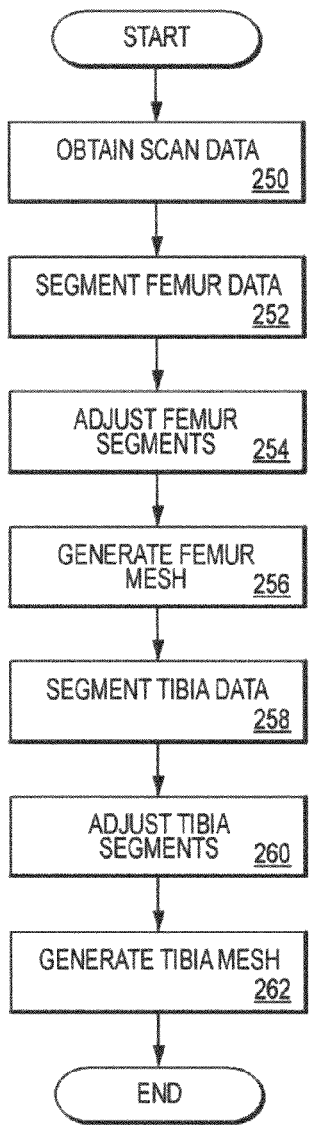
FIG. 6 depicts a flowchart illustrating one method for automatic segmentation of an image modality scan of a patient's knee joint.
Figure 7A:
FIG. 7A is a sagittal plane image slice of a segmented femur.
Figure 7B:
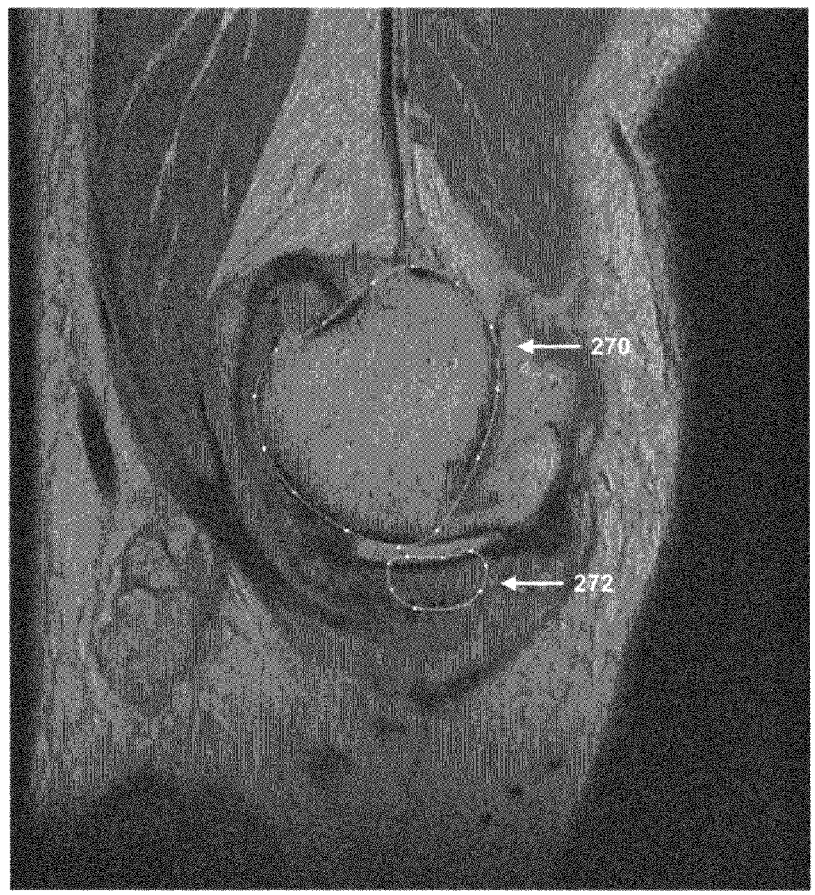
FIG. 7B is a sagittal plane image slice of a segmented femur and tibia.
Figure 7C:
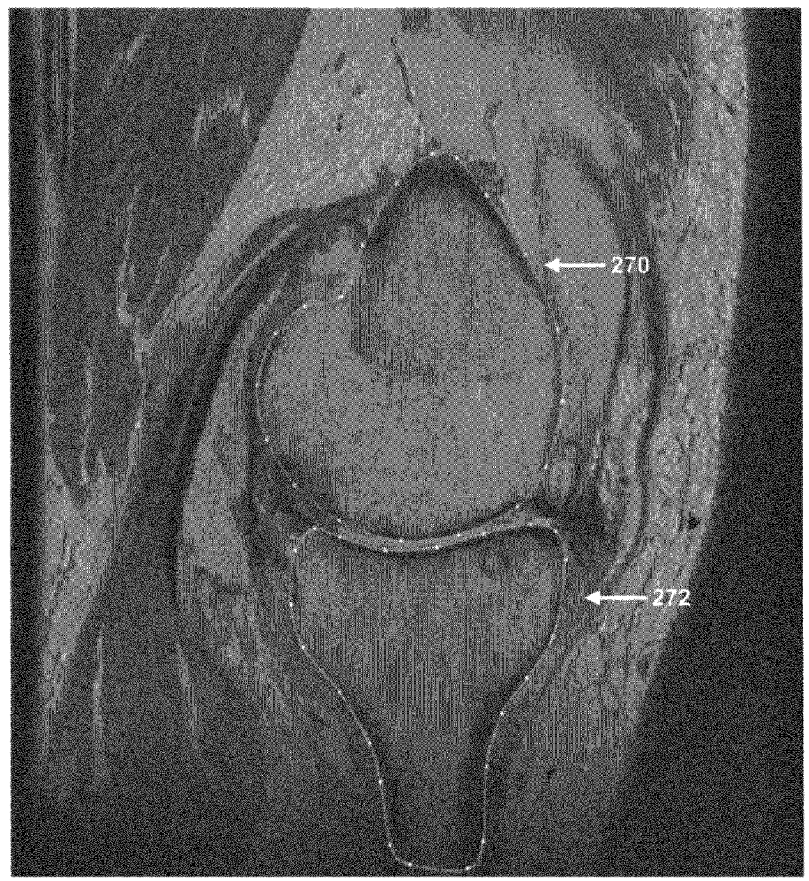
FIG. 7C is another sagittal plane image slice of a segmented femur and tibia.
Figure 7D:
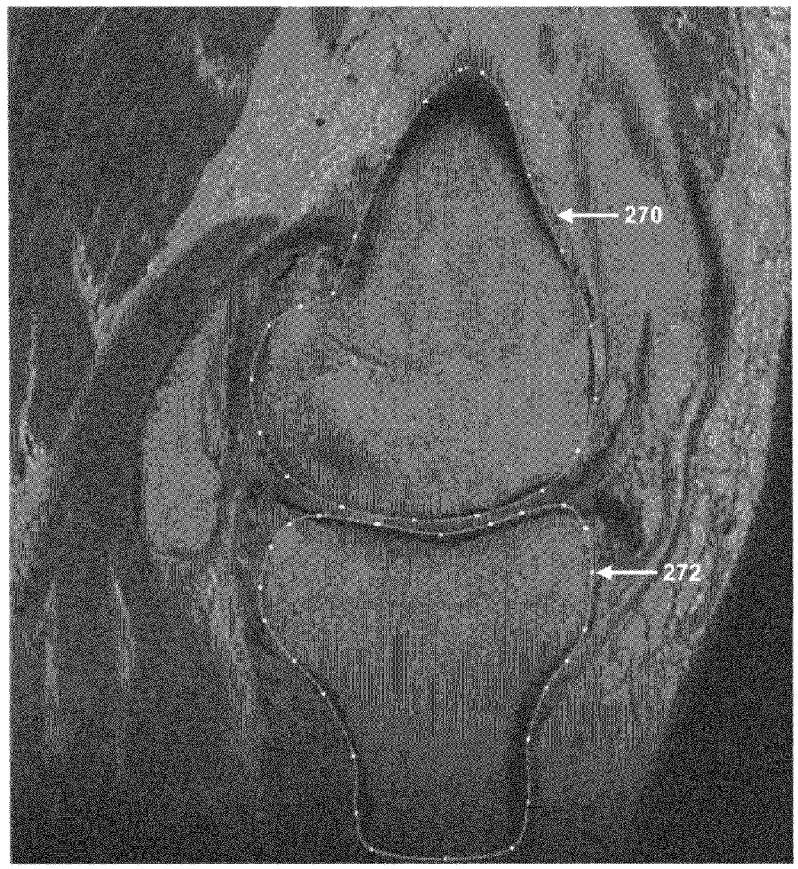
FIG. 7D is another sagittal plane image slice of a segmented femur and tibia.
Figure 7E:
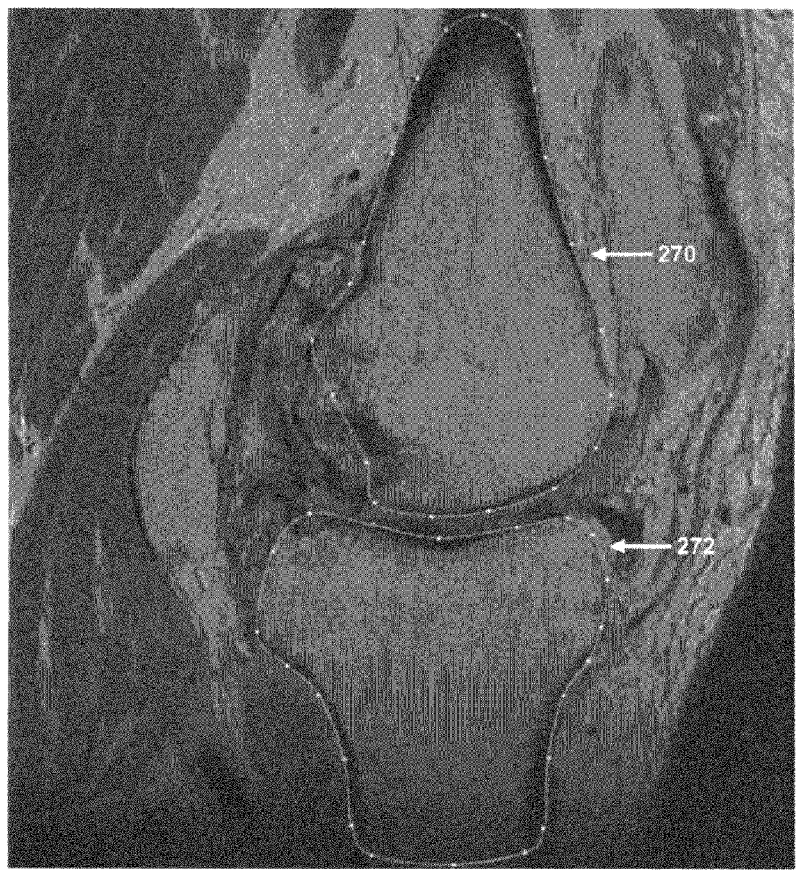
FIG. 7E is another sagittal plane image slice of a segmented femur and tibia.
Figure 7F:
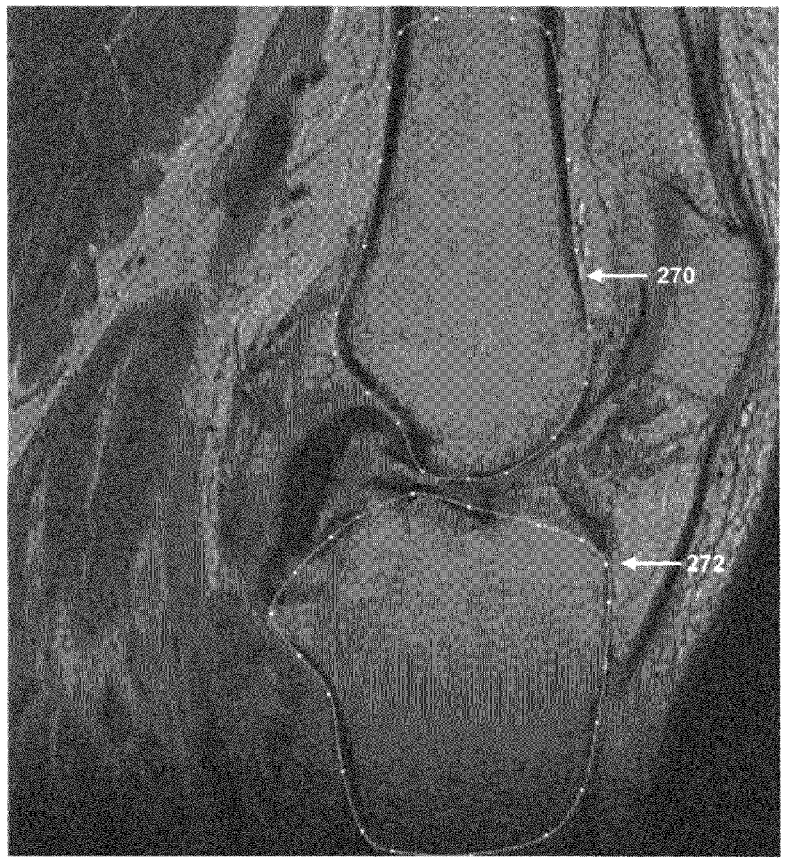
FIG. 7F is another sagittal plane image slice of a segmented femur and tibia.
Figure 7G:
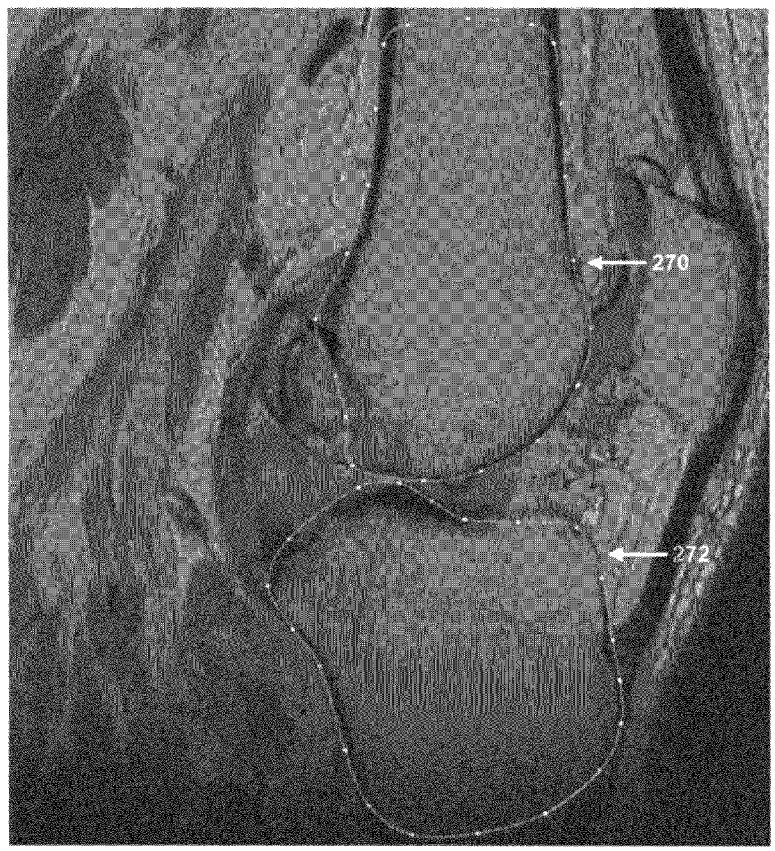
FIG. 7G is another sagittal plane image slice of a segmented femur and tibia.
Figure 7H:
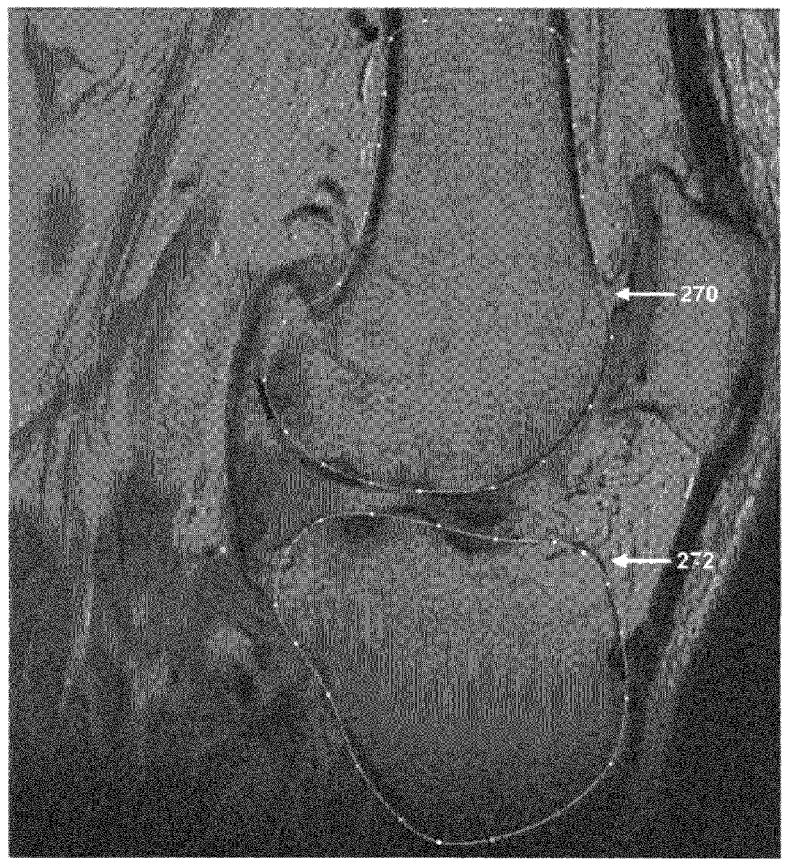
FIG. 7H is another sagittal plane image slice of a segmented femur and tibia.
Figure 7I:
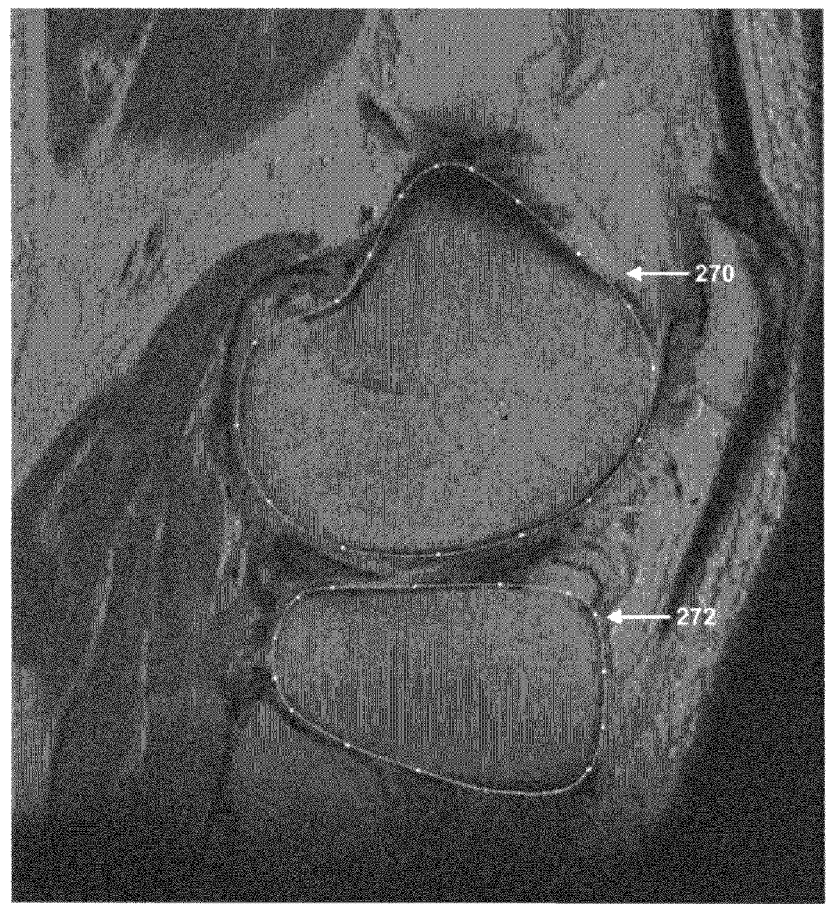
FIG. 7I is another sagittal plane image slice of a segmented femur and tibia.
Figure 7J:
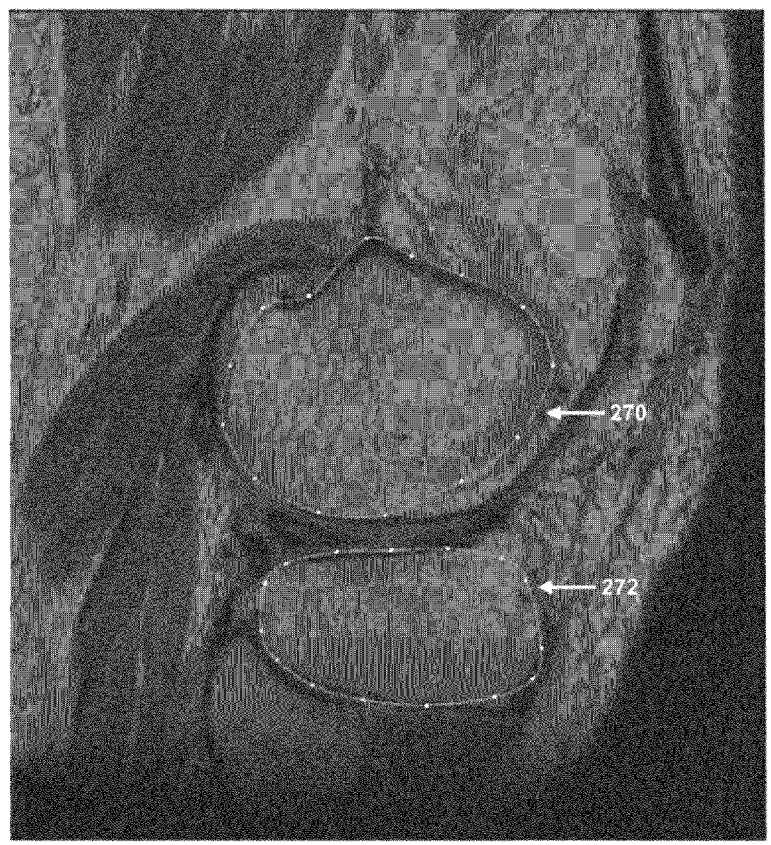
FIG. 7J is another sagittal plane image slice of a segmented femur and tibia.
Figure 7K:
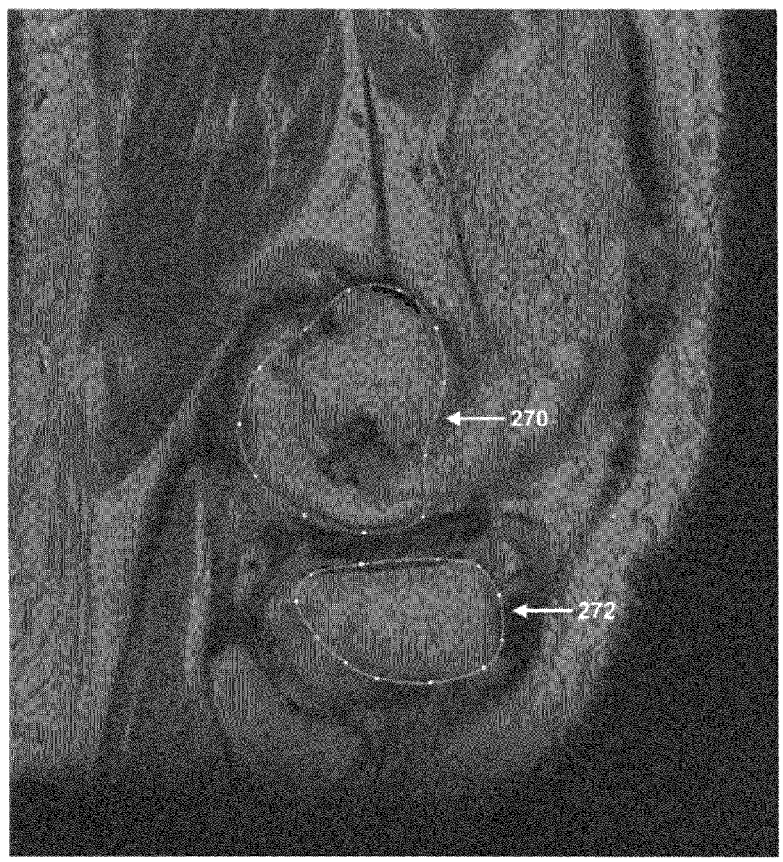
FIG. 7K is another sagittal plane image slice of a segmented femur and tibia.

FIG. 6 depicts a flowchart illustrating one method for automatic segmentation of an image modality scan (e.g., an MRI scan) of a patient's knee joint. Initially, operation 250 obtains a scan of the patient's knee joint. In one embodiment, the scan may include about 50 sagittal slices. Other embodiments may use more or fewer slices. Each slice may be a gray scale image having a resolution of 512 by 512 voxels. The scan may represent approximately a 100-millimeter by 150-millimeter by 150-millimeter volume of the patient's knee. While the invention will be described for an MRI scan of a knee joint, this is by way of illustration and not limitation. The invention may be used to segment other types of image modality scans such as computed tomography (CT) scans, ultrasound scans, positron emission tomography (PET) scans, etc., as well as other joints including, but not limited to, hip joints, elbow joints, etc. Further, the resolution of each slice may be higher or lower and the images may be in color rather than gray scale. It is to be appreciated that transversal or coronal slices may be used in other embodiments.

After operation 250 obtains scan data (e.g., scan images 16) generated by imager 8, operation 252 may be performed to segment the femur data of the scan data. During this operation, the femur may be located and spline curves 270 may be generated to outline the femur shape or contour lines in the scan slices, as depicted in FIGS. 7A-7K. It should be appreciated that one or more spline curves may be generated in each slice to outline the femur contour depending on the shape and curvature of the femur as well as the femur orientation relative to the slice direction.

Figure 8:
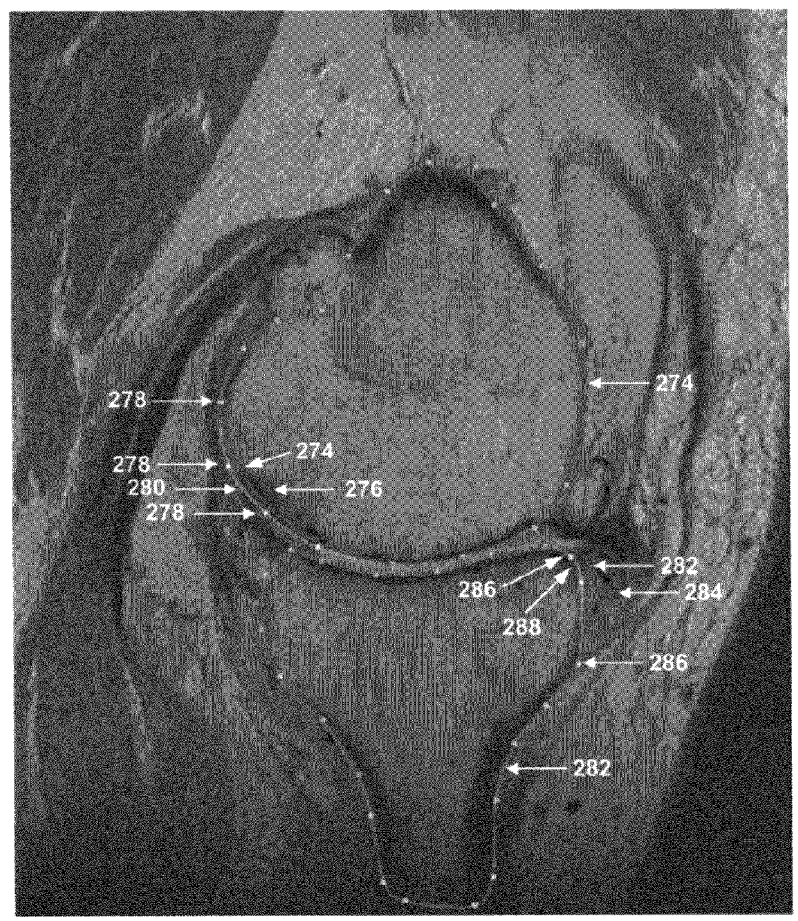
FIG. 8 is a sagittal plane image slice depicting automatically generated slice curves of a femur and a tibia.

Next, in operation 254, a trained technician may verify that the contours of the femur spline curves generated during operation 252 follow the surface of the femur bone. The technician may determine that a spline curve does not follow the bone shape in a particular slice. For example, FIG. 8 depicts an automatically generated femur spline curve 274. The technician may determine that the curve should be enlarged in the lower left part 276 of the femur because it is worn out in this region and may need reconstruction. The technician may determine this by examining the overall 3D shape of the segmented femur and also by comparing lateral and medial parts of the scan data. The segmented region of the slice may be enlarged by dragging one or more control points 278 located on the spline curve 274 to adjust the curve to more closely follow the femur boundary as determined by the technician, as shown by adjusted curve 280. The number of control points on a spline curve may be dependent on the curve length and curvature variations. Typically, 10-25 control points may be associated with a spline curve for spline modification.

Figure 9:
FIG. 9 depicts a 3D mesh geometry of a femur.

Once the technician is satisfied with all of the femur spline curves in the scan slices, operation 256 generates a watertight triangular mesh geometry from the femur segmentation that approximates the 3D surface of the femur. The mesh closely follows the femur spline curves 270 and smoothly interpolates between them to generate a 3D surface model of the femur. FIG. 9 depicts a typical 3D mesh geometry 290 of a target femur generated by one embodiment. Such a 3D model may be a 3D surface model or 3D volume model resulting from open-loop contour lines or closed loop contour lines, respectively. In one embodiment, such a 3D model as depicted in FIG. 9 may be a bone model 22 or an arthritic model 36.

After operation 256, operation 258 may be performed to segment the tibia data in the scan data. During this operation, the tibia is located and spline curves may be generated to locate and outline the shape of the tibia found in the scan slices, as depicted by tibia spline curves 272 in FIGS. 7A-7K. It should be appreciated that one or more spline curves may be generated in each slice to outline the tibia depending on the shape and curvature of the tibia as well as the tibia orientation relative to the slice direction.

Next, in operation 260, the technician may verify the tibia spline curves generated during operation 258. The technician may determine that a spline curve does not follow the tibia in a particular slice. For example, referring back to FIG. 8, an automatically generated tibia spline curve 282 is depicted that may not follow the tibia in the right part of the tibia due to the presence of an osteophyte growth 284. The presence of the osteophyte growth 284 may be determined by examining neighboring slices. In this case, the segmented region may be reduced by dragging one or more control points 286 located on the spline curve to modify the tibia spline curve 282 to obtain the adjusted tibia spline curve 288. As previously discussed, each spline curve may have approximately 10-25 control points depending on the length and curvature variation of the spline curve.

Figure 10:
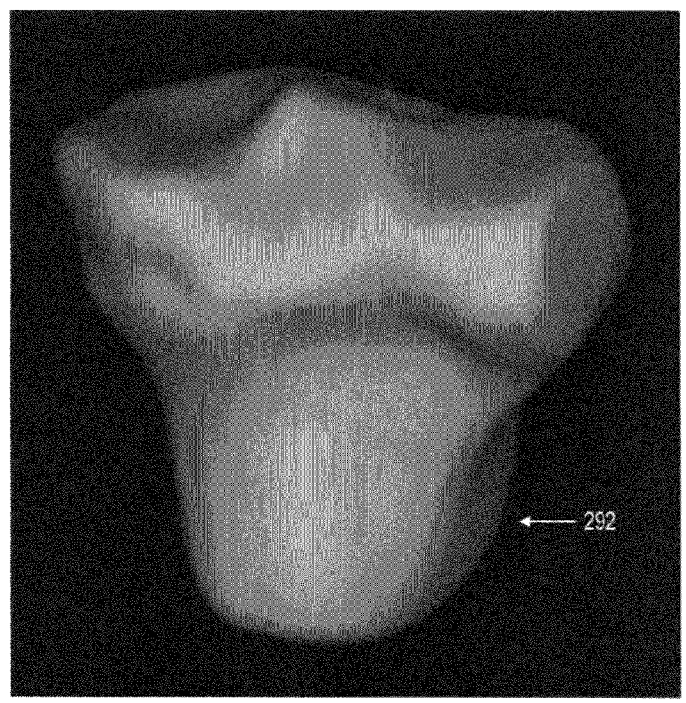
FIG. 10 depicts a 3D mesh geometry of a tibia.

Once the technician is satisfied with all of the tibia spline curves in the scan slices, operation 262 generates a watertight triangular mesh geometry from the tibia segmentation. The mesh closely follows the spline curves and smoothly interpolates between them to generate a 3D surface model of the tibia. FIG. 10 depicts a typical 3D mesh geometry 292 of a target tibia generated by one embodiment. Such a 3D model may be a 3D surface model or 3D volume model resulting from open-loop contour lines or closed loop contour lines, respectively. In one embodiment, such a 3D model as depicted in FIG. 10 may be a bone model 22 or an arthritic model 36.

Because the objects to be located in the scan data typically cannot be segmented by grouping similar voxels into regions, a golden template representative of a typical size and shape of the feature of interest may be employed during the segmentation process to locate the target feature of interest.

Figure 11:
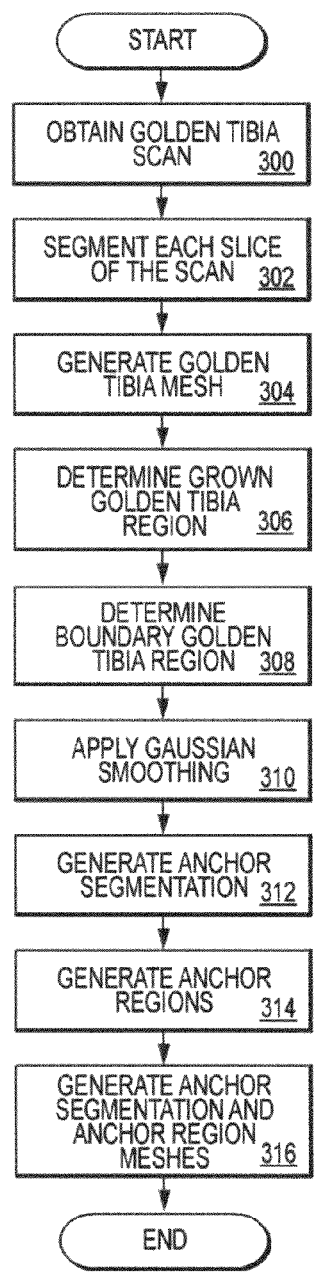
FIG. 11 depicts a flowchart illustrating one method for generating a golden template.

FIG. 11 depicts a flowchart illustrating one method for generating a golden template. The method will be described for generating a golden template of a tibia by way of illustration and not limitation. The method may be used to generate golden templates of other bones including, but not limited to a femur bone, a hip bone, etc.

Initially, operation 300 obtains a scan of a tibia that is not damaged or diseased. The appropriate tibia scan may be chosen by screening multiple MRI tibia scans to locate a MRI tibia scan having a tibia that does not have damaged cancellous and cortical matter (i.e., no damage in tibia regions that will be used as fixed images to locate a corresponding target tibia in a target scan during segmentation), which has good MRI image quality, and which has a relatively average shape, e.g., the shaft width relative to the largest part is not out of proportion (which may be estimated by eye-balling the images). This tibia scan data, referred to herein as a golden tibia scan, may be used to create a golden tibia template. It is to be appreciated that several MRI scans of a tibia (or other bone of interest) may be selected, a template generated for each scan, statistics gathered on the success rate when using each template to segment target MRI scans, and the one with the highest success rate selected as the golden tibia template.

Then, in operation 302 the tibia is segmented in each scan slice. Each segmentation region includes the cancellous matter 322 and cortical matter 324 of the tibia, but excludes any cartilage matter to form a golden tibia region, outlined by a contour curve 320, as depicted in FIG. 12A.

Figure 13A:
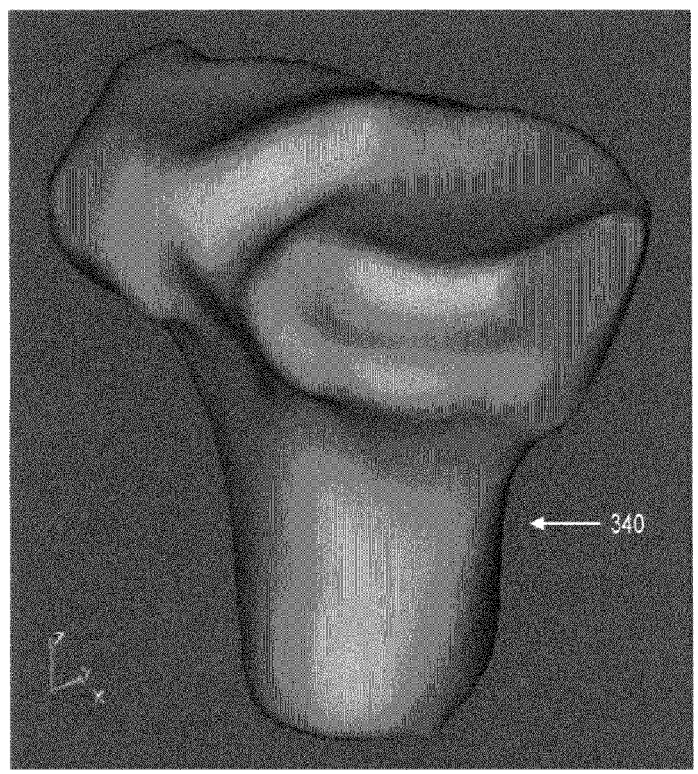
FIG. 13A depicts a golden tibia 3D mesh.

Next, operation 304 generates a golden tibia mesh 340 from the accumulated golden tibia contours of the image slices, as illustrated in FIG. 13A.

Next, operation 306 increases the segmented region in each slice by growing the region to include boundaries between the tibia and adjacent structures where the contact area is generally relatively stable from one MRI scan to another MRI scan.

Figure 12A:
FIG. 12A is a sagittal plane image slice depicting a contour curve outlining a golden tibia region, a contour curve outlining a grown tibia region and a contour curve outlining a boundary golden tibia region.

This grown region may be referred to herein as a grown golden tibia region, outlined by contour curve 328, as depicted in FIG. 12A.

The grown golden region may be used to find the surface that separates the hard bone (cancellous and cortical) from the outside matter (cartilage, tendons, water, etc.). The changes in voxel intensities when going from inside the surface to outside of the surface may be used to define the surface. The grown golden region may allow the registration process to find intensity changes in the target scan that are similar to the golden template intensity changes near the surface. Unfortunately, the golden segmentation region does not have stable intensity changes (e.g., near the articular surface) or may not have much of an intensity change. Thus, the grown region typically does not include such regions because they do not provide additional information and may slow down the registration due to an increased number of points to be registered.

Finally, use of a grown golden region may increase the distance where the metric function detects a feature during the registration process. When local optimization is used, the registration may be moved in a particular direction only when a small movement in that direction improves the metric function. When a golden template feature is farther away from the corresponding target bone feature (e.g., when there is a significant shape difference), the metric typically will not move toward that feature. Use of the larger grown region may allow the metric to detect the feature and move toward it.

Next, operation 308 cuts off most of the inner part of the grown golden tibia region to obtain a boundary golden tibia region 330 depicted in FIG. 12A. The boundary golden tibia region 330 is bounded on the inside by contour curve 332 and the outside by contour curve 328.

The boundary region may be used to obtain a more precise registration of the target bone by using the interface from inside the inside hard bone to the outside hard bone. This may be done so that intensity variations in other areas (e.g., intensity variations deep inside the bone) that may move the registration toward wrong features and decrease the precision of locating the hard bone surface are not used during the registration.

Then, operation 310 applies Gaussian smoothing with a standard deviation of two pixels to every slice of the golden tibia scan. In one embodiment, a vtkimageGaussianSmooth filter (part of Visualization ToolKit, a free open source software package) may be used to perform the Gaussian smoothing by setting the parameter "Standard Deviation" to a value of two.

Then, operation 312 generates an anchor segmentation. The anchor segmentation typically follows the original segmentation where the tibia boundary is well defined in most MRI scans. In areas where the tibia boundary may be poorly defined, but where there is another well defined feature close to the tibia boundary, the anchor segmentation may follow that feature instead. For example, in an area where a healthy bone normally has cartilage, a damaged bone may or may not have cartilage. If cartilage is present in this damaged bone region, the bone boundary separates the dark cortical bone from the gray cartilage matter. If cartilage is not present in this area of the damaged bone, there may be white liquid matter next to the dark cortical bone or there may be another dark cortical bone next to the damaged bone area. Thus, the interface from the cortical bone to the outside matter in this region of the damage bone typically varies from MRI scan to MRI scan. In such areas, the interface between the cortical and the inner cancellous bone may be used. These curves may be smoothly connected together in the remaining tibia areas to obtain the tibia anchor segmentation curve 358, depicted in FIG. 14A.

Figure 14A:
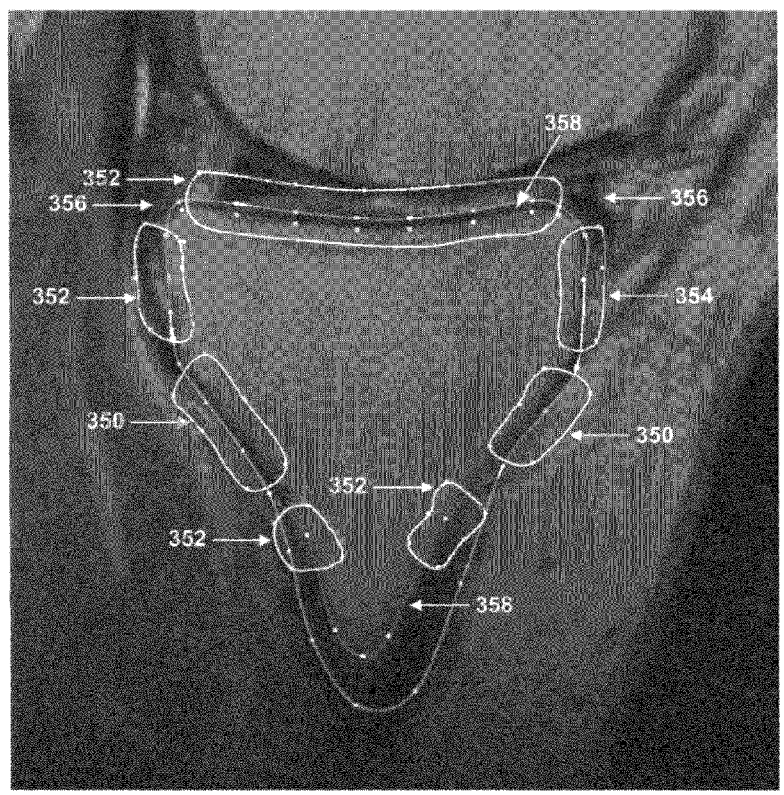
FIG. 14A is a sagittal plane image slice depicting anchor segmentation regions of a tibia.

Then, operation 314 may determine three disjoint regions along the anchor segmentation boundary. Each of these regions is generally well defined in most MRI scans. FIG. 14A depicts these three disjoint regions for a particular image slice. The first region 350, referred to herein as the tibia InDark-OutLight region, depicts a region where the anchor segmentation boundary separates the inside dark intensity cortical matter voxels from the outside light intensity cancellous matter voxels. The second region 352, referred to herein as the tibia InLight-OutDark region, depicts a region where the boundary separates the inside light intensity cancellous matter voxels from the outside dark intensity cortical matter voxels. Finally, region 354, referred to herein as the tibia Dark-in-Light region, depicts a region that has a very thin layer of dark intensity cortical matter voxels along the boundary, but which has light intensity cancellous matter voxels away from the boundary (i.e., on both sides of the boundary). Generally, the other regions along the anchor segmentation boundary vary from scan to scan or may not be clear in most of the scans, as depicted by regions 356. Such regions may be an osteophyte growth with an arbitrary shape but which has about the same intensity as the region next to it. Thus, such regions typically are not used as anchor regions in one embodiment of the invention.

Figure 15A:
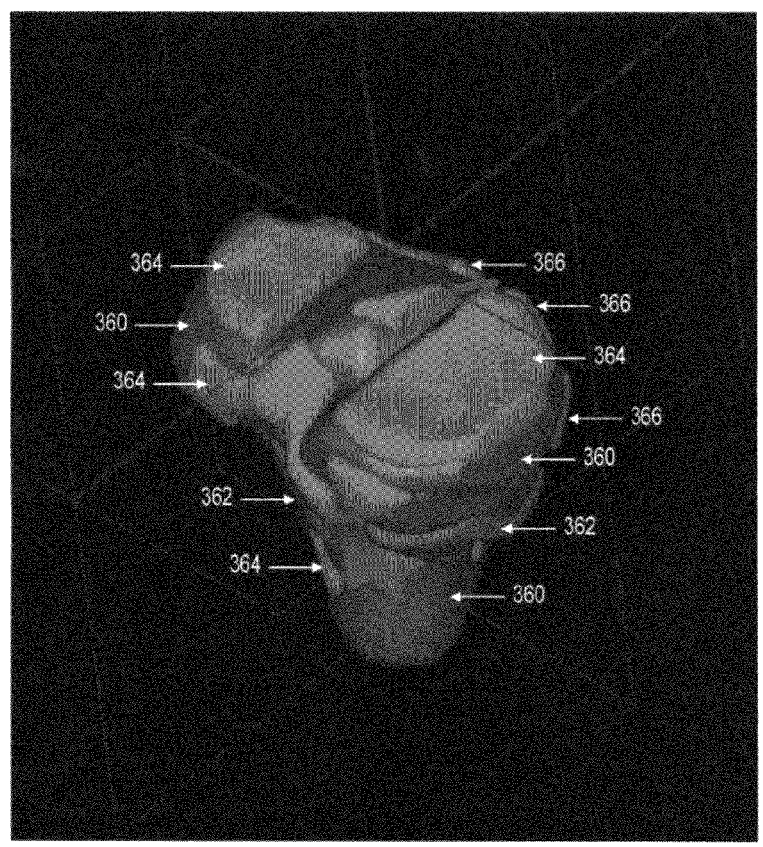
FIG. 15A is a 3D mesh geometry depicting the anchor segmentation mesh, the InDark-OutLight anchor mesh, the InLight-OutDark anchor mesh, and the Dark-In-Light anchor mesh of a tibia.

Finally, operation 316 generates a mesh corresponding to the anchor segmentation and also generates a mesh for each anchor region. FIG. 15A depicts the anchor segmentation mesh 360, the InDark-OutLight anchor region mesh 362, the InLight-OutDark anchor region mesh 364 and the Dark-in-Light anchor region mesh 366 for the tibia. These 3D meshes model the surface of the golden tibia in the specified regions. It is to be appreciated that the 3D meshes are distinct and generally are not combined to create a composite mesh. These meshes may be used to create an artificial fixed image that is used during the registration process as described in more detail below.

Figure 12B:
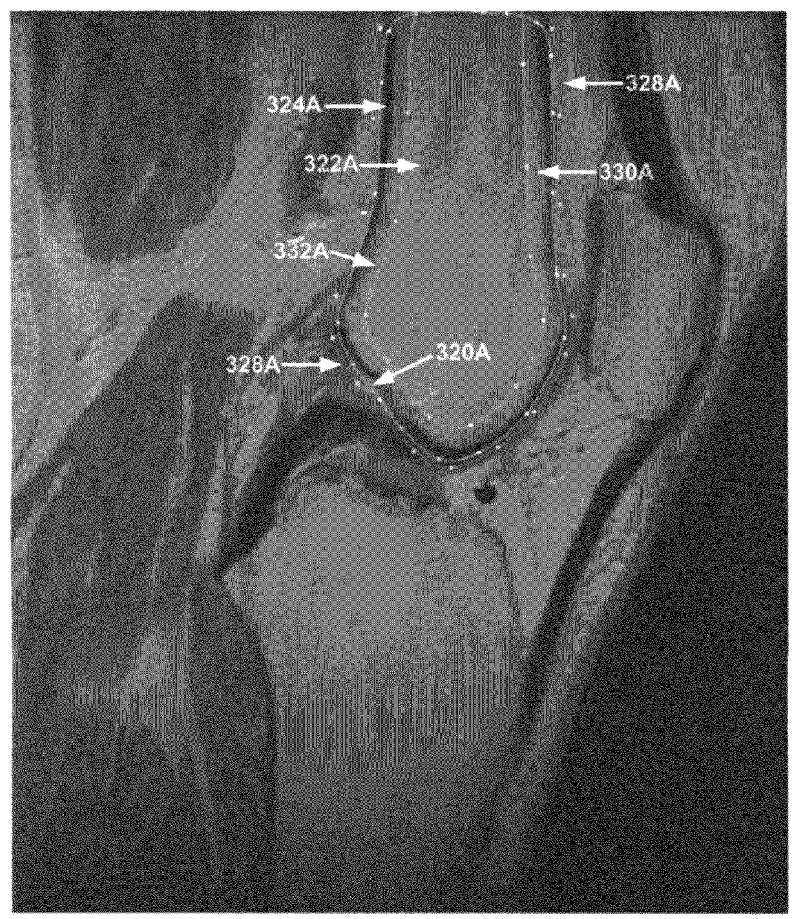
FIG. 12B is a sagittal plane image slice depicting a contour curve outlining a golden femur region, a contour curve outlining a grown femur region and a contour curve outlining a boundary golden femur region.
Figure 13B:
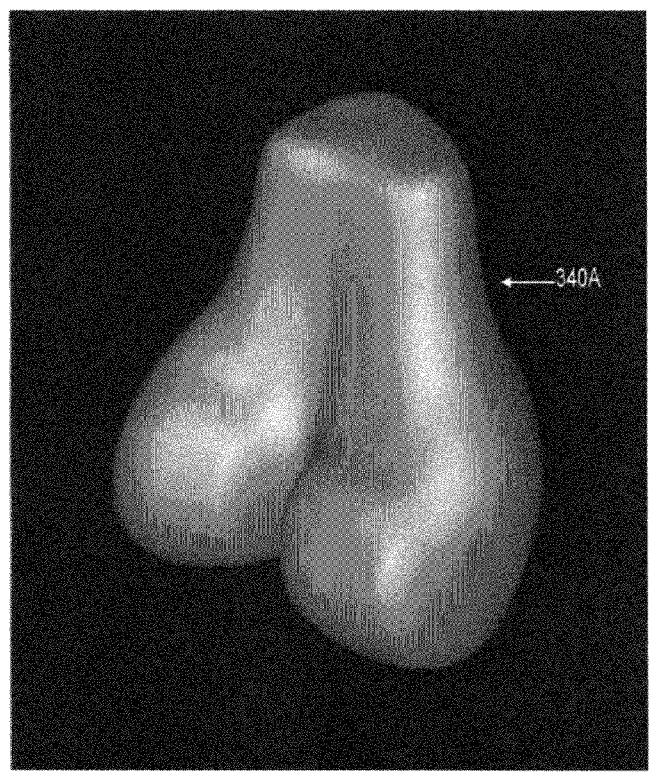
FIG. 13B depicts a golden femur 3D mesh.
Figure 14B:
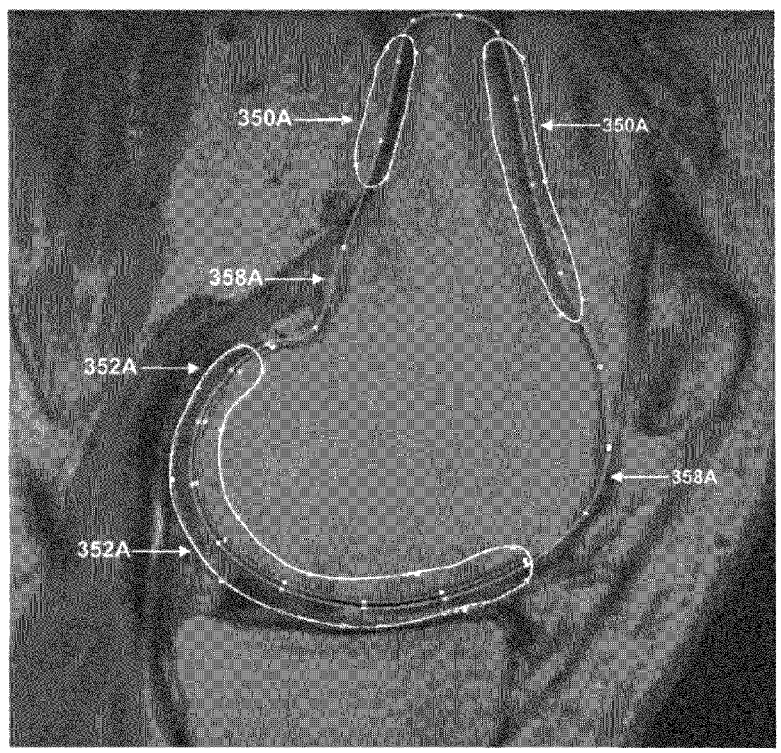
FIG. 14B is a sagittal plane image slice depicting anchor segmentation regions of a femur.
Figure 15B:
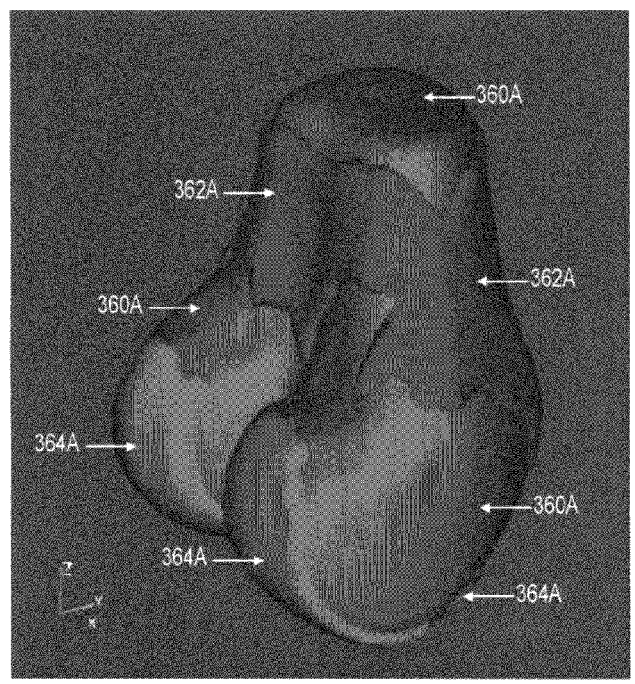
FIG. 15B is a 3D mesh geometry depicting the anchor segmentation mesh, the InDark-OutLight anchor mesh and the InLight-OutDark anchor mesh of a femur.

A golden template of a femur may also be generated in a similar manner using the method depicted by FIG. 11. FIG. 12B depicts the golden femur region, outlined by a contour curve 320A, the grown femur region, outlined by contour curve 328A, and the boundary golden femur region 330A bounded on the inside by contour curve 332A and the outside by contour curve 328A. FIG. 13B depicts the golden femur mesh 340A. FIG. 14B depicts the femur anchor segmentation curve 358A, the femur InDark-OutLight region 350A and the femur InLight-OutDark region 352A. Finally, FIG. 15B depicts the anchor segmentation mesh 360A, the InDark-OutLight anchor region mesh 362A and the InLight-OutDark anchor region mesh 364A for the femur.

Figure 16:
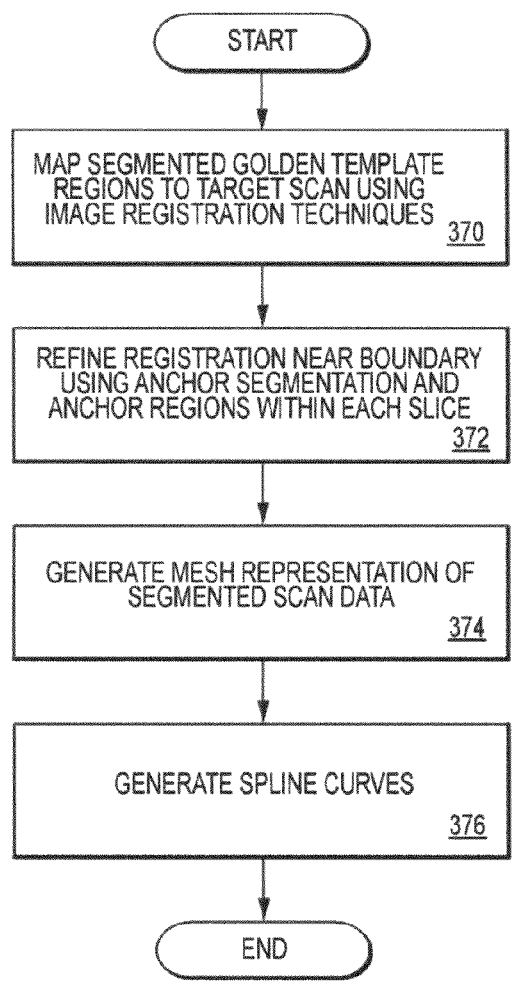
FIG. 16 depicts a flowchart illustrating one method for performing automatic segmentation of scan data using golden template registration.

FIG. 16 depicts a flowchart illustrating one method for performing automatic segmentation (e.g., operation 252 or operation 258 of FIG. 6) of the scan data of a joint (e.g., a MRI scan of a knee joint) using golden template registration. The segmentation method may be used to segment the femur (operation 252 of FIG. 6) and/or the tibia (operation 258 of FIG. 6) in either the left or right knee. Different golden template data may be used to segment the left tibia, right tibia, left femur or right femur. Additionally, other embodiments may segment other joints, including but not limited to, hip joints, elbow joints, by using an appropriate golden template of the feature of interest to be segmented.

Initially, operation 370 maps the segmented golden template and marked regions (e.g., grown and boundary regions) to the target scan data using image registration techniques.

This may be done to locate the corresponding feature of interest in the target scan (e.g., a target femur or tibia). In one embodiment, a 3D golden template may be mapped to the target scan data. Registration transforms the template image coordinate system into the target coordinate system. This allows the template image to be compared and/or integrated with the target image.

Next, operation 372 refines the registration near the feature (e.g., a bone) boundary of interest. Anchor segmentation and anchor regions may be used with a subset of 3D free-form deformations to move points within the plane of the slices (e.g., the yz plane) but not transversal (along the x axis) to the slices. Refinement of the initial registration operation may be necessary to correct errors caused by a high voxel aspect ratio. When a point from a golden template is mapped onto the target scan, it generally maps to a point between adjacent slices of the scan data. For example, if a translation occurs along the x direction, then the point being mapped may only align with a slice when the translation is a multiple of the inter-slice scan distance (e.g., a multiple of two-millimeters for an inter-slice spacing of two-millimeters). Otherwise, the point will be mapped to a point that falls between slices. In such cases, the intensity of the target scan point may be determined by averaging the intensities of corresponding points (voxels) in the two adjacent slices. This may further reduce image resolution. Additionally, refinement of the initial registration operation may correct for errors due to unhealthy areas and/or limited contrast areas. That is, the golden template may be partially pulled away from the actual bone boundary in diseased areas and/or minimal contrast areas (e.g., toward a diseased area having a different contrast) during the initial registration operation.

Next, operation 374 generates a polygon mesh representation of the segmented scan data. A polygon mesh typically is a collection of vertices, edges, and faces that may define the surface of a 3D object. The faces may consist of triangles, quadrilaterals or other simple convex polygons. In one embodiment, a polygon mesh may be generated by applying the registration transform found during operation 372 to all the vertices of a triangle golden template mesh (i.e., the surface of the mesh is composed of triangular faces). It is to be appreciated that the cumulative registration transform typically represents the transform that maps the golden template into the target MRI scan with minimal misalignment error.

Finally, operation 376 generates spline curves that approximate the intersection of the mesh generated by operation 374 with the target MRI slices. Note that these spline curves may be verified by the technician (during operation 254 or operation 260 of FIG. 6).

Figure 17:
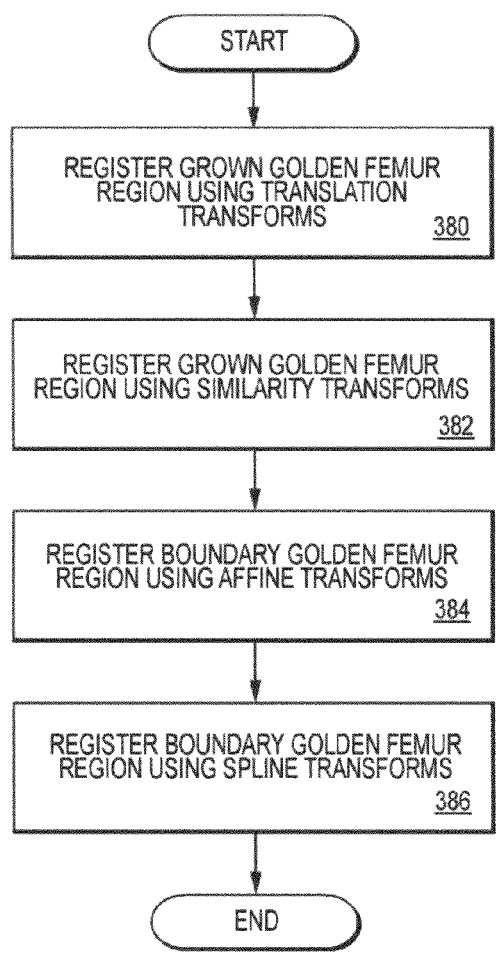
FIG. 17 depicts a flowchart illustrating one method for mapping the segmented golden femur template regions into the target scan data using image registration techniques.

FIG. 17 depicts a flowchart illustrating one method for mapping the segmented golden femur template regions into the target scan using image registration techniques. Registration may be thought of as an optimization problem with a goal of finding a spatial mapping that aligns a fixed image with a target image. Generally several registration operations may be performed, first starting with a coarse image approximation and a low-dimensional transformation group to find a rough approximation of the actual femur location and shape. This may be done to reduce the chance of finding wrong features instead of the femur of interest. For example, if a free-form deformation registration was initially used to register the golden femur template to the target scan data, the template might be registered to the wrong feature, e.g., to a tibia rather than the femur of interest. A coarse registration may also be performed in less time than a fine registration, thereby reducing the overall time required to perform the registration. Once the femur has been approximately located using a coarse registration, finer registration operations may be performed to more accurately determine the femur location and shape. By using the femur approximation determined by the prior registration operation as the initial approximation of the femur in the next registration operation, the next registration operation may find a solution in less time.

Figure 18:
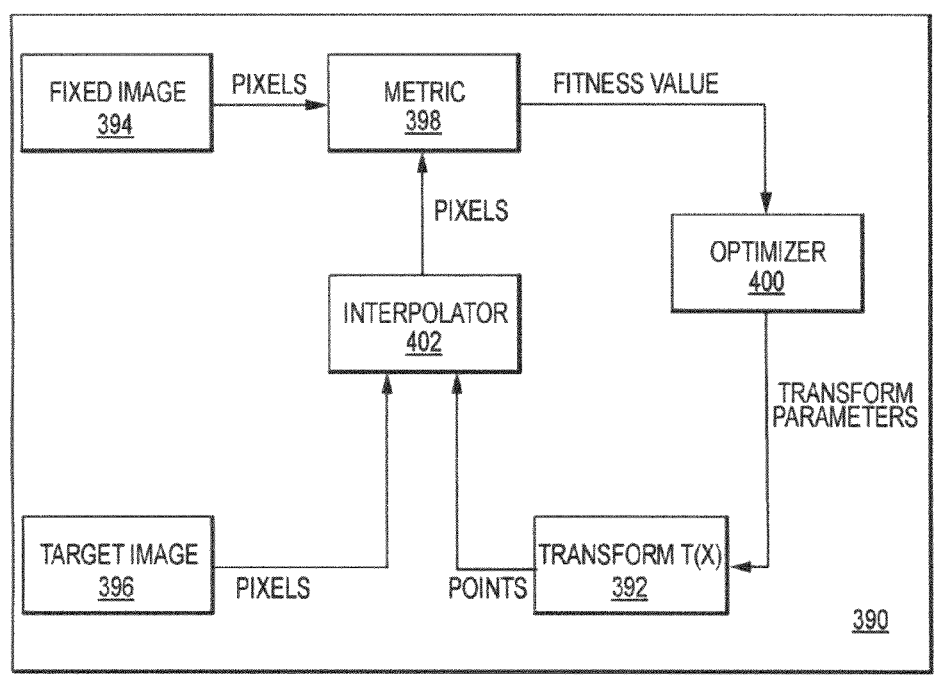
FIG. 18 depicts a registration framework that may be employed by one embodiment.

In one embodiment, each registration operation may employ a registration framework 390 as depicted in FIG. 18. The registration framework 390 may employ an image similarity-based method. Such a method generally includes a transformation model T(X) 392, which may be applied to coordinates of a fixed (or reference) image 394 (e.g., a golden femur template) to locate their corresponding coordinates in a target image 396 space (e.g., a MRI scan), an image similarity metric 398, which quantifies the degree of correspondence between features in both image spaces achieved by a given transformation, and an optimizer 400, which tries to maximize image similarity (or minimize an opposite function) by changing the parameters of the transformation model 392. An interpolator 402 may be used to evaluate target image intensities at non-grid locations (e.g., reference image points that are mapped to target image points that lie between slices). Thus, a registration framework typically includes two input images, a transform, a metric, an interpolator and an optimizer.

Referring again to FIG. 17, operation 380 may approximately register a grown femur region in a MRI scan using a coarse registration transformation. In one embodiment, this may be done by performing an exhaustive translation transform search on the MRI scan data to identify the appropriate translation transform parameters that minimizes translation misalignment of the reference image femur mapped onto the target femur of the target image. This coarse registration operation typically determines an approximate femur position in the MRI scan. During this operation, the femur of the reference image may be overlapped with the target femur of the target image using a translation transformation to minimize translational misalignment of the femurs.

A translational transform, translates (or shifts) an image by the same 3D vector. That is, the reference femur may be mapped into the target image space by shifting the reference femur along one or more axes in the target image space to minimize misalignment. During this operation the reference femur is not rotated, scaled or deformed. In one embodiment, three parameters for the translation transformation may be generated, one parameter for each dimension that specifies the translation for that dimension. The final parameters of the translation transform minimizing the misalignment of the mapped reference femur image coordinates into the target image space may be stored.

Next, operation 382 further refines the image registration determined by operation 380. This may be done by approximately registering the grown femur region of the reference golden template femur into the target MRI scan data using a similarity transformation. In one embodiment, a similarity transformation may be performed in 3D space. The reference golden femur region may be rotated in 3D, translated in 3D and homogeneously scaled to map its coordinates into the target MRI scan data to minimize misalignment between the reference golden femur region and the corresponding region in the target MRI scan. In some embodiments, a center of rotation may be specified so that both the rotation and scaling operations are performed with respect to the specified center of rotation. In one embodiment, a 3D similarity transformation, specified by seven parameters, may be used. One parameter specifies the scaling factor, three parameters specify a versor that represents the 3D rotation and three parameters specify a vector that represents the 3D translation in each dimension. A versor is a unit quanternion that provides a convenient mathematical notation for representing orientations and rotations of objects in three dimensions.

In one embodiment, local minimization techniques may be employed with the similarity transformation to obtain a refined registration of the reference golden femur region onto the target MRI scan that is not far from the registration of the reference golden femur region onto the target MRI scan found in the previous operation 190 and used as the initial starting approximation. Registering the grown golden femur region may increase the distance where the metric function detects a feature during the registration process. When local optimization is used, the registration may be moved in a particular direction only when a small movement in that direction improves the metric function. When a golden femur template feature is farther away from the corresponding target femur feature (e.g., when there is a significant shape difference), the metric typically will not move toward that feature. Use of the larger grown femur region may allow the metric to detect the feature and move toward it.

After operation 382, operation 384 further refines the image registration of the golden femur into the target scan. In one embodiment, an affine transformation may be used to register coordinates of a boundary golden femur region of a golden femur template into the target MRI scan data. In one embodiment, the approximate femur registration found during operation 382 may be used as the initial starting approximation for the affine transformation.

An affine transformation typically is a linear transformation followed by a translation. The affine transformation preserves collinearity between points (i.e., three points which lie on a line continue to be collinear after the transformation) and ratios of distances along a line. In one embodiment, a 3D affine transformation, specified by 12 parameters, may be utilized. Nine parameters of the affine transformation specify the linear transformation (which may be represented by a three by three matrix) and three parameters of the affine transformation specify the 3D translation in each dimension. The parameters of the affine transform that minimizes the misalignment of the boundary golden femur region mapped into the target MRI scan data may be stored.

Finally, operation 386 further refines the image registration of the boundary golden femur region. In one embodiment, a spline transformation may be used to register the coordinates of the boundary golden femur region into the MRI scan data (target image space). In one embodiment, a 3D B-Spline deformable transformation may be employed and the transformation found in operation 384 may be used as the initial transformation values for the 3D B-Spline deformable transformation.

A B-Spline deformable transformation typically is a free form deformation of an object using a deformation field where a deformation vector is assigned to every point in space. For example, a 3D B-spline deformable transform T may specify a 3D vector V(P) for every point P in the original 3D space that is moved by T such that T:P→P+V(P).

In one embodiment, a B-Spline transformation may be specified with M×N parameters, where M is the number of nodes in the B-Spline grid and N is the dimension of the space. In one embodiment, a 3D B-Spline deformable transformation of order three may be used to map every reference image 3D point into the target MRI scan by a different 3D vector. The field of the vectors may be modeled using B-splines. Typically a grid J×K×L of control points may be specified where J, K, and L are parameters of the transformation.

In one embodiment, splines of order three may be used with a grid 9×6×6 of control points. That is, the transformation employs nine control points in the medial/lateral direction (i.e., the x direction), and six control points in the other directions (i.e., y and z directions). Three control points in each dimension (i.e., 3 of 9 in the x direction, 3 of 6 in the y direction and 3 of 6 in the z direction) may be used to specify boundary conditions. As such, the inner spline nodes may form a grid of size 6 by 3 by 3 and the boundary conditions increase the grid to size 9 by 6 by 6. The parametric set for this transformation has a dimension of 3×9×6×6=972 (i.e., each dimension may have a 9×6×6 grid of control points). The final parameters of the spline transformation that minimizes the misalignment between the reference golden femur template and the target MRI scan data may be stored. This may be referred to as the cumulative femur registration transform herein.

Figure 19:
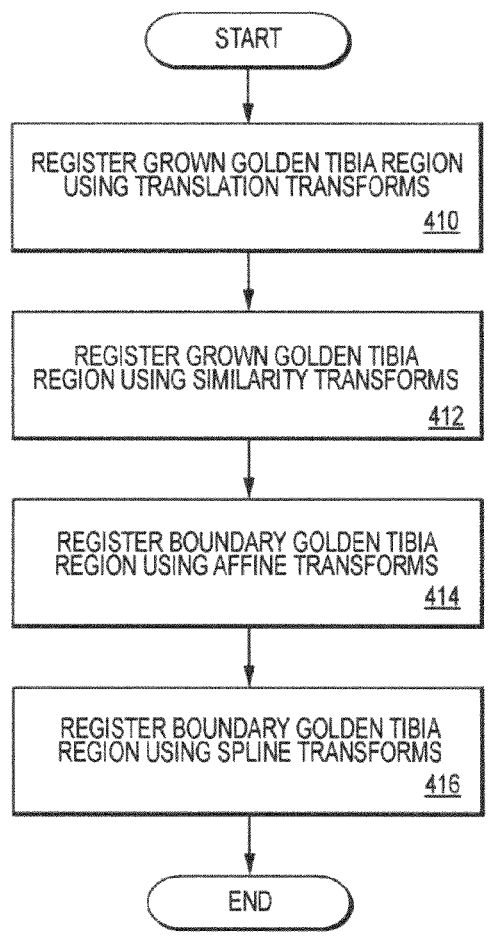
FIG. 19 depicts a flowchart illustrating one method for mapping the segmented golden tibia template regions into the target scan data using image registration techniques.

FIG. 19 depicts a flowchart illustrating one method for mapping the segmented golden tibia template regions into the target scan using image registration techniques. Generally several registration operations may be performed, first starting with a coarse image approximation and a low-dimensional transformation group to find a rough approximation of the actual tibia location and shape. This may be done to reduce the chance of finding wrong features instead of the tibia of interest. For example, if a free-form deformation registration was initially used to register the golden tibia template to the target scan data, the template might be registered to the wrong feature, e.g., to a femur rather than the tibia of interest. A coarse registration may also be performed in less time than a fine registration, thereby reducing the overall time required to perform the registration. Once the tibia has been approximately located using a coarse registration, finer registration operations may be performed to more accurately determine the tibia location and shape. By using the tibia approximation determined by the prior registration operation as the initial approximation of the tibia in the next registration operation, the next registration operation may find a solution in less time.

In one embodiment, each registration operation may employ a registration framework 390 as depicted in FIG. 18. The registration framework 390 may employ an image similarity-based method. Such a method generally includes a transformation model T(X) 392, which may be applied to coordinates of a fixed (or reference) image 394 (e.g., a golden tibia template) to locate their corresponding coordinates in a target image 396 space (e.g., a MRI scan), an image similarity metric 398, which quantifies the degree of correspondence between features in both image spaces achieved by a given transformation, and an optimizer 400, which tries to maximize image similarity by changing the parameters of the transformation model 392. An interpolator 402 may be used to evaluate target image intensities at non-grid locations (i.e., reference image points that are mapped to target image points that lie between slices). Thus, a registration framework typically includes two input images, a transform, a metric, an interpolator and an optimizer.

The automatic segmentation registration process will be described using scan data that includes a right tibia bone. This is by way of illustration and not limitation. Referring again to FIG. 19, operation 410 may approximately register a grown tibia region in a MRI scan using a coarse registration transformation. In one embodiment, this may be done by performing an exhaustive translation transform search on the MRI scan data to identify the appropriate translation transform parameters that minimizes translation misalignment of the reference image tibia mapped onto the target tibia of the target image. This coarse registration operation typically determines an approximate tibia position in the MRI scan. During this operation, the tibia of the reference image may be overlapped with the target tibia of the target image using a translation transformation to minimize translational misalignment of the tibias.

A translational transform, translates (or shifts) an image by the same 3D vector. That is, the reference tibia may be mapped into the target image space by shifting the reference tibia along one or more axes in the target image space to minimize misalignment. During this operation the reference tibia is not rotated, scaled or deformed. In one embodiment, three parameters for the translation transformation may be generated, one parameter for each dimension that specifies the translation for that dimension. The final parameters of the translation transform minimizing the misalignment of the mapped reference tibia image coordinates into the target image space may be stored.

Next, operation 412 further refines the image registration determined by operation 410. This may be done by approximately registering the grown tibia region of the reference golden tibia template into the target MRI scan data using a similarity transformation. In one embodiment, a similarity transformation may be performed in 3D space. The reference golden tibia region may be rotated in 3D, translated in 3D and homogeneously scaled to map its coordinates into the target MRI scan data to minimize misalignment between the reference golden tibia region and the corresponding region in the target MRI scan. In some embodiments, a center of rotation may be specified so that both the rotation and scaling operations are performed with respect to the specified center of rotation. In one embodiment, a 3D similarity transformation, specified by seven parameters, may be used. One parameter specifies the scaling factor, three parameters specify a versor that represents the 3D rotation and three parameters specify a vector that represents the 3D translation in each dimension. A versor is a unit quanternion that provides a convenient mathematical notation for representing orientations and rotations of objects in three dimensions.

In one embodiment, local minimization techniques may be employed with the similarity transformation to obtain a refined registration of the reference golden tibia region onto the target MRI scan that is not far from the registration of the reference golden tibia region onto the target MRI scan found in the previous operation 410 and used as the initial starting approximation. Registering the grown golden tibia region may increase the distance where the metric function detects a feature during the registration process. When local optimization is used, the registration may be moved in a particular direction only when a small movement in that direction improves the metric function. When a golden tibia template feature is farther away from the corresponding target tibia feature (e.g., when there is a significant shape difference), the metric typically will not move toward that feature. Use of the larger grown tibia region may allow the metric to detect the feature and move toward it.

After operation 412, operation 414 further refines the image registration. In one embodiment, an affine transformation may be used to register coordinates of a boundary golden tibia region of a golden tibia template into the target MRI scan data. In one embodiment, the approximate tibia registration found during operation 412 may be used as the initial starting approximation for the affine transformation.

An affine transformation typically is a linear transformation followed by a translation. The affine transformation preserves collinearity between points (i.e., three points which lie on a line continue to be collinear after the transformation) and ratios of distances along a line. In one embodiment, a 3D affine transformation, specified by 12 parameters, may be utilized. Nine parameters of the affine transformation specify the linear transformation (which may be represented by a three by three matrix) and three parameters of the affine transformation specify the 3D translation in each dimension. The parameters of the affine transform that minimizes the misalignment of the boundary golden tibia region mapped into the target MRI scan data may be stored.

Finally, operation 416 further refines the image registration of the boundary golden tibia region. In one embodiment, a spline transformation may be used to register the coordinates of the boundary golden tibia region into the MRI scan data (target image space). In one embodiment, a 3D B-Spline deformable transformation may be employed and the transformation found in operation 414 may be used as the initial transformation values for the 3D B-Spline deformable transformation.

A B-Spline deformable transformation typically is a free form deformation of an object using a deformation field where a deformation vector is assigned to every point in space. In one embodiment, a B-Spline transformation may be specified with M×N parameters, where M is the number of nodes in the B-Spline grid and N is the dimension of the space. In one embodiment, a 3D B-Spline deformable transformation of order three may be used to map every reference image 3D point into the target MRI scan by a different 3D vector. The field of the vectors may be modeled using B-splines. Typically a grid J×K×L of control points may be specified where J, K, and L are parameters of the transformation.

In one embodiment, splines of order three may be used with a grid 9×6×6 of control points. That is, the transformation employs nine control points in the medial/lateral direction (i.e., the x direction, and six control points in the other directions (i.e., the y and z directions). Three control points in each dimension (i.e., 3 of 9 in the x direction, 3 of 6 in the y direction and 3 of 6 in the z direction) may be used to specify boundary conditions. As such, the inner spline nodes may form a grid of size 6 by 3 by 3 and the boundary conditions increase the grid to size 9 by 6 by 6. The parametric set for this transformation has a dimension of 3×9×6×6=972. The final parameters of the spline transformation that minimizes the misalignment between the reference golden tibia template and the target MRI scan data may be stored. This may be referred to as the cumulative tibia registration transform herein.

The shape of the tibia may vary more from patient to patient than does the shape of the femur. As a result, the affine transformation may not provide a close enough registration of the golden tibia template to the target tibia in the target scan. This may cause the Spline transformation to find a local optimum that may be far from the actual tibia in some areas. In one embodiment, an additional registration operation between the affine transform and spline transform operations may be performed to more closely align the golden tibia and the target tibia, allowing the spline transform to converge to the correct local optimum rather than a nearby (but wrong) local optimum.

The class of transforms utilized generally should allow more flexibility (or degrees of freedom) than the Affine transform and less flexibility than the B-spline transforms. The number of degrees of freedom generally is equal to the number of transform parameters. In one embodiment, a class of transforms with more than 12 parameters and less than 3×9×6×6 parameters may be used. For example, a B-spline transform with fewer control points (than used in the subsequent spline transform) may be used for the additional transform operation. Alternatively, the deformations may be modeled using quadric rather than cubic functions.

In another embodiment, several golden tibia templates may be used that represent typical tibia variations, e.g., golden tibia templates for varum, valgum and normal tibia. In one embodiment, each of the golden tibia templates may be used during the translation, similarity and affine transform registration operations to find the template that provides the best match (e.g., best correlation) in the affine transform registration operation. This template may then be used in the remaining registration operations.

Finally, in one embodiment, the tibia registration may be improved by performing the tibia segmentation after the femur segmentation and adding a restriction on the tibia registration transformations such that the tibia may not penetrate the femur. In one embodiment, this may be implemented by introducing a penalty for the penetration. In the target MRI all the voxels that lie inside the femur splines may be marked. The metric functions, described in more detail below, that are used in the registration operations may be modified to include a penalty term. The penalty term may be computed by selecting a set of points on the boundary of the golden template segmentation, applying a transform to the set of points (in a similar way as the transform is applied to the sample points used in the correlation computations), determining if a transformed sample point falls into any of the marked voxels, and adding a large value to the penalty term for each transformed sample point that falls into any of the marked voxels.

In each of the above registration operations, a metric may be used to quantify the degree of correspondence between features in both the reference image and target image achieved by a given transformation. In one embodiment, the metric quantitatively measures how well the transformed golden template image fits the target image (e.g., a target MRI scan) and may compare the gray-scale intensity of the images using a set of sample points in the golden template region to be registered.

Figure 20:
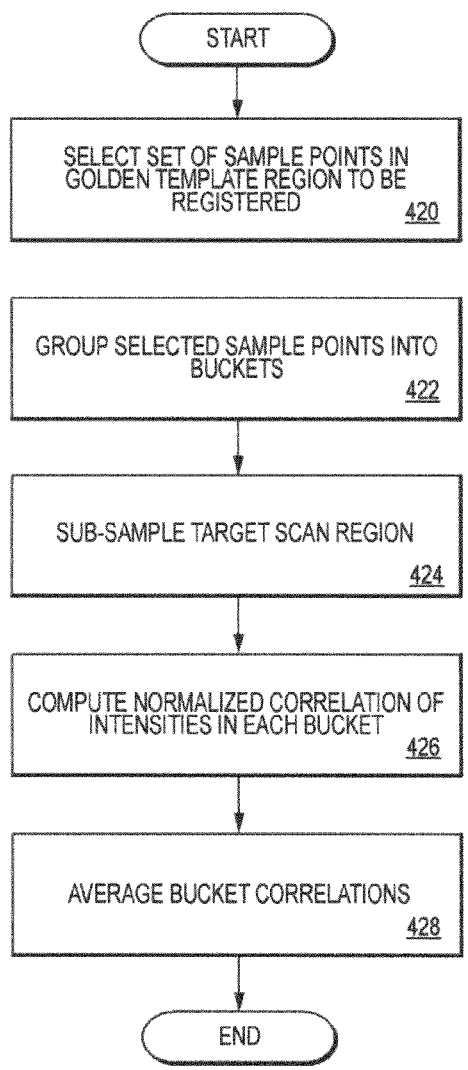
FIG. 20 depicts a flowchart illustrating one method for computing a metric for the registration framework of FIG. 18.

FIG. 20 depicts a flowchart illustrating one method for computing the metric used by the registration operations described above. For a particular registration operation, the metric may be computed in the same way, but the metric may have different parameters specified for the particular registration operation. The metric may be referred to herein as "local correlation in sample points." Initially, operation 420 selects a set of sample points in the golden template region to be registered.

For the translation and similarity transformations, the sample points may be selected as follows. Initially, a rectilinear grid of L×M×N that covers the whole bone in 3D space may be used. L, M, and N may vary from one to 16. In one embodiment, an eight by eight grid in every image slice may be used to select uniform sample points in the grown golden region of the golden template. For each grid cell, the first sample point is selected. If the sample point falls within the grown golden region, it is used. If the sample point falls outside the golden region, it is discarded.

For the affine and spline transformations, the sample points may be determined by randomly selecting one out of every 32 points in the boundary golden region of the MRI slice.

Next, operation 422 groups the selected points into buckets. In one embodiment, buckets may be formed as follows. First, the 3D space may be subdivided into cells using a rectilinear grid. Sample points that belong to the same cell are placed in the same bucket. It should be noted that sample points may be grouped into buckets to compensate for non-uniform intensities in the MRI scan.

For example, MRI scan data may be brighter in the middle of the image and darker towards the edges of the image. This brightness gradient typically is different for different scanners and may also depend on other parameters including elapsed time since the scanner was last calibrated. Additionally, high aspect ratio voxels typically result in voxel volume averaging. That is, cortical bone may appear very dark in areas where its surface is almost perpendicular to the slice and generally will not be averaged with nearby tissues. However, cortical bone may appear as light gray in the areas where its surface is almost tangent to the slice and generally may be averaged with a large amount of nearby tissues.

Next, operation 424 sub-samples the target MRI slice. Sub-sampling the target space generally has the effect of smoothing the metric function. This may remove tiny local minima such that the local minimization algorithm converges to a deeper minimum. In one embodiment, during operations 410 and 412 (of FIG. 19), each slice may be sub-sampled with an eight by eight grid. During operations 414 and 416 (of FIG. 19), each slice may be sub-sampled with a four by four grid. That is, during the sub-sampling, one point from every grid cell may be selected (e.g., the first point) and the remaining points in the grid cells may be discarded.

Next, operation 426 computes a correlation of the intensities of the points in each bucket and their corresponding points in the target MRI scan (after mapping). The correlation (NC) metric may be expressed as:

$$NC(A, B) = \frac{\sum_{i=1}^{N} A_i B_i}{\sqrt{\left(\sum_{i=1}^{N} A_i^2\right)\left(\sum_{i=1}^{N} B_i^2\right)}} \frac{N\sum A_i B_i - \sum A_i \sum B_i}{\sqrt{N\sum A_i^2 - (\sum A_i)^2} \sqrt{N\sum B_i^2 - (\sum B_i)^2}}$$

where $A_i$ is the intensity in the $i^{th}$ voxel of image A, $B_i$ is the intensity in the corresponding $i^{th}$ voxel of image B and N is the number of voxels considered, and the sum is taken from i equals one to N. It should be appreciated that the metric may be optimal when image differences are minimized (or when the correlation of image similarities is maximized). The NC metric generally is insensitive to intensity shifts and to multiplicative factors between the two images and may produce a cost function with sharp peaks and well defined minima.

Finally, operation 428 averages the correlations computed in every bucket with weights proportional to the number of sample points in the bucket.

It is to be appreciated that the above process for computing the metric may compensate for non-uniform intensities, for example, those described above with respect to FIGS. 3A-3C, in the MRI scan data.

During the registration process, an optimizer may be used to maximize image similarity between the reference image and target image by adjusting the parameters of a given transformation model to adjust the location of reference image coordinates in the target image. In one embodiment, the optimizer for a registration operation may use the transformed image (e.g., the transformed golden template) from the previous registration operation as its initial approximation. Then, local optimization techniques may be used to search for a local optimum near the initial starting approximation. This may be done so that any potential matches farther away from the feature of interest (e.g., the femur or tibia in a knee joint) reliably found in an earlier operation may be eliminated.

For the translation transformation, an exhaustive search may be performed using a grid 10×10×10 of size 5-millimeter translation vectors. A translation for every vector in the grid may be performed and the translation providing a maximum local correlation in sample points may be selected as the optimum translation.

For the similarity transformation, a regular step gradient descent optimizer may be used by one embodiment. A regular step gradient descent optimizer typically advances transformation parameters in the direction of the gradient and a bipartition scheme may be used to compute the step size. The gradient of a function typically points in the direction of the greatest rate of change and whose magnitude is equal to the greatest rate of change.

For example, the gradient for a three dimensional space may be given by:

$$\nabla f(x, y, z) = \left(\frac{\partial f}{\partial x}, \frac{\partial f}{\partial y}, \frac{\partial f}{\partial z}\right).$$

That is, the gradient vector may be composed of partial derivatives of the metric function over all the parameters defining the transform. In one embodiment the metric function may be a composition of an outer and N inner functions. The outer function may compute a metric value according to operations 426 and 428 given the vectors $\{A_i\}$ and $\{B_i\}$. The N inner functions may map N sample points from the fixed (reference) image $A_i$ into the target image $B_i$ using the transform and evaluate intensities of the target image $B_i$ in the mapped points. Each of the inner functions generally depends on the transform parameters as well as on the point in the "from" space to which the transform is applied. When computing the partial derivatives, the chain rule for computing a derivative of the function composition may be used.

To find a local minimum, parameter steps may be taken in the direction of the negative of the metric gradient (or the approximate gradient) over the transform parameter space at the current point. This generally optimizes the metric which typically has a local minimum when features of the reference image mapped into corresponding features of the target image have minimal misalignment).

The initial center of rotation for the similarity transformation (e.g., operation 382 of FIG. 17) may be specified as the center of a bounding box (or minimum sized cuboid with sides parallel to the coordinate planes) that encloses the feature (e.g., a bone) registered in the translation registration (e.g., operation 380 of FIG. 17). Scaling coefficients of approximately 40-millimeters may be used for the scaling parameters when bringing them together with translation parameters. It is to be appreciated that the gradient computation generally assumes that there is some metric function. With a similarity transformation, the transform parameters do not have the same dimensionality. The translation parameters have a dimension of millimeters, while the parameters for rotational angles and scaling do not have a dimension of millimeters. In one embodiment, a metric M may be defined as $$M = \text{SQRT}(X^2 + Y^2 + Z^2 + (40\text{-millimeter}*A1)^2 + \ldots)$$

where X is the translation along the x axis, Y is the translation along the y axis, Z is the translation along the z axis, A1 is the first rotation angle, etc. A scaling coefficient of approximately 40-millimeters may be used because it is approximately half the size of the bone (in the anterior/posterior and medial/lateral directions) of interest and results in a point being moved approximately 40-millimeters when performing a rotation of one radian angle.

In one embodiment, a maximum move of 1.5-millimeters may be specified for every point, a relaxation factor may be set to 0.98 and a maximum of 300 iterations may be performed to determine the parameters of the similarity transformation that results in minimal misalignment between the reference image and target MRI scan.

For the affine transformation, a regular step gradient optimizer may be used by one embodiment. Scaling coefficients of approximately 40-millimeters may be used for the matrix coefficients variations when bringing them together with translation parameters. A maximum 1.0-millimeter move for every point may be set for each iteration, the relaxation factor may be set to 0.98 and a maximum of 300 iterations may be performed to determine the parameters of the affine transformation that results in minimal misalignment.

For the B-spline transformation, a modified regular step gradient descent optimizer may be used by one embodiment when searching for the best B-spline deformable transformation. An MRI image gradient may often follow the bone surface in diseased areas (e.g., where the bone contact surface is severely damaged and/or where osteophytes have grown). Such a gradient may cause deformations of the golden template that would introduce large distortions in the segmented bone shape.

In one embodiment, the MRI image gradient may be corrected for such deformations by computing a normal to golden boundary vector field where every vector points towards the closest point in the golden template shape found during the affine transformation (e.g., operation 384 of FIG. 17). This may be done using a distance map (also referred to as a distance transform). A distance map supplies each voxel of the image with the distance to the nearest obstacle voxel (e.g., a boundary voxel in a binary image). In one embodiment, the gradient of the signed distance map of the golden tibia region may be mapped using the affine transformation found in operation 384 of FIG. 17. In one embodiment, a signed Danielsson distance map image filter algorithm may be used. Then, the MRI image gradient may be projected onto the vector field to obtain the corrected gradient field. This corrected gradient field is parallel to the normal to golden boundary field and typically defines a very thin subset of the set of B-spline transformations that may be traveled during the optimization.

Additionally, rather than computing one gradient vector for the transform space and taking a step along it, a separate gradient may be computed for every spline node. In one embodiment, order three B-splines (with J×K×L control nodes) may be used and J×K×L gradients may be computed, one for each control point. At every iteration, each of the spline nodes may be moved along its respective gradient. This may allow the spline curve to be moved in low contrast areas at the same time it is moved in high contrast areas. A relaxation factor of 0.95 may be used for each spline node. A maximum move of one-millimeter may be set for every point during an iteration and a maximum of 20 iterations may be performed to find the parameters of the B-spline transformation that provides minimal misalignment of the golden tibia region mapped into the target MRI scan.

Figure 21:
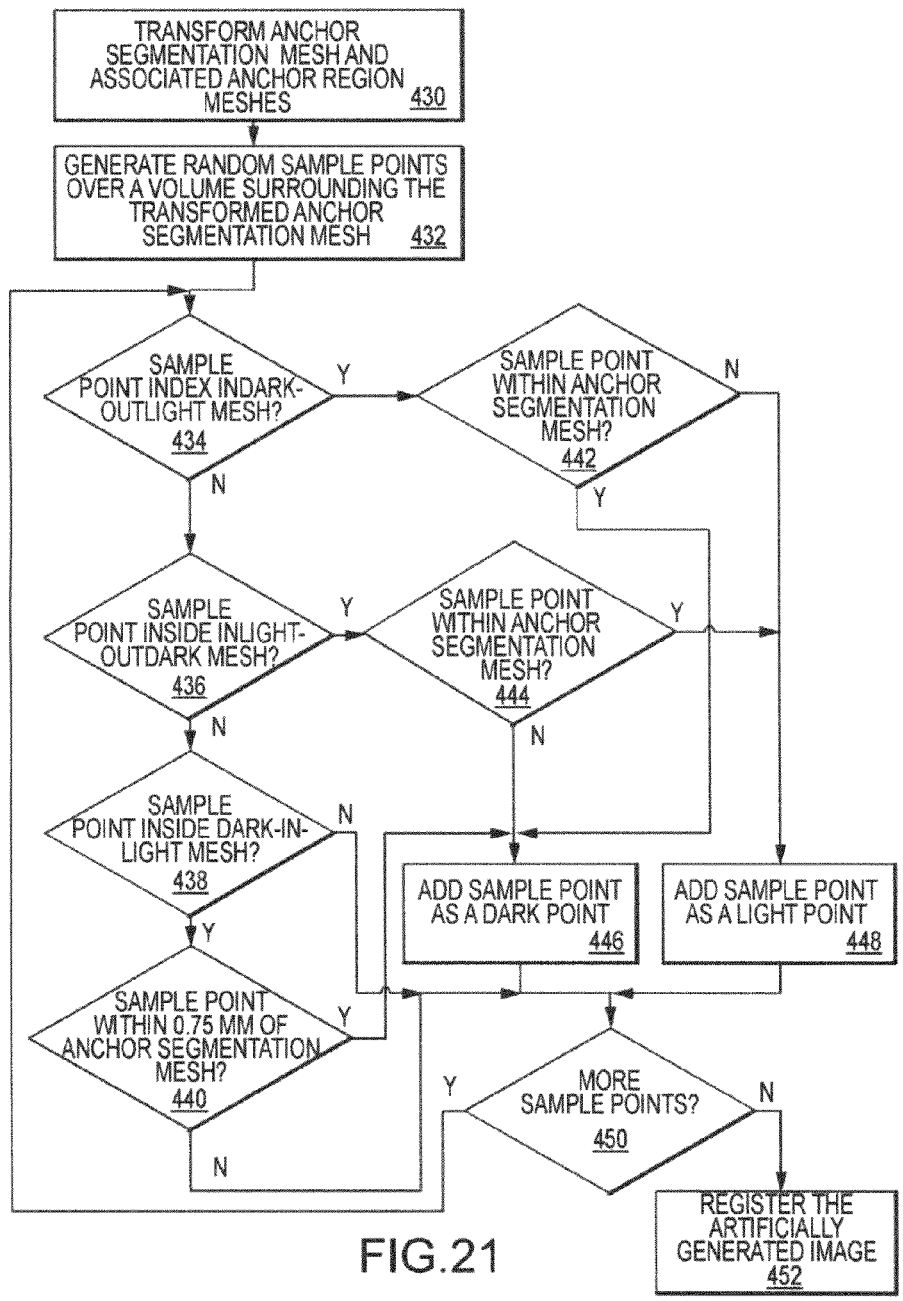
FIG. 21 depicts a flowchart illustrating one method for refining the registration results using anchor segmentation and anchor regions.

Once the position and shape of the feature of interest of the joint has been determined using image registration (operation 370 of FIG. 16), the registration results may be refined using anchor segmentation and anchor regions (operation 372 of FIG. 16). FIG. 21 depicts a flowchart illustrating one method for refining the registration results using anchor segmentation and anchor regions. Typically, during this operation, one more registration may be done using an artificially generated image for the fixed image 394 of the registration framework 390. Use of an artificial image may improve the overall segmentation by registering known good regions that typically do not change from scan to scan to correct for any errors due to diseased and/or low contrast areas that otherwise may distort the registration.

Additionally, the artificial image may be used to increase surface detection precision of articular surfaces and shaft middle regions. The image slices typically have higher resolution in two dimensions (e.g., 0.3-millimeter in the y and z dimensions) and lower resolution in the third dimension (e.g., 2-millimeters in the x dimension). The articular surfaces and shaft middle regions typically are well defined in the image slices due to these surfaces generally being perpendicular to the slices. The surface detection precision may be improved using a combination of 2D and 3D techniques that preserves the in-slice precision by only moving points within slices rather than between slices. Further, a 3D B-spline transform may be used such that the slices are not deformed independently of one another. Since each slice may not contain enough information, deforming each slice independently may result in the registration finding the wrong features. Instead, the slices as a whole may be deformed such that the registration remains near the desired feature. While each slice may be deformed differently, the difference in deformation between slices generally is small such that the changes from one slice to the next are gradual.

In one embodiment, the artificial image may comprise a set of dark and light sample points that may be used by the metric. All dark points in the artificial image may have the same intensity value (e.g., 100) and all light points in the artificial image may have the same intensity value (e.g., 200). It should be appreciated that the correlations are generally insensitive to scaling and zero shift. Thus, any intensity values may be used as long as the dark intensity value is less than the light intensity value.

Initially, operation 430 may apply the cumulative registration transform (computed by operation 370 of FIG. 16) to an anchor segmentation mesh and its three associated anchor region meshes (e.g., InDark-OutLight mesh, InLight-OutDark mesh and Dark-in-Light mesh) to generate a transformed anchor segmentation mesh and associated transformed anchor region meshes (transformed InDark-OutLight anchor mesh, transformed InLight-OutDark anchor mesh and transformed Dark-in-Light anchor mesh) that lie in a space identical to the target image space.

Then, operation 432 generates random sample points lying within a thin volume surrounding the transformed anchor segmentation mesh surface. In one embodiment, this may be a volume having an outer boundary defined by the anchor segmentation mesh surface plus 1.5-millimeters and an inner boundary defined by the anchor segmentation mesh surface minus 1.5-millimeters, which may be referred to herein as the 1.5-millimeter neighborhood. The random sample points may be generated such that they are within the image slices of the target scan but not between the slices. For example, the image slices may be transversal to the x-axis with a spacing of 2-millimeters (at x-axis locations 0.0, 2.0, 4.0, ... ). When a sample point is selected, its x-coordinate may be one of 0.0, 2.0, 4.0, etc. but may not be 1.7, 3.0, or some non-multiple of 2.0.

In one embodiment, voxels may be marked in every image slice that belong to the 1.5-millimeter neighborhood as follows. First, the intersection of the transformed anchor mesh with every image slice may be found. It should be appreciated that the intersection of the anchor mesh with an image slice may be a polyline(s). Then, in each image slice, the polyline segments may be traversed and all pixels that intersect with the mesh may be marked. Next, a Dilate filter may be applied to the marked pixels of each image slice using a radius of 1.5-millimeters. The Dilate filter typically enlarges the marked region by adding all the points that lie within a 1.5-millimeter distance from the originally marked points.

After operation 432, operation 434 determines if a sample point lies inside the transformed InDark-OutLight mesh surface. If operation 434 determines that the sample point lies inside the transformed InDark-OutLight mesh surface, then operation 442 is performed. If operation 434 determines that the sample point does not lie inside the transformed InDark-OutLight mesh surface, then operation 436 is performed.

Operation 442 determines if the sample point lies inside the transformed anchor segmentation mesh surface. If operation 442 determines that the sample point lies inside the transformed anchor segmentation mesh surface, then operation 446 is performed. If operation 442 determines that the sample point does not lie inside the transformed anchor segmentation mesh surface, then operation 448 is performed.

Operation 436 determines if the sample point lies inside the transformed InLight-OutDark mesh surface. If operation 436 determines that the sample point lies inside the transformed InLight-OutDark mesh surface, then operation 444 is performed. If operation 436 determines that the sample point does not lie inside the transformed InLight-OutDark mesh surface, then operation 438 is performed.

Operation 444 determines if the sample point lies inside the transformed anchor segmentation mesh surface. If operation 444 determines that the sample point lies inside the transformed anchor segmentation mesh surface, then operation 448 is performed. If operation 444 determines sample point does not lie within the transformed anchor segmentation mesh surface, then operation 446 is performed.

Operation 438 determines if the sample point lies inside the transformed Dark-In-Light mesh surface. If operation 438 determines that the sample point lies inside the transformed Dark-In-Light mesh surface, then operation 440 is performed. If operation 438 determines that the sample point does not lie inside the transformed Dark-In-Light mesh surface, then operation 450 is performed.

Operation 440 determines if the sample point is within 0.75-millimeter of the surface of the transformed anchor segmentation mesh. If operation 440 determines that the sample point is within 0.75-millimeter of the surface of the transformed anchor segmentation mesh, then operation 446 is performed. If operation 440 determines that the sample point is not within 0.75-millimeter of the surface of the anchor segmentation mesh, then operation 450 is performed.

Operation 446 adds the sample point to the artificial image as a dark point. Then, operation 450 is performed.

Operation 448 adds the sample point to the artificial image as a light sample point. Then, operation 450 is performed.

Operation 450 determines if there are more randomly generated samples points to be added to the artificial image. If operation 450 determines that there are more randomly generated sample points to be added to the artificial image, then operation 434 is performed. If operation 450 determines that there are no more randomly generated sample points to be added to the artificial image, then operation 452 is performed.

Figure 22:
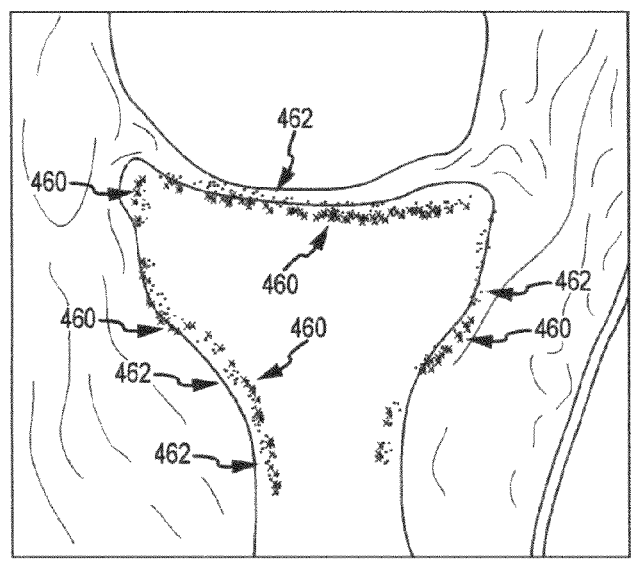
FIG. 22 depicts a set of randomly generated light sample points and dark sample points of a tibia.

FIG. 22 depicts a set of randomly generated light sample points 460 and dark sample points 462 over the target MRI 464. In one embodiment, approximately 8,000 sample points (light and dark) may be generated over the entire artificial image.

Referring again to FIG. 21, if operation 450 determines that there are no more randomly generated sample point to be added to the artificial image, operation 452 registers the set of dark and light points to the target MRI scan. This operation may perform a registration similar to the registration operation 196 (depicted in FIG. 17). In this transformation, a subset of B-spline deformable transformations may be performed that move points along their respective slices, but not transversal to their respective slices.

In a B-spline deformable transform, a translation vector for every control point (e.g., in the set of J×K×L control points) may be specified. To specify a transform that moves any point in 3D space along the y and z slice coordinates but not along the x coordinate, a restriction on the choice of translation vectors in the control points may be introduced. In one embodiment, only translation vectors with the x coordinate set equal to zero may be used to move points in the plane of the slice (e.g., the y and z directions) but not transversal to the slice (e.g., the x direction).

The use of anchor region meshes which typically are well pronounced in most image scans, may reduce registration errors due to unhealthy areas and/or areas with minimal contrast differences between the feature to be segmented and surrounding image areas. For example, in the area where a healthy bone normally has cartilage, a damaged bone may or may not have cartilage. If cartilage is present in this damaged bone region, the bone boundary separates the dark cortical bone from the gray cartilage matter. If cartilage is not present in this area of the damaged bone, there may be white liquid matter next to the dark cortical bone or there may be another dark cortical bone next to the damage bone area. Thus, the interface from the cortical bone to the outside matter in this region of the damaged bone typically varies from MRI scan to MRI scan. In such areas, the interface between the cortical and the inner cancellous bone may be used as an anchor region.

The use of a subset of B-Spline deformable transforms may reduce errors due to the 2-millimeter spacing between image slices.

Figure 23:
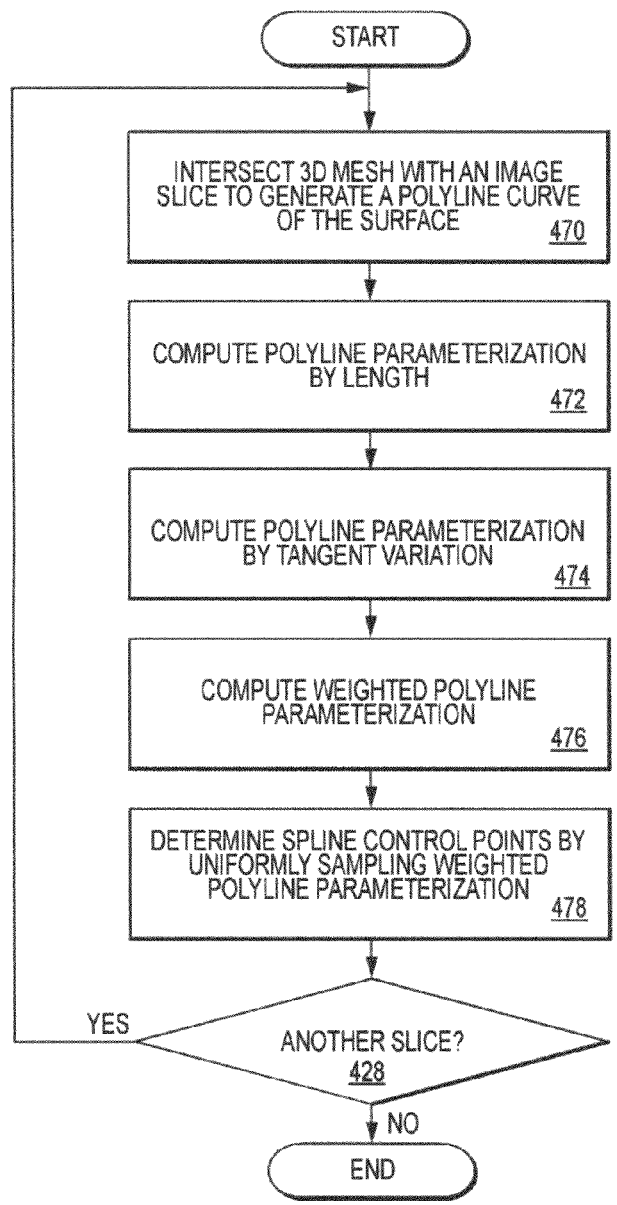
FIG. 23 depicts a flowchart illustrating one method for generating spline curves to outline features of interest in each target MRI slice.

FIG. 23 depicts a flowchart illustrating one method for generating spline curves outlining the surface of a feature of interest in each target MRI slice (e.g., operation 376 of FIG. 16). Initially, operation 470 intersects the generated 3D mesh model of the feature surface with a slice of the target scan data. The intersection defines a polyline curve of the surface of the feature (e.g., bone) in each slice. Two or more polyline curves may be generated in a slice when the bone is not very straightly positioned with respect to the slice direction. In such instances, the intersection of the mesh with the slice plane may generate two or more polyline curves.

A polyline curve is a piecewise linear approximation to a curved feature shape. Generally, this curve should be easy to manipulate with a set of control points. The polyline curve may have many segments, making it more difficult to manipulate the polyline curve (e.g., during operation 254 or 260 of FIG. 6). One embodiment may generate one or more Kochanek splines from the polyline curve. Each spline typically has a smaller number of control points and typically fits the polyline curve with about 0.2-millimeter deviation. Generally, a Kochanek spline may have more control points along the high curvature regions of the polyline curve and fewer control points along low curvature regions (i.e., where the curve tends to be flatter) of the polyline curve.

Figure 24:
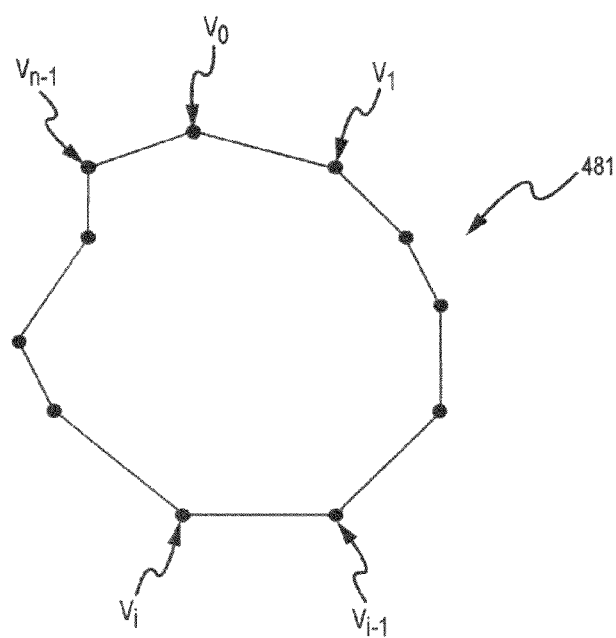
FIG. 24 depicts a polyline curve with n vertices.

Once a polyline curve has been generated, operation 472 may compute a polyline parameterization, $L_i$, as a function of the polyline's length. FIG. 24 depicts a polyline curve 481 with n vertices, $V_0, V_1, \ldots V_{i-1}, V_i \ldots V_{n-1}$. Note that vertex $V_0$ follows vertex $V_{n-1}$ to form a closed contour curve. The length of a segment connecting vertices Vi−1 and Vi may be denoted by $\Delta L_i$ such that the length parameterization, $L_i$, of the polyline at vertex $V_i$ may be expressed as:

$$L_i = \Delta L_0 + \Delta L_1 + \ldots + \Delta L_i.$$

Next, operation 474 may compute a polyline parameterization, $A_i$, as a function of the polyline's tangent variation. The absolute value of the angle between a vector connecting vertices $V_{i-1}$ and $V_i$ and a vector connecting vertices $V_i$ and $V_{i+1}$ may be denoted by $\Delta A_i$ such that the tangent variation parameter $A_i$ at vertex $V_i$ may be expressed as:

$$A_i = \Delta A_0 + \Delta A_1 + \ldots + \Delta A_i.$$

Then, operation 476 determines a weighted sum parameterization of the polyline length and tangent variation parameterizations. In one embodiment the weighted sum parameterization, $W_i$, at vertex $V_i$ may be computed as:

$$W_i = \alpha * L_i + \beta * A_i$$

where $\alpha$ may be set to 0.2 and $\beta$ may be set to 0.8 in one embodiment.

Then, operation 478 may perform a uniform sampling of the polyline using the W parameterization results determined by operation 476. In one embodiment, a spacing interval of approximately 3.7 of the W parameter value may be used for positioning K new sample points. First, K may be computed as follows:

$$K = \text{ROUND}(W_n/3.7 + 0.5).$$

That is, the W parameter value, which is the last computed value $W_n$, may be divided by 3.7 and the result rounded up to the nearest integer to get the number of new sample points. Then, the spacing of the sample points, $\Delta W$ may be computed as:

$$\Delta W = W_n/K.$$

Finally, the K new sample points, which are uniformly spaced, may be positioned at intervals $\Delta W$ of the parameter W. The resulting sample points may be used as control points for the Kochanek splines to convert the polyline into a spline. A Kochanek spline generally has a tension, a bias and a continuity parameter that may be used to change the behavior of the tangents. That is, a closed Kochanek spline with K control points typically is interpolated with K curve segments. Each segment has a starting point, an ending point, a starting tangent and an ending tangent. Generally, the tension parameter changes the length of the tangent vectors, the bias parameter changes the direction of the tangent vectors and the continuity parameter changes the sharpness in change between tangents. In certain embodiments, the tension, bias and continuity parameters may be set to zero to generate a Catmull-Rom spline.

In one embodiment, operation 478 may perform a linear interpolation of $W_i$ and $W_{i+1}$ to locate a sample point that lies between $W_i$ and $W_{i+1}$. The interpolated value of W may be used to determine the corresponding sample location in the segment connecting vertices $V_i$ and $V_{i+1}$.

In certain embodiments, operation 478 may divide the W parameter value by six to obtain the new number of sample points K. That is, $$K = \text{ROUND}(W_n/6 + 0.5).$$

Then, a measure of closeness (i.e., how closely the spline follows the polyline) may be computed as follows. First, the spline is sampled such that there are seven sample points in every arc of the spline (i.e., 7*K sample points). Then, the sum of the squared distances of the sample points to the polyline may be computed. Next, the coordinates of the K control points are varied (i.e., two*K parameters). Then, a local optimization algorithm is used to find the closest spline. If the closest spline found during the optimization is not within a certain precision (e.g., within approximately 0.4-millimeter of the polyline), then the number of control points, K, may be increased by one. The new number of control points may be uniformly distributed along the W parameter, and another optimization performed to find the new closest spline. Generally one to two optimizations provide a spline that follows the polyline with the desired degree of precision (e.g., within approximately 0.2-millimeter).

Finally, operation 480 determines if a spline curve(s) should be generated for another image slice. If operation 480 determines that a spline curve should be generated for another slice, then operation 472 is performed. If operation 480 determines that there are no more image slices to be processed, the method terminates.

As discussed above, in one embodiment, the output of the segmentation may be a triangular mesh (e.g., a 3D surface model) of the segmented bone(s) of a joint (e.g., the femur and tibia of a knee joint). The mesh generated generally represents a watertight surface that closely follows the segmentation contour curves of the slices, smoothly interpolates between the segmentation contour curves, and may have a low triangular count.

In one embodiment, a triangular mesh may be generated as follows. The segmentation data may be represented in 3D using (x, y, z) coordinates with the image slices transversal to the x direction. Thus, the segmentation contours lie in yz planes with fixed values of x. Initially, an in-slice distance image may be computed for each segmented slice. The value of each (y, z) pixel in an in-slice distance image is the distance to the closest point in the contours when the point is located inside one of the contours and is the inverse (i.e., negative) of the distance to the closest point in the contours when the point is outside all of the contours.

Then, a marching cubes algorithm may be applied to the in-slice distance images to generate the mesh. The marching cubes algorithm is a computer algorithm for extracting a polygonal mesh of an isosurface (i.e., the contours) from a three-dimensional scalar field (or voxels). The algorithm typically proceeds through the voxels, taking eight neighbor voxels at a time (thus forming an imaginary cube) and determines the polygon(s) needed to represent the part of the isosurface (i.e., contour) that passes through the imaginary cube. The individual polygons are then fused into the desired surface. The generated mesh generally passes through the zero level of the signed distance function in each slice such that the mesh lies close to the contours.

It is to be appreciated that the image resolution in the y and z directions typically determines how well the zero level of the signed distance function approximates the original contours and may also determine the triangular count in the resulting mesh. In one embodiment, a voxel size of 1.5-millimeters in the y and z directions may be used. This typically yields deviations within 0.1-millimeter of the original contours and produces a smooth mesh.

In one embodiment, a smoothing operation may be performed in the x direction (i.e., transversal to the image slices) to compensate for surface waviness that may have been introduced when the automatically generated contours were adjusted (e.g., during operation 260 of FIG. 6). Such waviness may occur in regions of an image slice where there is minimal contrast variation and the curve is positioned by the technician. Typically a smooth best guess mesh in uncertain areas may be desired when generating a planning model that may be used to locate the position of an implant. Alternatively, a smooth overestimation may be desired in uncertain areas such as in an arthritic model used to create a jig.

In one embodiment, simple smoothing may be used and the amount of smoothing (i.e., how much a voxel value may be modified) may be controlled by two user specified parameters, MaxUp and MaxDown. After an average is computed for a voxel, it is clamped using these values to limit the amount of smoothing. The smoothing operation typically does not change the image much in areas where the image contrast is good. For smooth best guess averaging in uncertain areas, MaxUp and MaxDown may each be set to 1 millimeter. For smooth overestimation averaging in uncertain regions, MaxUp may be set to 2-millimeters and MaxDown may be set to 0-millimeter.

Figure 25:
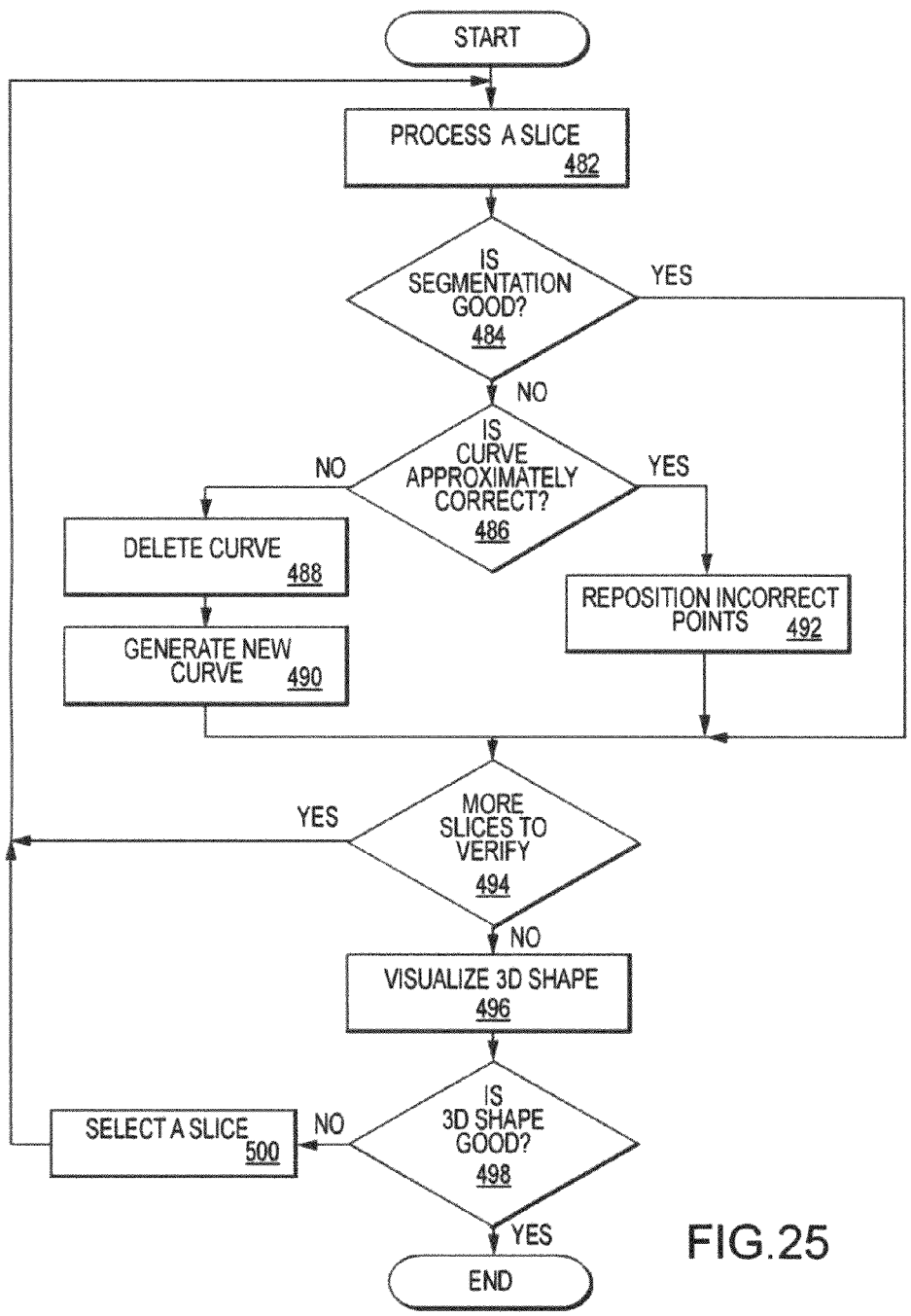
FIG. 25 depicts a flowchart illustrating one method for adjusting segments.

The operation of adjusting segments of the segmentation process will now be described with reference to FIG. 25, which depicts a flowchart for one method of adjusting segments (e.g., operation 254 or operation 260 of the flowchart depicted in FIG. 6). In one embodiment, the segmentation data may be manually adjusted by a trained technician sitting in front of a computer 6 and visually observing the automatically generated contour curves in the image slices on a computer screen 9. By interacting with computer controls 11, the trained technician may manually manipulate the contour curves. The trained technician may visually observe all of the contours as a 3D surface model to select an image slice for further examination.

Initially, in operation 482 a slice is selected for verification. In one embodiment, the slice may be manually selected by a technician.

Next, operation 484 determines if the segmentation contour curve in the selected slice is good. If operation 484 determines that the segmentation contour curve is good, then operation 494 is performed. If operation 484 determines that the segmentation contour curve is not good, then operation 486 is performed.

Operation 486 determines if the segmentation contour curve is approximately correct. If operation 486 determines that the contour curve is approximately correct, then operation 492 is performed.

Figure 26:
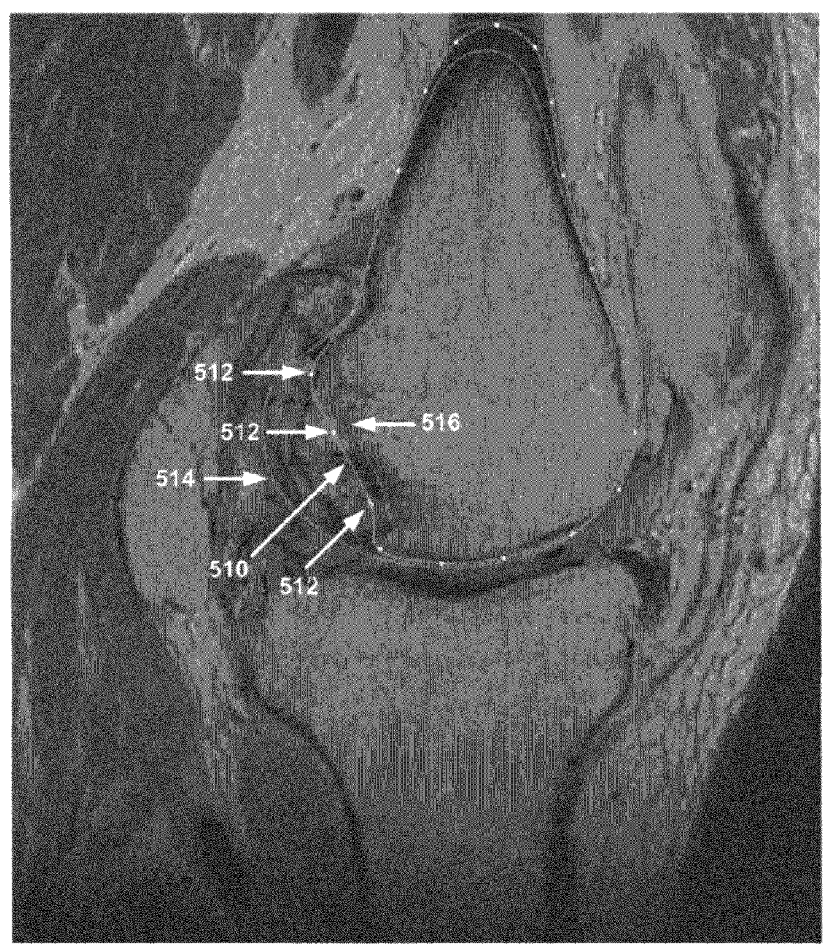
FIG. 26 is a sagittal plane image slice depicting a contour curve with control points outlining a femur with superimposed contour curves of the femur from adjacent image slices.

In operation 492 incorrect points of the segmentation contour curve may be repositioned. In one embodiment this may be performed manually by a trained technician. It is to be appreciated that it may be difficult for the technician to determine where the correct contour curve should be located in a particular slice. This may be due to missing or unclear bone boundaries and/or areas with little contrast to distinguish image features. In one embodiment, a compare function may be provided to allow the technician to visually compare the contour curve in the current slice with the contour curves in adjacent slices. FIG. 26 depicts an image showing the contour curve 510 (e.g., a spline curve) with control points 512 of the contour curve 510 for the current image slice as well the contour curves 514, 516 of the previous and next image slices, respectively, superimposed on the current image slice.

It may be difficult to determine where the correct segmentation contour curve should be located due to missing or unclear bone boundaries due to the presence of unhealthy areas, areas with limited contrast differences, and/or voxel volume averaging. When visually comparing adjacent slices, the technician may visualize the data in 2D planes (xy, yz, and xz) and in 3D. In one embodiment, the technician may select an area for examination by positioning a cross hair on a location in any window and clicking a mouse button to select that image point. The cross hair will be placed at the desired point and may be used to indicate the same location when the data is visualized in each window.

The technician may use the spline control points to manipulate the shape of the curve. This may be done by using a mouse to click on a control point and dragging it to a desired location. Additionally, the technician may add or delete spline curve control points. This may be done by using a mouse to select two existing control points between which a control point will be inserted or deleted. Alternatively, the technician may use a mouse cursor to point to the location on the curve where a control point is to be inserted. In one embodiment, by pressing the letter I on a keyboard and then positioning the cursor at the desired location, clicking the left mouse button will insert the control point. A control point may be deleted by pressing the letter D on the keyboard and then positioning the cursor over the desired control point to be deleted. The selected control point will change color. The selected control point will be deleted when the left mouse button is clicked.

Referring again to FIG. 25, if operation 486 determines that the contour curve is not approximately correct, then operation 488 is performed to delete the curve. Then, operation 490 is performed.

Operation 490 generates a new segmentation contour curve for the image slice. In one embodiment, a technician may use a spline draw tool to insert a new spline curve. With the spline draw tool, the technician may click on consecutive points in the current slice to indicate where the spline curve should be located and a spline curve is generated that passes through all of the indicated points. A right mouse click may be used to connect the first and last points of the new spline curve. Alternatively, the technician may use a paste command to copy the spline curve(s) from the previous slice into the current slice. The spline control points may then be manipulated to adjust the spline curves to follow the feature in the current image slice.

In another embodiment, a paste similar command may be used by the technician to copy the spline curve from the previous slice into the current slice. Rather then pasting a copy of the spline curve from the previous slice, the spline curve may be automatically modified to pass through similar image features present in both slices. This may be done by registering a region around the spline curve in the previous slice that is from about 0.7-millimeter outside of the curve to about 5.0-millimeter within the curve. Initially, this region is registered using an affine transformation. Then, the result of the affine transform may be used as a starting value for a B-Spline deformable transformation. The metric used for the transform may be the local correlation in sample points metric described previously. Typically, more sample points may be taken closer to the curve and fewer sample points taken farther away from the curve. Next, the spline control points may be modified by applying the final transformation found to the spline control points. Additionally, the trained technician may adjust from zero to a few control points in areas where the bone boundary changes a lot from the slice due to the bone being tangent to the slice or in areas of limited contrast (e.g., where there is an osteophyte growth). Then, operation 492 is performed.

Operation 494 determines if there are additional slices to be verified. If operation 494 determines that there are additional slices to be verified, operation 482 is performed.

If operation 494 determines that there are no more slices to be verified, then operation 496 is performed. Operation 496 generates a 3D surface model of the segmented bone.

Figure 27:
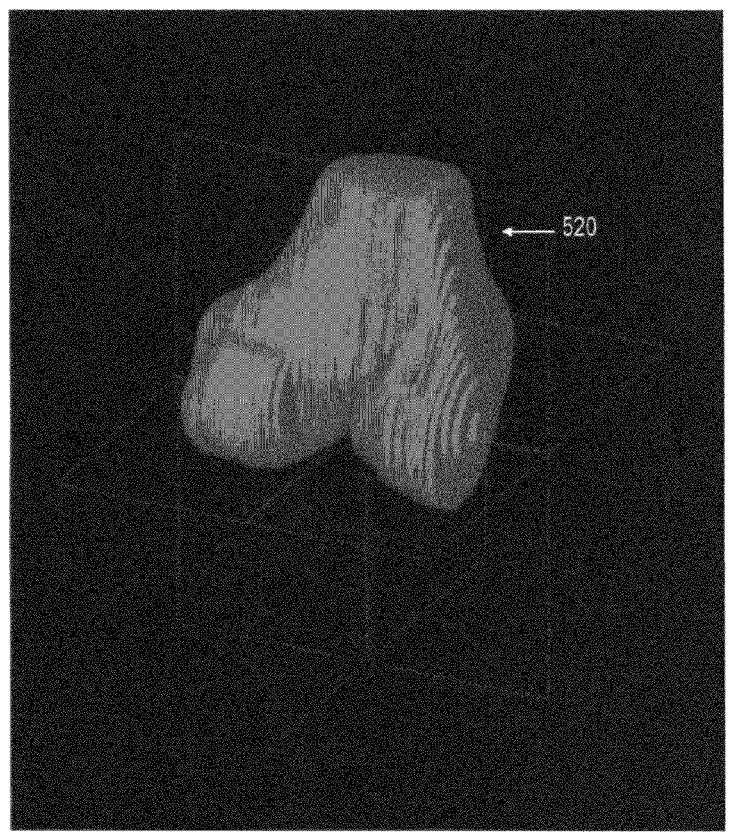
FIG. 27 depicts a 3D slice visualization of a femur showing the voxels inside of the spline curves.

Then, operation 498 determines if the 3D surface model is good. In one embodiment, a technician may manually determine if the 3D surface model is good. The technician may use a spline 3D visualization tool that generates a slice visualization showing the voxels inside all of the splines in 3D, as illustrated by the 3D shape 520 depicted in FIG. 27. This spline 3D visualization tool typically may be generated in real time to provide interactive updates to the technician as the spline curves are manually edited. Alternatively, a mesh visualization may be generated in response to a technician command. The mesh visualization typically generates a smooth mesh that passes close to all the spline curves, e.g., mesh 290 depicted in FIG. 9.

If operation 498 determines that the 3D model is not good, then operation 500 is performed. Operation 500 selects a slice lying in an area where the 3D shape is not good. In one embodiment, a technician may manually select the slice. Then, operation 482 is performed.

If operation 498 determines that the 3D model is good, then the method terminates.

The 3D surface models of the lower end of the femur and the upper end of the tibia of a patient's knee may be used to create arthroplasty jigs and/or implants. For example, the models may be used to create femur and tibia jigs that can be used with a patient's femur and tibia as disclosed in the various U.S. patent applications incorporated by reference herein in this Detailed Description and filed by Park and Park et al. Automatic segmentation of image data to generate 3D bone models may reduce the overall time required to perform a reconstructive surgery to repair a dysfunctional joint and may also provide improved patient outcomes.

Although the present invention has been described with respect to particular embodiments, it should be understood that changes to the described embodiments and/or methods may be made yet still embraced by alternative embodiments of the invention. For example, certain embodiments may operate in conjunction with a MRI or a CT medical imaging system. Yet other embodiments may omit or add operations to the methods and processes disclosed herein. Accordingly, the proper scope of the present invention is defined by the claims herein.

What is claimed is:

1. A method of partitioning an image of a bone into a plurality of regions, the method comprising the acts of: using a medical imaging machine to obtain a plurality of volumetric image slices of the bone; employing selective resolution over different areas of the bone in the image slices; using at least one computer to generate a plurality of spline curves associated with the bone; verifying that at least one of the plurality of spline curves follow a surface of the bone; and using at least one computer to create a three dimensional (3D) mesh representation based upon the at least one of the plurality of spline curves.

2. The method of claim 1, wherein a uniform spacing between the plurality of slices is 2 millimeters.

3. The method of claim 1, wherein the plurality with slices are in the sagittal, transversal or coronal directions.

4. The method of claim 1, wherein the volumetric image slices represent a portion of the bone that makes contact with a second bone.

5. The method of claim 1, wherein the plurality of spline curves defines the bone's shape and orientation.

6. The method of claim 1, wherein the method yields a planning model of the bone.

7. The method of claim 1, wherein the act of verifying comprises the act of examining neighboring slices in the plurality.

8. The method of claim 1, further comprising the act of integrating a representation of a model bone into the image of the bone.

9. The method of claim 8, where the representation of the model bone has no damaged cancellous or cortical matter.

10. A method of partitioning an image of a bone into a plurality of regions, the method comprising the acts of: using a medical imaging machine to obtain a plurality of volumetric image slices of the bone; using at least one computer to generate a plurality of spline curves associated with the bone; verifying that at least one of the plurality of spline curves follow a surface of the bone; and using at least one computer to generate a three dimensional (3D) mesh representation based upon the at least one of the plurality of spline curves, wherein at least one image slice within the plurality includes voxels that are distorted through voxel volume averaging.

11. A method of generating a representation of a model bone, the method comprising the acts of: obtaining an image scan of the representation as a plurality of slices; segmenting each slice in the plurality using one or more segmentation curves, wherein the act of segmenting excludes segmenting cartilage associated with the representation of the model bone; using at least one computer to generate a mesh of the representation; adjusting each slice in the plurality to include areas where the boundary area of the bone is stable between successive image scans; and using at least one computer to generate an anchor segmentation such that the anchor segmentation follows a boundary of the representation of the model bone.

12. The method of claim 11, wherein the act of obtaining the image scan occurs through the use of magnetic resonance imaging (MRI).

13. The method of claim 11, wherein Gaussian smoothing is employed.

14. The method of claim 11, wherein the boundary of the representation of the model bone comprises a boundary between cortical and cancellous bone matter.

15. The method of claim 11, further comprising the act of connecting a plurality of cortical and cancellous boundary area together to obtain the anchor segmentation.

16. The method of claim 15, wherein the plurality of cortical and cancellous boundaries are disjoint.

17. The method of claim 11, wherein at least one cancellous voxel is within the anchor segmentation and at least one cortical voxel is external to the anchor segmentation.

18. The method of claim 11, wherein at least one cortical voxels lies along the boundary of the representation of the model bone and at least one cancellous voxel lies adjacent the boundary of the representation of the model bone.

19. The method of claim 11, further comprising the act of generating a 3D mesh representing the representation of the model bone.

20. A method of generating a representation of a model bone, the method comprising the acts of: obtaining an image scan of the representation as a plurality of slices; segmenting each slice in the plurality using one or more segmentation curves; using at least one computer to generate a mesh of the representation; adjusting each slice in the plurality to include areas where the boundary area of the bone is stable between successive image scans; and using at least one computer to generate an anchor segmentation such that the anchor segmentation follows a boundary of the representation of the model bone, wherein at least a portion of the representation of the model bone exists between two segmentation curves.

21. A method of generating a representation of a model bone, the method comprising the acts of: obtaining an image scan of the representation as a plurality of slices; segmenting each slice in the plurality using one or more segmentation curves; using at least one computer to generate a mesh of the representation; adjusting each slice in the plurality to include areas where the boundary area of the bone is stable between successive image scans; and using at least one computer to generate an anchor segmentation such that the anchor segmentation follows a boundary of the representation of the model bone, wherein osteophytes are excluded from the anchor segmentation.

22. A method of generating a representation of a model bone, the method comprising the acts of: obtaining an image scan of the representation as a plurality of slices; segmenting each slice in the plurality using one or more segmentation curves; using at least one computer to generate a mesh of the representation; adjusting each slice in the plurality to include areas where the boundary area of the bone is stable between successive image scans; using at least one computer to generate an anchor segmentation such that the anchor segmentation follows a boundary of the representation of the model bone; and repositioning a point on the one or more segmentation curves by comparing point placement of adjacent segmentation curves.

23. A method of segmenting a target bone using a representation of a model bone, the method comprising the acts of: registering a segmented form of the representation to an image scan of the target bone; refining the registration of the segmented form of the representation near a boundary of the target bone; using at least one computer to generate a mesh from the segmented form of the representation; and using at least one computer to generate a plurality of spline curves that approximate the intersection of the mesh and one or more slices from the image scan of the target bone, wherein the act of refining comprises averaging one or more voxels of adjacent slices.

24. The method of claim 23, wherein the method is performed on a joint.

25. The method of claim 23, further comprising applying a transform within one or more slices.

26. The method of claim 25, wherein the act of applying the transforms includes moving points within a plane of the slices but not transversal to the slices.

27. The method of claim 23, further comprising the act of verifying that at least one of the pluralities of spline curves follows a surface of the target bone.

28. The method of claim 27, wherein the act of verifying comprises the act of comparing at least two adjacent slices.

29. A method for refining registration of a representation of a model bone to a target bone, the method comprising the acts of: using at least one computer to transform an anchor segmentation mesh; using at least one computer to generate a plurality of random points around the transformed anchor segmentation mesh; determining if each point in the plurality lies inside one or more of the following meshes: Inpark-OutLight, InLight-Outpark, or Dark-In-Light determining whether one or more of the plurality of points lie within a threshold distance of the surface of the transformed anchor segmentation mesh; and adding each point in the plurality as a dark point or light point depending upon whether the point lies within the Inpark-OutLight, InLight-Outpark, or Dark-In-Light meshes and to determine of the point lies inside or outside of the transformed anchor segmentation mesh, wherein the act of determining if each point lies within a threshold distance comprises the acts of: intersecting the anchor segmentation mesh with each image slice; noting one or more pixels of the image slice that intersect with the anchor segmentation mesh; and filtering the one or more pixels outside the threshold distance.

30. The method of claim 29, wherein the plurality of points are within image slices.

31. The method of claim 29, wherein the act of filtering occurs using a Dilate filter.

32. The method of claim 29, wherein the threshold distance is 0.75 millimeters.

33. The method of claim 29, wherein the act of transforming comprises the act of generating one or more spline curves.

34. A non-transitory computer readable medium comprising computer executable instructions to perform the method as in any of claims 10, 11, 20, 21, 22, 23 and 29.

* * * * *

UNITED STATES PATENT AND TRADEMARK OFFICE
CERTIFICATE OF CORRECTION

| | |
|---|---|
| PATENT NO. | : 8,311,306 B2 |
| APPLICATION NO. | : 12/386105 |
| DATED | : November 13, 2012 |
| INVENTOR(S) | : Elena Pavlovskaia et al. |

It is certified that error appears in the above-identified patent and that said Letters Patent is hereby corrected as shown below:

Claim 34, column 40, line 8, add the numeral "1," after the word --claims--.

Signed and Sealed this
Ninth Day of April, 2013

Teresa Stanek Rea
*Acting Director of the United States Patent and Trademark Office*